US011732087B2

(12) United States Patent
Aoshima et al.

(10) Patent No.: US 11,732,087 B2
(45) Date of Patent: *Aug. 22, 2023

(54) BIOMASS-RESOURCE-DERIVED POLYESTER AND PRODUCTION PROCESS THEREOF

(71) Applicant: Mitsubishi Chemical Corporation, Tokyo (JP)

(72) Inventors: Takayuki Aoshima, Yokkaichi (JP); Yasuaki Miki, Yokohama (JP); Katsuhisa Kumazawa, Yokkaichi (JP); Satoshi Katou, Yokohama (JP); Tadashi Uyeda, Yokkaichi (JP); Toyomasa Hoshino, Yokkaichi (JP); Noboru Shintani, Yokohama (JP); Kenji Yamagishi, Yokohama (JP); Atsushi Isotani, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,898

(22) Filed: Jun. 16, 2022

(65) Prior Publication Data

US 2023/0124462 A1 Apr. 20, 2023

Related U.S. Application Data

(63) Continuation of application No. 17/085,666, filed on Oct. 30, 2020, now Pat. No. 11,560,449, which is a continuation of application No. 16/290,140, filed on Mar. 1, 2019, now Pat. No. 10,870,727, which is a continuation of application No. 15/693,646, filed on Sep. 1, 2017, now Pat. No. 10,287,393, which is a continuation of application No. 13/586,916, filed on Aug. 16, 2012, now abandoned, which is a continuation of application No. 13/168,513, filed on Jun. 24, 2011, now Pat. No. 9,080,009, which is a continuation of application No. 12/858,046, filed on Aug. 17, 2010, now Pat. No. 8,021,864, which is a continuation of application No. 11/912,212, filed as application No. PCT/JP2006/308472 on Apr. 21, 2006, now Pat. No. 7,985,566.

(30) Foreign Application Priority Data

| Apr. 22, 2005 | (JP) | 2005-125318 |
| Apr. 22, 2005 | (JP) | 2005-125319 |
| Apr. 22, 2005 | (JP) | 2005-125320 |
| Apr. 22, 2005 | (JP) | 2005-125321 |
| Apr. 26, 2005 | (JP) | 2005-127757 |
| Apr. 26, 2005 | (JP) | 2005-127761 |
| Apr. 27, 2005 | (JP) | 2005-128886 |
| Dec. 27, 2005 | (JP) | 2005-375353 |
| Dec. 27, 2005 | (JP) | 2005-375354 |
| Dec. 27, 2005 | (JP) | 2005-375355 |

(51) Int. Cl.
| C08G 63/16 | (2006.01) |
| C08G 63/20 | (2006.01) |
| C08G 63/78 | (2006.01) |
| C08L 67/02 | (2006.01) |
| C08L 1/00 | (2006.01) |
| C08L 3/00 | (2006.01) |
| C08L 5/00 | (2006.01) |
| C08L 99/00 | (2006.01) |

(52) U.S. Cl.
CPC ............. *C08G 63/16* (2013.01); *C08G 63/20* (2013.01); *C08G 63/78* (2013.01); *C08L 67/02* (2013.01); *C08L 1/00* (2013.01); *C08L 3/00* (2013.01); *C08L 5/00* (2013.01); *C08L 99/00* (2013.01); *C08L 2201/06* (2013.01)

(58) Field of Classification Search
CPC ........ C08G 63/16; C08G 63/20; C08G 63/78; C08L 67/02; C08L 1/00; C08L 3/00; C08L 5/00; C08L 99/00; C08L 2201/06
See application file for complete search history.

(56) References Cited

U.S. PATENT DOCUMENTS

| 3,903,152 A | 9/1975 | Matsubara et al. |
| 3,936,421 A | 2/1976 | Hayashi et al. |
| 4,013,624 A | 3/1977 | Hoeschele |
| 4,067,779 A | 1/1978 | List |
| 4,086,270 A | 4/1978 | Wynkoop et al. |
| 4,447,595 A | 5/1984 | Smith et al. |
| 5,034,105 A | 7/1991 | Berglund et al. |

(Continued)

FOREIGN PATENT DOCUMENTS

| CN | 1246165 | 3/2000 |
| CN | 1379818 | 11/2002 |

(Continued)

OTHER PUBLICATIONS

Declaration under 37 C.F.R. 1.132 by Go Takahashi, Jun. 24, 2011, 4 pages.
European Brief Communication dated May 20, 2022 in European Patent Application No. 11158665.7, 9 pages.
European Brief Communication dated May 27, 2022 in European Patent Application No. 11158665.7, 2 pages.

(Continued)

*Primary Examiner* — Robert S Jones, Jr.
(74) *Attorney, Agent, or Firm* — Oblon, McClelland, Maier & Neustadt, L.L.P.

(57) ABSTRACT

The present invention provides a resin capable of contributing greatly to solve environmental problems and problems related to exhaustion of fossil fuel resources and having physical properties suited for practical use.
The polyester according to the present invention has a diol and a dicarboxylic acid as constituent components and has an amount of terminal acid of 50 equivalents/metric ton or less.

13 Claims, 4 Drawing Sheets

Specification includes a Sequence Listing.

(56) References Cited

U.S. PATENT DOCUMENTS

| | | |
|---|---|---|
| 5,143,833 A | 9/1992 | Datta |
| 5,143,834 A | 9/1992 | Glassner et al. |
| 5,168,055 A | 12/1992 | Datta et al. |
| 5,266,725 A | 11/1993 | Jackson |
| 5,770,435 A | 6/1998 | Donnelly et al. |
| 5,852,164 A | 12/1998 | Akai et al. |
| 5,869,301 A | 2/1999 | Nghiem et al. |
| 6,245,879 B1 | 6/2001 | Kelsey et al. |
| 6,284,904 B1 | 9/2001 | Ponnampalam |
| 6,323,307 B1 | 11/2001 | Bigg et al. |
| 6,350,531 B1 | 2/2002 | Sugimoto |
| 6,376,223 B1 | 4/2002 | Staley |
| 7,538,176 B2 | 5/2009 | Fuji et al. |
| 7,563,606 B2 | 7/2009 | Aoyama et al. |
| 7,985,566 B2 | 7/2011 | Aoshima et al. |
| 8,021,864 B2 | 9/2011 | Aoshima et al. |
| 2002/0099150 A1 | 7/2002 | Kumazawa et al. |
| 2003/0017559 A1 | 1/2003 | Donnelly et al. |
| 2003/0036626 A1 | 2/2003 | Hayes et al. |
| 2003/0082756 A1 | 5/2003 | Burch et al. |
| 2004/0225107 A1 | 11/2004 | Sunkara et al. |
| 2005/0069997 A1 | 3/2005 | Adkesson et al. |
| 2005/0070738 A1 | 3/2005 | Isotani |
| 2006/0172401 A1 | 8/2006 | Yamagishi |
| 2006/0205048 A1 | 9/2006 | Murase et al. |
| 2006/0276674 A1 | 12/2006 | Kushiku et al. |
| 2006/0293492 A1 | 12/2006 | Aoshima et al. |

FOREIGN PATENT DOCUMENTS

| | | |
|---|---|---|
| CN | 1570123 | 1/2005 |
| DE | 1 912 497 | 10/1970 |
| EP | 0 389 103 | 9/1990 |
| EP | 0 405 707 | 1/1991 |
| EP | 0 410 728 A1 | 1/1991 |
| EP | 0 683 191 A | 11/1995 |
| EP | 0 826 478 A2 | 3/1998 |
| EP | 953037 | 11/1999 |
| EP | 1012323 | 6/2000 |
| EP | 1 148 075 | 10/2001 |
| EP | 1 243 573 | 9/2002 |
| EP | 06732230.5 | 4/2006 |
| EP | 1 679 332 | 7/2006 |
| EP | 1 818 352 | 8/2007 |
| EP | 1 882 712 | 1/2008 |
| EP | 1 882 712 A1 | 1/2008 |
| EP | 2 204 396 A | 7/2010 |
| EP | 2 223 950 | 9/2010 |
| GB | 844957 | 6/1960 |
| GB | 1213882 | 11/1970 |
| GB | 1 224 157 | 3/1971 |
| JP | 62-285779 | 12/1987 |
| JP | 62-285779 A | 12/1987 |
| JP | 2-283289 | 11/1990 |
| JP | 3-30685 | 2/1991 |
| JP | 6-239778 A | 8/1994 |
| JP | 6-287278 | 10/1994 |
| JP | 7-82188 A | 3/1995 |
| JP | 8-259679 | 10/1996 |
| JP | 9-110971 | 4/1997 |
| JP | 9-227666 A | 9/1997 |
| JP | 2000-500350 | 1/2000 |
| JP | 2000-302724 | 10/2000 |
| JP | 2000-515389 | 11/2000 |
| JP | 2001-26642 | 1/2001 |
| JP | 2001-400076 | 2/2001 |
| JP | 2001-323056 | 11/2001 |
| JP | 2001-335626 | 12/2001 |
| JP | 2002-212830 | 7/2002 |
| JP | 2004-124087 | 4/2004 |
| JP | 2004-198768 | 7/2004 |
| JP | 2004-277718 | 10/2004 |
| JP | 2005-27533 | 2/2005 |
| JP | 2005-27633 | 2/2005 |
| JP | 2005-65841 | 3/2005 |
| JP | 2005-95169 | 4/2005 |
| JP | 2005-113127 | 4/2005 |
| JP | 2005-125318 | 4/2005 |
| JP | 2005-125319 | 4/2005 |
| JP | 2005-125320 | 4/2005 |
| JP | 2005-125321 | 4/2005 |
| JP | 2005-127757 | 4/2005 |
| JP | 2005-127761 | 4/2005 |
| JP | 2005-128886 | 4/2005 |
| JP | 2005-139287 | 6/2005 |
| JP | 2005-163032 | 6/2005 |
| JP | 2005-162801 | 6/2006 |
| JP | 2006-238843 | 9/2006 |
| JP | 2007-197652 | 8/2007 |
| JP | 2007-197654 | 8/2007 |
| JP | 2009-41036 | 2/2009 |
| JP | 4380654 | 10/2009 |
| JP | 4380704 B2 | 12/2009 |
| JP | 4575086 | 8/2010 |
| JP | 2010209311 | 9/2010 |
| WO | WO 97/18528 | 5/1997 |
| WO | WO 98/93930 | 8/1998 |
| WO | 01/56980 | 8/2001 |
| WO | 2004/101479 | 11/2004 |
| WO | WO 2005/012390 | 2/2005 |
| WO | 2005/026232 | 3/2005 |
| WO | 2005/026349 | 3/2005 |
| WO | WO 2005/030973 | 4/2005 |
| WO | WO 2006/115226 A1 | 11/2006 |

OTHER PUBLICATIONS

European Commencement of Proceedings Before the Board of Appeal with Petition of Opponent 02 issued May 31, 2022 in European Patent Application No. 11158665.7, 4 pages.

European Commencement of Proceedings Before the Board of Appeal with Petition of Opponent 03 issued May 31, 2022 in European Patent Application No. 11158665.7, 3 pages.

European Grounds of Appeal by Opposition Against European Patent No. 2 365 017 dated Jul. 26, 2022, 44 pages.

European Grounds of Appeal by Opposition Against European Patent No. 2 365 017 dated Jul. 25, 2022, 18 pages.

Liguist Declaration from Frank McGee executed Jul. 25, 2022 with attached Exhibits A and B, 24 pages.

Expert Declaration from Jefferson Clay Lievense executed Jul. 25, 2022, 4 pages.

Office Action dated May 12, 2014 in Japanese Patent Application No. 2008-261248 (with English language translation).

Office Action dated May 12, 2014 in Japanese Patent Application No. 2008-261317 (with English language translation).

Observation by a Third Party dated Jan. 13, 2014 in European Application No. 06732230.5.

Aldrich Catalogue, Handbook of Fine Chemicals and Laboratory Equipment, 2000-2001, 2 pages.

Yan Liu. et al., "New Segmented Poly(Ester-Urethane)s from Renewable Resources", Journal of Polymer Science: Part A: Polymer Chemistry, vol. 39, 2001, pp. 630-639.

Ellsabetta Ranucci, et al., "New biodegradable polymers from renewable sources. High molecular weight poly(ester carbonate)s from succinic acid and 1,3-propanediol", Macromol. Rapid Commun., vol. 21, 2000, pp. 680-684.

Observation by third party issued Nov. 29, 2013, in Japanese Patent Application No. 2012-286185 with English translation.

Office Action dated Jan. 14, 2014, in Japanese Patent Application No. 2012-286185 with English translation.

"Saturated Polyester Resin Handbook", Nikkan Shimbun (1989) 1 front page, pp. 261-267.

Office Action as received In the corresponding Japanese Patent Application No. 2012-286185 dated Oct. 22, 2013 w/English Translation.

H.C. KI, et al., "Synthesis, characterization and biodegradability of the biodegradable aliphatic-aromatic random copolyesters", Polymer, 42, 2001, pp. 1849-1861.

(56) References Cited

OTHER PUBLICATIONS

T. K. NG, et al., "Production of Tetrahydrofuran/1,4 Butanediol by a Combined Biological and Chemical Process", Biotechnology and Bioengineering Symp., No. 17, 1986, pp. 355-363.
Li-Min Deng, et al., A new biodegradable copolyester poly(butylene succinate-co-ethylene succinate-co-ethylene terephthalate), Acta Materialia, 52, 2004, pp. 5871-5878.
Office Action dated Feb. 13, 2013 in Japanese Application No. 2009-118267 (With English Translation).
European Search Report as received in the corresponding European Patent Application No. 11158675.6 dated Apr. 2, 2015.
Office Action as received in the corresponding European Patent Application No. 10 002 323.3-1302 dated Apr. 10, 2015.
Office Action as received in the corresponding Chinese Patent Application No. 201310070301.7 dated Apr. 16, 2015 w/English Translation.
Second Office Action as received in the Chinese Patent Application No. 201310070534.7 dated Apr. 16, 2015 w/English Translation.
European Office Action dated Apr. 12, 2017 in Patent Application No. 10 002 323,3.
Chinese Office Action dated Mar. 31, 2017 in Patent Application No. 201310069915.3 (with English Translation).
Observations by a third party as received in the corresponding European Patent Application No. 06732230.5 / 1882712 dated Mar. 14, 2017.
Annex A, Preparation of samples for biodegradability tests, OWS reference Nos. GMO159/0309-1, GMO159-0336-3, GMO159-0309-2 and GMO159-0336-1, No date available, pp. 1-2.
Annex B, Final Report BVDV-1, Lynn Serbruyns, Natural soil biodegradation test of GMO159-0309-1 and GMO159-0309-2, Jun. 4, 2015, pp. 1-18.
Annex C, Lynn Serbruyns, Final Report ABR-1, Natural soil biodegradation test on GM0159-0336-1, GM0159-0336-3, GM0029-0273 and GM0029-0274, Nov. 9, 2015, pp. 1-20.
Grounds Appeal (2), Sep. 27, 2016, pp. 1-52.
Grounds Appeal (3) Sep. 16, 2016 In European Patent No. 1882712 (for Application No. 06732230.5-1452).
Shandong Cathay Lineng Biotechnology Co., Ltd. (Certificate of Analysis), Date of Certification Oct. 12, 2003, 1 page.
Novamont S.p.A., Research and Development, Analytical Chemistry Laboratory, "Determination of sulfur atom content of commercial monomers and polymers" Sep. 21, 2016, pp. 1-7.
Novamont S.p.A., Research & Developent, Analytical Chemistry Laboratory; Biodegradation Laboratory, "Biodegradation of PBS with fossil-fuel derived succinic acid and PBS with biomass resource derived succinic acid", pp. 1-4, Sep. 23, 2016.
Grounds Appeal (1), Sep. 22, 2016 in European Patent Application No. 1882712.
DICAM (Department of Civil, Chemical, Environmental and Materials Engineering (Declaration) w/Curriculum Vitae and Publications attached, Sep. 22, 2016 by Professor Nadia Lotti, 33 pages.
Sipol, Declaration on Process Conditions for the Production of TF01U during the years 2003 to 2005, Sep. 26, 2016, 2 pages w/TF01U sample produced according to the TF01U 03006023 lot process conditions attached.
Novamont S.p.A. Research & Development, Analytical Chemistry Laboratory, "Determination of nitrogen atom content of commercialmonomers" w/Elemental analyzer multi EA 5000 attached.
Shandong Cathay Lineng Biotechnology Co., Ltd., (Certificate of Analysis) Date of Certification Feb. 2, 2004, 1 page.
Notification of Reexamination as received in the corresponding Chinese Patent Application No. 201310069915.3 dated Aug. 25, 2017 w/ English translation.
Engineering Plastics Handbook-Materials edited by MA Zhikang, et al., China Machine Press, Jun. 2004, p. 269 w/ Partial English translation.
Application of Plastics in Food Packaging, Feng Shaosheng, Sep. 1988, p. 172, w/Partial English translation.
Office Action as received in the corresponding European Patent Application No. 11 158 665.7-1302 dated Dec. 18, 2017, 4 pages.
Office Action as received in the corresponding Chinese Patent Application No. 201310069915.3 dated Jan. 31, 2018 w/English Translation.
Polyester Fiber Technology and Engineering, edited by GUO Dasheng and Wang Wenke, China Textile & Apparel Press, Mar. 2001, pp. 27-31, w/partial English translation.
Summons to Oral Proceedings Issued on Jul. 18, 2018 as received in the corresponding European Patent Application No. 06732230. 5/1882712.
Glassner, D.A.; Elankovan, P.; Beacom, D.R.; Berglund, K.A.; Applied Biochemistry and Biotechnology, vol. 51/52, 1995; p. 73-82.
Lomako, S.V. et al; Analytica Chimica Acta, vol. 582, 2006; p. 216-222.
Expected Materials on the Future, vol. 1, No. 11, p. 31 (2001).
T.K. Ng et al., "Production of Tetrahydrofuren/1,4 Butanediol by a Combined Biological and Chemical Process," Biotechnology and Bioengineering Symp., No. 17, (1988) pp. 355-383.
Karen M. Draths et al., "Environmentally Compatible Synthesis of Adipic Acid from D-Glucose," J. Am. Chem. Soc., 1994, 116, 399-400.
J.G. Zelkus, et al., "Biotechnology of Succinic Acid Production and Markets for Derived Industrial products," Appl. Microbiol Biotechnol, No. 51, pp. 545-552 (1999).
"Katalog Handbuch Feinchemikallen Aldrich 1999-2000" 1999 XP002579018 p. 272, p. 1465.
Communication of a Notice of Opposition filed Jan. 19, 2011, in European Patent Application No. 06732230.5-2102 / 1882712.
Pillin et al, *Polymer Engineering and Science*, 2001, vol. 41, No. 2, pp. 178-191.
Karayannidis, et al, *Polymer Degradation and Stability*, 1994, vol. 44, pp. 9-15.
Kurian, *Journal of Polymers and the Environment*, 2005, vol. 13, No. 2, pp. 159-167.
Liu et al, *Ind. Eng. Chem. Res.*, 2005, vol. 44, pp. 857-862.
Buxbaum, *Angew. Chem. Internat. Edit.*, 1968, vol. 7, No. 3 pp. 182-190.
Biklaris et al, *Polymer Degradation and Stability*, 1999, vol. 63, pp. 213-218.
Boswell, *Chemical Market Reporter*, 2001, vol. 250, No. 8.
Aravind et al, *Polymer*, 2004, vol. 45, pp. 4925-4937.
Emmenegger et al, *The Application Notebook*, 2010, pp. 4-7.
Communication of Notice of Opposition dated Jan. 26, 2011, In Patent Application No. 06732230.5-2102 / 1882712.
Communication of Notice of Oppostion dated Jan. 28, 2011, In Patent Application No. 06732230.5-2102 / 1882712.
Kim, *Sanop Misuengmul Hokhoechoi*, 1998, vol. 25, No. 8, pp. 465-469 (English abstract only).
Mueller, Biopolymers, *Biodegradability of polymers: Regulations and methods for testing* Wiley-VCH, 2003, pp. 366-391.
Dagli Innocenti, "Handbook of biodegradable polymers (Biodegradation behaviour of polymers in the soil)" Rapra Technology Limited, 2005, pp. 57-102.
Mistsubishi Chemical Commercial Brochure for Total Nitrogen Analyzer Model TN-110, 2000.
ASTM Designation D 6069-98, Standard Test Method for Trace Nitrogen in Aromatic Hydrocarbons by Oxidative Combustion and Reduced Pressure Chemiluminescence Detection.
Kim et al, *Fibers and Polymers*, 2010, vol. 11, No. 2, pp. 170-176.
Ecoflex—Biologically Degrading Copolyesters; Presentation held at Biodegradable Plastic 2002, Dec. 2002, Frankfurt.
J. Scheirs, Compositional and Feltura Analysis of Polymers; John Wiley & Sons Ltd., 2000; pp. 364-369.
Specifiche techniche acido succinico, Brenntag, Aug. 3, 2005.
Product specification adipic acid, BASF, May 24, 2004.
Leaflet Succinic acid Anhydride, DSM Fine Chemicals, Nov. 2001.
Communication of Notice of Opposition dated Jan. 28, 2011, In Patent Application No. 06732230.5-2102 / 1882712.
Zimmerman et al, *Polymer Engineering and Science*, 1980, vol. 20, No. 10, pp. 680-683.
Zhang et al, *Macromolecules*, 1995, vol. 28, pp. 7622-7629.
Burgoyne et al, *J. Meter. Sci.*, 2007, vol. 42, pp. 2867-2878.

(56) References Cited

OTHER PUBLICATIONS

Office Action with English Translation dated Apr. 6, 2011 in corresponding Chinese Application No. 200680013513.X, filed Apr. 21, 2006.
Valdya, P.D., Mahajani, V.V.: Journal of Chemical Technology and Biotechnology, 2003, pp. 504-511.
Office Action dated Jan. 17, 2012 in Chinese Patent Application No. 200680013513.X w/English Translation.
Notification of Reasons for Refulsal dated Jul. 6, 2012 In Japanese Patent Application No. 2009-117246 (with English translation).
Cardinal, E.V., et al.: Microbiological Assay of Com. Steep Liquor for Amino Acid Content, Journal of Biological Chemistry, 1948, p. 609-612.
Sedlak, R.; Phoshorus and Nitrogen Removal from Municipal Wastewater; Principles and Practices, 1991, p. 37.
Japanese Office Action drafted Sep. 28, 2012, in Patent Applicaton No. 2009-117246 (with English-language translation).
Japanese Office Action drafted Aug. 9, 2012, In Patent Application No. 2009-118267 (with English-language translation).
Japanese Office Action dated Nov. 6, 2012 in Patent Application No. 2009-118267 with English Translation.
Notice of Opposition of EP 11158665.7 dated Jun. 12, 2020, with evidentiary attachments.
Notice of Opposition of EP 11158665.7 dated Apr. 14, 2020, with evidentiary attachments.
Concise Encyclopedia of Polymer Science and Engineering, John Wiley &Sons, Inc., 1990, pp. 709-710.
Hytrel® Injection Molding Guide, E.I. du Pont de Nemours and Company, © 2000.
Administrative judgement as received in the corresponding Chinese patent application 201310069915.3 w/English Translation, dated Jun. 24, 2020.
Machine translation of Atsushi et al., JP 2005139287A, published Jun. 2, 2005.
Decision of Technical Board of Appeal dated Jan. 9, 2020 in European Patent Application No. 06732230.5, 21 pages.
Lai, S.M., et al.; Journal of Applied Polymer Science, 2005, vol. 97, p. 257-264.
Declaration of Dr. Milizia Tiziana (2 pgs ); Aug. 1, 2014.
Declaration of Mr. Bruno De Wilde (2 pgs.); May 5, 2014.
Declaration of Dr. Francesco Degli Innocenti (2 pgs.); Aug. 1, 2014.
Declaration of Dr. Roberto Vallero (10 pgs.); Aug. 1, 2014.
Declaration or Dr. Roberto Vallero (4 pages); Sep. 22, 2014.
Declaration of Prof. Nadia Lotl (4 pgs.), Sep. 22, 2016.
Curriculum Vitae for Prof. N. Lottl (2 pgs.).
Publications Prof. Lotti (1 page).
Declaration of Pasquale Corani; SIPOL (2pgs.); Sep. 26, 2016.
Experimental Report SIP0L re, alleged prior use TF01U (4 pgs.) dated Sep. 22, 2016.
Experimental Report on nitrogen atom content (14 pgs.) dated Sep. 21, 2016.
Date sheet Brassylic Acid (1 page).
Data sheet Dodecenedioic Acid (1 page).
Experimental Report on sulfur atom content of commercial monomers (8 pages) dated Sep. 21, 2016.
Experimental Report Biodegradation of PBS with fossil-fuel derived succinic acid and PBS with biomass resource derived succinic acid (4 pgs.) dated Sep. 23, 2016.
Raller et al.; "Zur Carboxylgruppenbestimmung in Polybutylenterephthalat", Acta Polymerica 30 (1979), Issue No. 9. p. 598 to 599 (with English Translation).
Experimental Report re. Carboxylate groups (2 pgs.) dated Aug. 10, 2018.
Data sheet Cleartuf® Pet; Jan. 2013.
Declaration of Dr. Tiziana Milizia (2pgs.); Oct. 31, 2018.
Production Sheet Diester (Ricetta No. 53) dated May 2, 2003 (with English Translation).
Production Sheet Diester (Ricetta No. 52) dated May 2, 2003 (with English Translation).
Technical Information (Composizione lotti etilensebacato), 1 page (with English Translation).
Experimental Report Biodegradation of PBAT with fossil-fuel derived 1,4-butanediol and PBAT with biomass resource derived 1;4-butanediol, (5 pages) dated Jan. 3, 2019.
Decision of the OD in EP 1 882 712, May 17, 2016.
Decision of the Board of Appeal in EP 1 882 712, T 1657/16 (21 pgs.); Oct. 14, 2019.
Minutes of Oral Proceedings before the Board of Appeal in EP 1882712, T 1647/16 (3 pgs.); Oct. 14, 2019.
Concise Encyclopedia of Polymer Science and Engineering: John Wiley & Sons, Inc; Copyright 1990; pp. 709 and 710.
Excerpt fromUllman's Encyclopedia of Industrial Chemistry; $6^{th}$ ed.; 2003, vol. 28, pp. 88-89 and 100-101.
Herbert A. Pohl; Analytical Chemistry; vol. 26, Oct. 1954, pp. 1614-1616.
Information on nitrogen analyzer TN-05.
Supplement to Physical Property Evaluation Example 3 of EP 2 365 017 B1. 1 page.
Declaration filed in U.S. Appl. No. 13/586,916.
Experimental Report by Mr. Satoshi Kato, 6 pgs.
N. Gabashvili et al.; Bulletin of the Georgian Academy of Sciences, 154, No. 2, 1996, pp. 289-292.
Olagoke Olabisr: "Handbook of Thermoplastics"; Marcel Dekker, Inc.; Copyright 1997, pp. 465-489.
Glossary of Basic Terms in Polymer Science (IUPAC Recommendations 1996): Pure Appl. Chem, vol. No. 68, 8, pp. 1591-1595, 1996.
EP Submission of Opponent 2, Nov. 17, 2021, (10 pgs.).
EP Submission of Opponent 3, Dec. 17, 2021 (9 pgs.).
EP Submission of Opponent 3; Nov. 18, 2021 (4 pgs.).
EP Submission of Opponent2; Dec. 20, 2021 (3 pgs.).
Extended European Search Report issued in EP Application No. 21178703.1; dated Feb. 11, 2022 (6 pgs.).
Extended European Search Report issued in EP Application No. 21178729.6, dated Feb. 11, 2022 (7 pgs.).
Extended European Search Report issued in EP Application No. 21178732.0; dated Mar. 1, 2022 (5 pgs.).
Extended European Search Report issued in EP Application No. 211787080.0: dated Mar. 21, 2022 (7 pgs.).
Sriram Varadarajan et al.; "Catalytic Upgrading of Fermentation-Derived Organic Acids"; Biotechnol. Prog., vol. 15, No. 5; Oct. 1, 1999; pp. 845-854.
Extended European Search Report issued in EP Application No. 21178711.4; dated Mar. 18, 2022 (6 pgs.).
European Office Action dated Feb. 10, 2021 in European Application No. 11158665.7, 22 pages.
Appeal No. T1657/16-3.3.03 from opponents in the corresponding European Patent Application No. 06732230.5 /1882712 dated Oct. 10, 2016 (First Page Only).
Akira Hoshino, et al., "Influence of Weather Conditions and Soil Properties on Degradation of Biodegradable Plastics in Soil", Soil Sci. Plant. Nutr., 47, (1), 35-43, 2001.
Handbook of Thermoplastic Polyesters, vol. 1, Homopolymers, Copolymers, Blend, and Composites, Editor: Prof. Stoyko Fakirov, Chapter 13, by Z. Roslaniec, et al. "Synthesis and Characteristics of Polyester-Based Thermoplastic Elastomers: Chemical Aspcts" pp. 620-622 & 655 (2002).
Novamount S.p.A., "Effect of sample temperature dissolution on amount of terminal acid groups in polyesters", Sep. 23, 2016, pp. 1-10.
Office Action as received in the corresponding Chinese Patent Application No. 201310069915.3 dated Aug. 12, 2016 w/English Translation.
Wojcik, B.H.; Industrial and Engineering Chemistry, 1948, p. 210-216.
Observations by third party dated Dec. 28, 2018 as received in the corresponding European patent Application No. 10002323.3-1302 / 2204396 w/English Translation.
Office Action as received In the corresponding Chinese Patent Application No. 201310069915.3 dated Dec. 3, 2018 w/English translation.

(56) References Cited

OTHER PUBLICATIONS

Office Action as received in the corresponding Chinese Patent Application No. 201310069916.3 dated Aug. 12, 2016 w/English Translation.
European Office Action dated Feb. 10, 2021 in EP application No. 11168665.7, 22 pages.
Summons to attend oral proceeding issued on Aug. 7, 2015 in the corresponding European patent application No. 06732230.5.
Office Action as received in the corresponding Chinese Patent Application No. 201310069896.4 dated Apr. 16, 2015 w/Engllsh Translation.
Office Action as received in the corresponding Chinese Patent Application No. 201310069915.3 dated Apr. 16, 2015 w/Engllsh Translation.
European Search Report as received in the corresponding European Patent Application No. 11158666.5-1302 /2366726 dated Apr. 13, 2015.
European Search Report as received in the corresponding European Patent Application No. 11158680.6-1302 /2402383 dated Apr. 14, 2015.
European Search Report as received in the corresponding European Patent Application No. 11158666.7 dated Mar. 30, 2015.
Combined Chinese Office Action and Search Report dated Jul. 8, 2014 in Patent Application No. 201310069915.3 (with English Translation).
Combined Chinese Office Action and Search Report dated Jul. 8, 2014 in Patent Application No. 201310069896.4 (with English Translation).
Combined Chinese Office Action and Search Report dated Jul. 8, 2014 in Patent Application No. 201310070534.7 (with English Translation).
Combined Chinese Office Action and Search Report dated Jul. 8, 2014 in Patent Application No. 201310070301.7 (with English Translation).

SEQUENCE LISTING

```
<160> NUMBER OF SEQ ID NOS: 16

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctttttaac ccatcacata tacctgccgt tcac                               34

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaggttagg aatacggtta gccatttgcc tg                                 32

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggtctgcc tcgtgaagaa g                                             21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
ctcattagaa aaactcatcg agcatca         27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgatgaaaga aaccgtcggc         20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtcagaaga actgcttctg         20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agttgcatac gcatacgcac tga         23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagactggga ctgcaacgtc ttg         23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatctttcag ctgctcacac gtga         24

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatcttaggt cactaaaact aattcag                                        27

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatccaggag gcattaatta agcggccgcg ggccctgca                            39

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggcccgcgg ccgcttaatt aatgcctcct g                                   31

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accttaatta atgtcgactc acacatcttc aacgcttcca gca                      43

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttgggccca ggtttaggaa acgacgacga tcaagtcgcc acct                     44

<210> SEQ ID NO 15
<211> LENGTH: 3423
<212> TYPE: DNA
<213> ORGANISM: Brevibacterium flavum
<220> FEATURE:
<221> NAME/KEY: CDS
<222> LOCATION: (1)..(3420)

<400> SEQUENCE: 15

| atg | tcg | act | cac | aca | tct | tca | acg | ctt | cca | gca | ttc | aaa | aag | atc | ttg | 48 |
| Met | Ser | Thr | His | Thr | Ser | Ser | Thr | Leu | Pro | Ala | Phe | Lys | Lys | Ile | Leu | |
| 1 | | | | 5 | | | | | 10 | | | | | 15 | | |

| gta | gca | aac | cgc | ggc | gaa | atc | gcg | gtc | cgt | gct | ttc | cgt | gca | gca | ctc | 96 |
| Val | Ala | Asn | Arg | Gly | Glu | Ile | Ala | Val | Arg | Ala | Phe | Arg | Ala | Ala | Leu | |
| | | | 20 | | | | | 25 | | | | | 30 | | | |

| gaa | acc | ggt | gca | gcc | acg | gta | gct | att | tac | ccc | cgt | gaa | gat | cgg | gga | 144 |
| Glu | Thr | Gly | Ala | Ala | Thr | Val | Ala | Ile | Tyr | Pro | Arg | Glu | Asp | Arg | Gly | |
| | | 35 | | | | | 40 | | | | | 45 | | | | |

| | | |
|---|---|---|
| tca ttc cac cgc tct ttt gct tct gaa gct gtc cgc att ggt act gaa<br>Ser Phe His Arg Ser Phe Ala Ser Glu Ala Val Arg Ile Gly Thr Glu<br>50       55            60 | | 192 |
| ggc tca cca gtc aag gcg tac ctg gac atc gat gaa att atc ggt gca<br>Gly Ser Pro Val Lys Ala Tyr Leu Asp Ile Asp Glu Ile Ile Gly Ala<br>65           70            75            80 | | 240 |
| gct aaa aaa gtt aaa gca gat gct att tac ccg gga tat ggc ttc ctg<br>Ala Lys Lys Val Lys Ala Asp Ala Ile Tyr Pro Gly Tyr Gly Phe Leu<br>            85            90            95 | | 288 |
| tct gaa aat gcc cag ctt gcc cgc gag tgc gcg gaa aac ggc att act<br>Ser Glu Asn Ala Gln Leu Ala Arg Glu Cys Ala Glu Asn Gly Ile Thr<br>100           105           110 | | 336 |
| ttt att ggc cca acc cca gag gtt ctt gat ctc acc ggt gat aag tct<br>Phe Ile Gly Pro Thr Pro Glu Val Leu Asp Leu Thr Gly Asp Lys Ser<br>    115           120           125 | | 384 |
| cgt gcg gta acc gcc gcg aag aag gct ggt ctg cca gtt ttg gcg gaa<br>Arg Ala Val Thr Ala Ala Lys Lys Ala Gly Leu Pro Val Leu Ala Glu<br>130           135           140 | | 432 |
| tcc acc ccg agc aaa aac atc gat gac atc gtt aaa agc gct gaa ggc<br>Ser Thr Pro Ser Lys Asn Ile Asp Asp Ile Val Lys Ser Ala Glu Gly<br>145           150           155           160 | | 480 |
| cag act tac ccc atc ttt gta aag gca gtt gcc ggt ggt ggc gga cgc<br>Gln Thr Tyr Pro Ile Phe Val Lys Ala Val Ala Gly Gly Gly Gly Arg<br>            165           170           175 | | 528 |
| ggt atg cgc ttt gtt tct tca cct gat gag ctt cgc aaa ttg gca aca<br>Gly Met Arg Phe Val Ser Ser Pro Asp Glu Leu Arg Lys Leu Ala Thr<br>    180           185           190 | | 576 |
| gaa gca tct cgt gaa gct gaa gcg gca ttc ggc gac ggt tcg gta tat<br>Glu Ala Ser Arg Glu Ala Glu Ala Ala Phe Gly Asp Gly Ser Val Tyr<br>195           200           205 | | 624 |
| gtc gag cgt gct gtg att aac ccc cag cac att gaa gtg cag atc ctt<br>Val Glu Arg Ala Val Ile Asn Pro Gln His Ile Glu Val Gln Ile Leu<br>210           215           220 | | 672 |
| ggc gat cgc act gga gaa gtt gta cac ctt tat gaa cgt gac tgc tca<br>Gly Asp Arg Thr Gly Glu Val Val His Leu Tyr Glu Arg Asp Cys Ser<br>225           230           235           240 | | 720 |
| ctg cag cgt cgt cac caa aaa gtt gtc gaa att gcg cca gca cag cat<br>Leu Gln Arg Arg His Gln Lys Val Val Glu Ile Ala Pro Ala Gln His<br>            245           250           255 | | 768 |
| ttg gat cca gaa ctg cgt gat cgc att tgt gcg gat gca gta aag ttc<br>Leu Asp Pro Glu Leu Arg Asp Arg Ile Cys Ala Asp Ala Val Lys Phe<br>    260           265           270 | | 816 |
| tgc cgc tcc att ggt tac cag ggc gcg gga act gtg gaa ttc ttg gtc<br>Cys Arg Ser Ile Gly Tyr Gln Gly Ala Gly Thr Val Glu Phe Leu Val<br>275           280           285 | | 864 |
| gat gaa aag ggc aac cac gtt ttc atc gaa atg aac cca cgt atc cag<br>Asp Glu Lys Gly Asn His Val Phe Ile Glu Met Asn Pro Arg Ile Gln<br>290           295           300 | | 912 |
| gtt gag cac acc gtg act gaa gaa gtc acc gag gtg gac ctg gtg aag<br>Val Glu His Thr Val Thr Glu Glu Val Thr Glu Val Asp Leu Val Lys<br>305           310           315           320 | | 960 |
| gcg cag atg cgc ttg gct gct ggt gca acc ttg aag gaa ttg ggt ctg<br>Ala Gln Met Arg Leu Ala Ala Gly Ala Thr Leu Lys Glu Leu Gly Leu<br>            325           330           335 | | 1008 |
| acc caa gat aag atc aag acc cac ggt gcg gca ctg cag tgc cgc atc<br>Thr Gln Asp Lys Ile Lys Thr His Gly Ala Ala Leu Gln Cys Arg Ile<br>    340           345           350 | | 1056 |
| acc acg gaa gat cca aac aac ggc ttc cgc cca gat acc gga act atc<br>Thr Thr Glu Asp Pro Asn Asn Gly Phe Arg Pro Asp Thr Gly Thr Ile<br>355           360           365 | | 1104 |

```
acc gcg tac cgc tca cca ggc gga gct ggc gtt cgt ctt gac ggt gca    1152
Thr Ala Tyr Arg Ser Pro Gly Gly Ala Gly Val Arg Leu Asp Gly Ala
        370                 375                 380 gct cag ctc ggt ggc gaa atc acc gca cac ttt gac tcc atg ctg gtg    1200
Ala Gln Leu Gly Gly Glu Ile Thr Ala His Phe Asp Ser Met Leu Val
385                 390                 395                 400 aaa atg acc tgc cgt ggt tcc gat ttt gaa act gct gtt gct cgt gca    1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att    1296
Gln Arg Ala Leu Ala Glu Phe Thr Val Ser Gly Val Ala Thr Asn Ile
        420                 425                 430 ggt ttc ttg cgt gcg ttg ctg cgt gaa gag gac ttt act tcc aag cgc    1344
Gly Phe Leu Arg Ala Leu Leu Arg Glu Glu Asp Phe Thr Ser Lys Arg
            435                 440                 445 atc gcc acc gga ttt atc ggc gat cac cca cac ctc ctt cag gct cca    1392
Ile Ala Thr Gly Phe Ile Gly Asp His Pro His Leu Leu Gln Ala Pro
450                 455                 460 cct gcg gat gat gag cag gga cgc atc ctg gat tac ttg gca gat gtc    1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gca cca    1488
Thr Val Asn Lys Pro His Gly Val Arg Pro Lys Asp Val Ala Ala Pro
                485                 490                 495 atc gat aag ctg ccc aac atc aag gat ctg cca ctg cca cgc ggt tcc    1536
Ile Asp Lys Leu Pro Asn Ile Lys Asp Leu Pro Leu Pro Arg Gly Ser
            500                 505                 510 cgt gac cgc ctg aag cag ctt gga cca gca gcg ttt gcc cgc gat ctc    1584
Arg Asp Arg Leu Lys Gln Leu Gly Pro Ala Ala Phe Ala Arg Asp Leu
        515                 520                 525 cgt gag cag gac gca ctg gca gtt act gat acc acc ttc cgc gat gca    1632
Arg Glu Gln Asp Ala Leu Ala Val Thr Asp Thr Thr Phe Arg Asp Ala
530                 535                 540 cac cag tct ttg ctt gcg acc cga gtc cgc tca ttc gca ctg aag cct    1680
His Gln Ser Leu Leu Ala Thr Arg Val Arg Ser Phe Ala Leu Lys Pro
545                 550                 555                 560 gcg gca gag gcc gtc gca aag ctg act cct gag ctt ttg tcc gtg gag    1728
Ala Ala Glu Ala Val Ala Lys Leu Thr Pro Glu Leu Leu Ser Val Glu
                565                 570                 575 gcc tgg ggc ggt gcg acc tac gat gtg gcg atg cgt ttc ctc ttt gag    1776
Ala Trp Gly Gly Ala Thr Tyr Asp Val Ala Met Arg Phe Leu Phe Glu
            580                 585                 590 gat ccg tgg gac agg ctc gac gag ctg cgc gag gcg atg ccg aat gtg    1824
Asp Pro Trp Asp Arg Leu Asp Glu Leu Arg Glu Ala Met Pro Asn Val
        595                 600                 605 aac att cag atg ctg ctt cgc ggc cgc aac acc gtg gga tac acc cca    1872
Asn Ile Gln Met Leu Leu Arg Gly Arg Asn Thr Val Gly Tyr Thr Pro
610                 615                 620 tac cca gac tcc gtc tgt cgc gcg ttt gtt aag gaa gct gcc acc tcc    1920
Tyr Pro Asp Ser Val Cys Arg Ala Phe Val Lys Glu Ala Ala Thr Ser
625                 630                 635                 640 ggc gtg gac atc ttc cgc atc ttc gac gcg ctt aac gac gtc tcc cag    1968
Gly Val Asp Ile Phe Arg Ile Phe Asp Ala Leu Asn Asp Val Ser Gln
                645                 650                 655 atg cgt cca gca atc gac gca gtc ctg gag acc aac acc gcg gtc gct    2016
Met Arg Pro Ala Ile Asp Ala Val Leu Glu Thr Asn Thr Ala Val Ala
            660                 665                 670 gaa gtg gct atg gct tat tct ggt gat ctt tcc gat ccg aat gaa aag    2064
Glu Val Ala Met Ala Tyr Ser Gly Asp Leu Ser Asp Pro Asn Glu Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 675 |     |     |     |     | 680 |     |     |     |     | 685 |     |      |
| ctc | tac | acc | ctg | gat | tac | tac | ctg | aag | atg | gca | gag | gag | atc | gtc | aag | 2112 |
| Leu | Tyr | Thr | Leu | Asp | Tyr | Tyr | Leu | Lys | Met | Ala | Glu | Glu | Ile | Val | Lys |      |
|     | 690 |     |     |     |     | 695 |     |     |     |     | 700 |     |     |     |     |      |
| tct | ggc | gct | cac | att | ctg | gct | att | aag | gat | atg | gct | ggt | ctg | ctt | cgc | 2160 |
| Ser | Gly | Ala | His | Ile | Leu | Ala | Ile | Lys | Asp | Met | Ala | Gly | Leu | Leu | Arg |      |
| 705 |     |     |     |     | 710 |     |     |     |     | 715 |     |     |     |     | 720 |      |
| cca | gct | gca | gcc | acc | aag | ctg | gtc | acc | gca | ctg | cgc | cgt | gaa | ttt | gat | 2208 |
| Pro | Ala | Ala | Ala | Thr | Lys | Leu | Val | Thr | Ala | Leu | Arg | Arg | Glu | Phe | Asp |      |
|     |     |     |     | 725 |     |     |     |     | 730 |     |     |     |     | 735 |     |      |
| ctg | cca | gtg | cac | gtg | cac | acc | cac | gac | act | gcg | ggt | ggc | cag | ctg | gca | 2256 |
| Leu | Pro | Val | His | Val | His | Thr | His | Asp | Thr | Ala | Gly | Gly | Gln | Leu | Ala |      |
|     |     |     | 740 |     |     |     |     | 745 |     |     |     |     | 750 |     |     |      |
| acc | tac | ttt | gct | gca | gct | caa | gct | ggt | gca | gat | gct | gtt | gac | ggt | gct | 2304 |
| Thr | Tyr | Phe | Ala | Ala | Ala | Gln | Ala | Gly | Ala | Asp | Ala | Val | Asp | Gly | Ala |      |
|     |     | 755 |     |     |     |     | 760 |     |     |     |     | 765 |     |     |     |      |
| tcc | gca | cca | ctg | tct | ggc | acc | acc | tcc | cag | cca | tcc | ctg | tct | gcc | att | 2352 |
| Ser | Ala | Pro | Leu | Ser | Gly | Thr | Thr | Ser | Gln | Pro | Ser | Leu | Ser | Ala | Ile |      |
| 770 |     |     |     |     | 775 |     |     |     |     | 780 |     |     |     |     |     |      |
| gtt | gct | gca | ttc | gcg | cac | acc | cgt | cgc | gat | acc | ggt | ttg | agc | ctc | gag | 2400 |
| Val | Ala | Ala | Phe | Ala | His | Thr | Arg | Arg | Asp | Thr | Gly | Leu | Ser | Leu | Glu |      |
| 785 |     |     |     |     | 790 |     |     |     |     | 795 |     |     |     |     | 800 |      |
| gct | gtt | tct | gac | ctc | gag | cca | tac | tgg | gaa | gca | gtg | cgc | gga | ctg | tac | 2448 |
| Ala | Val | Ser | Asp | Leu | Glu | Pro | Tyr | Trp | Glu | Ala | Val | Arg | Gly | Leu | Tyr |      |
|     |     |     |     |     | 805 |     |     |     |     | 810 |     |     |     |     | 815 |      |
| ctg | cca | ttt | gag | tct | gga | acc | cca | ggc | cca | acc | ggt | cgc | gtc | tac | cgc | 2496 |
| Leu | Pro | Phe | Glu | Ser | Gly | Thr | Pro | Gly | Pro | Thr | Gly | Arg | Val | Tyr | Arg |      |
|     |     |     | 820 |     |     |     |     | 825 |     |     |     |     | 830 |     |     |      |
| cac | gaa | atc | cca | ggc | gga | cag | ctg | tcc | aac | ctg | cgt | gca | cag | gcc | acc | 2544 |
| His | Glu | Ile | Pro | Gly | Gly | Gln | Leu | Ser | Asn | Leu | Arg | Ala | Gln | Ala | Thr |      |
|     |     | 835 |     |     |     |     | 840 |     |     |     |     | 845 |     |     |     |      |
| gca | ctg | ggc | ctt | gcg | gat | cgt | ttc | gaa | ctc | atc | gaa | gac | aac | tac | gcg | 2592 |
| Ala | Leu | Gly | Leu | Ala | Asp | Arg | Phe | Glu | Leu | Ile | Glu | Asp | Asn | Tyr | Ala |      |
|     | 850 |     |     |     |     | 855 |     |     |     |     | 860 |     |     |     |     |      |
| gca | gtt | aat | gag | atg | ctg | gga | cgc | cca | acc | aag | gtc | acc | cca | tcc | tcc | 2640 |
| Ala | Val | Asn | Glu | Met | Leu | Gly | Arg | Pro | Thr | Lys | Val | Thr | Pro | Ser | Ser |      |
| 865 |     |     |     |     | 870 |     |     |     |     | 875 |     |     |     |     | 880 |      |
| aag | gtt | gtt | ggc | gac | ctc | gca | ctc | cac | ctc | gtt | ggt | gcg | ggt | gtg | gat | 2688 |
| Lys | Val | Val | Gly | Asp | Leu | Ala | Leu | His | Leu | Val | Gly | Ala | Gly | Val | Asp |      |
|     |     |     |     | 885 |     |     |     |     | 890 |     |     |     |     | 895 |     |      |
| cca | gca | gac | ttt | gct | gca | gat | cca | caa | aag | tac | gac | atc | cca | gac | tct | 2736 |
| Pro | Ala | Asp | Phe | Ala | Ala | Asp | Pro | Gln | Lys | Tyr | Asp | Ile | Pro | Asp | Ser |      |
|     |     |     | 900 |     |     |     |     | 905 |     |     |     |     | 910 |     |     |      |
| gtc | atc | gcg | ttc | ctg | cgc | ggc | gag | ctt | ggt | aac | cct | cca | ggt | ggc | tgg | 2784 |
| Val | Ile | Ala | Phe | Leu | Arg | Gly | Glu | Leu | Gly | Asn | Pro | Pro | Gly | Gly | Trp |      |
|     |     | 915 |     |     |     |     | 920 |     |     |     |     | 925 |     |     |     |      |
| cca | gag | cca | ctg | cgc | acc | cgc | gca | ctg | gaa | ggc | cgc | tcc | gaa | ggc | aag | 2832 |
| Pro | Glu | Pro | Leu | Arg | Thr | Arg | Ala | Leu | Glu | Gly | Arg | Ser | Glu | Gly | Lys |      |
| 930 |     |     |     |     | 935 |     |     |     |     | 940 |     |     |     |     |     |      |
| gca | cct | ctg | acg | gaa | gtt | cct | gag | gaa | gag | cag | gcg | cac | ctc | gac | gct | 2880 |
| Ala | Pro | Leu | Thr | Glu | Val | Pro | Glu | Glu | Glu | Gln | Ala | His | Leu | Asp | Ala |      |
| 945 |     |     |     |     | 950 |     |     |     |     | 955 |     |     |     |     | 960 |      |
| gat | gat | tcc | aag | gaa | cgt | cgc | aac | agc | ctc | aac | cgc | ctg | ctg | ttc | ccg | 2928 |
| Asp | Asp | Ser | Lys | Glu | Arg | Arg | Asn | Ser | Leu | Asn | Arg | Leu | Leu | Phe | Pro |      |
|     |     |     |     | 965 |     |     |     |     | 970 |     |     |     |     | 975 |     |      |
| aag | cca | acc | gaa | gag | ttc | ctc | gag | cac | cgt | cgc | cgc | ttc | ggc | aac | acc | 2976 |
| Lys | Pro | Thr | Glu | Glu | Phe | Leu | Glu | His | Arg | Arg | Arg | Phe | Gly | Asn | Thr |      |
|     |     |     | 980 |     |     |     |     | 985 |     |     |     |     | 990 |     |     |      |
| tct | gcg | ctg | gat | gat | cgt | gaa | ttc | ttc | tac | ggc | ctg | gtc | gaa | ggc | cgc | 3024 |

```
Ser Ala Leu Asp Asp Arg Glu Phe Phe Tyr Gly Leu Val Glu Gly Arg
            995                 1000                1005 gag act ttg atc cgc ctg cca gat gtg cgc acc cca ctg ctt gtt      3069
Glu Thr Leu Ile Arg Leu Pro Asp Val Arg Thr Pro Leu Leu Val
    1010                1015                1020 cgc ctg gat gcg atc tcc gag cca gac gat aag ggt atg cgc aat      3114
Arg Leu Asp Ala Ile Ser Glu Pro Asp Asp Lys Gly Met Arg Asn
    1025                1030                1035 gtt gtg gcc aac gtc aac ggc cag atc cgc cca atg cgt gtg cgt      3159
Val Val Ala Asn Val Asn Gly Gln Ile Arg Pro Met Arg Val Arg
    1040                1045                1050 gac cgc tcc gtt gag tct gtc acc gca acc gca gaa aag gca gat      3204
Asp Arg Ser Val Glu Ser Val Thr Ala Thr Ala Glu Lys Ala Asp
    1055                1060                1065 tcc tcc aac aag ggc cat gtt gct gca cca ttc gct ggt gtt gtc      3249
Ser Ser Asn Lys Gly His Val Ala Ala Pro Phe Ala Gly Val Val
    1070                1075                1080 act gtg act gtt gct gaa ggt gat gag gtc aag gct gga gat gca      3294
Thr Val Thr Val Ala Glu Gly Asp Glu Val Lys Ala Gly Asp Ala
    1085                1090                1095 gtc gca atc atc gag gct atg aag atg gaa gca aca atc act gct      3339
Val Ala Ile Ile Glu Ala Met Lys Met Glu Ala Thr Ile Thr Ala
    1100                1105                1110 tct gtt gac ggc aaa atc gat cgc gtt gtg gtt cct gct gca acg      3384
Ser Val Asp Gly Lys Ile Asp Arg Val Val Val Pro Ala Ala Thr
    1115                1120                1125 aag gtg gaa ggt ggc gac ttg atc gtc gtc gtt tcc taa              3423
Lys Val Glu Gly Gly Asp Leu Ile Val Val Val Ser
    1130                1135                1140

<210> SEQ ID NO 16
<211> LENGTH: 1140
<212> TYPE: PRT
<213> ORGANISM: Brevibacterium flavum

<400> SEQUENCE: 16

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175
```

```
Gly Met Arg Phe Val Ser Ser Pro Asp Glu Leu Arg Lys Leu Ala Thr
            180                 185                 190
Glu Ala Ser Arg Glu Ala Glu Ala Ala Phe Gly Asp Gly Ser Val Tyr
        195                 200                 205
Val Glu Arg Ala Val Ile Asn Pro Gln His Ile Glu Val Gln Ile Leu
    210                 215                 220
Gly Asp Arg Thr Gly Glu Val Val His Leu Tyr Glu Arg Asp Cys Ser
225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
            260                 265                 270
Cys Arg Ser Ile Gly Tyr Gln Gly Ala Gly Thr Val Glu Phe Leu Val
        275                 280                 285
Asp Glu Lys Gly Asn His Val Phe Ile Glu Met Asn Pro Arg Ile Gln
    290                 295                 300
Val Glu His Thr Val Thr Glu Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Thr His Gly Ala Ala Leu Gln Cys Arg Ile
            340                 345                 350
Thr Thr Glu Asp Pro Asn Asn Gly Phe Arg Pro Asp Thr Gly Thr Ile
        355                 360                 365
Thr Ala Tyr Arg Ser Pro Gly Gly Ala Gly Val Arg Leu Asp Gly Ala
    370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
        435                 440                 445
Ile Ala Thr Gly Phe Ile Gly Asp His Pro His Leu Leu Gln Ala Pro
    450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Thr Phe Arg Asp Ala
    530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
```

-continued

Asp Pro Trp Asp Arg Leu Asp Glu Leu Arg Glu Ala Met Pro Asn Val
595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
690                 695                 700

Ser Gly Ala His Ile Leu Ala Ile Lys Asp Met Ala Gly Leu Leu Arg
705                 710                 715                 720

Pro Ala Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Ala Asp Ala Val Asp Gly Ala
                755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
                980                 985                 990

Ser Ala Leu Asp Asp Arg Glu Phe Phe Tyr Gly Leu Val Glu Gly Arg
                995                 1000                1005

Glu Thr Leu Ile Arg Leu Pro Asp Val Arg Thr Pro Leu Leu Val

-continued

| | 1010 | | | | 1015 | | | | 1020 | | | |
|---|---|---|---|---|---|---|---|---|---|---|---|---|
| Arg | Leu | Asp | Ala | Ile | Ser | Glu | Pro | Asp | Asp | Lys | Gly | Met | Arg | Asn |
| | 1025 | | | | | 1030 | | | | 1035 | | | |
| Val | Val | Ala | Asn | Val | Asn | Gly | Gln | Ile | Arg | Pro | Met | Arg | Val | Arg |
| | 1040 | | | | | 1045 | | | | 1050 | | | |
| Asp | Arg | Ser | Val | Glu | Ser | Val | Thr | Ala | Thr | Ala | Glu | Lys | Ala | Asp |
| | 1055 | | | | | 1060 | | | | 1065 | | | |
| Ser | Ser | Asn | Lys | Gly | His | Val | Ala | Ala | Pro | Phe | Ala | Gly | Val | Val |
| | 1070 | | | | | 1075 | | | | 1080 | | | |
| Thr | Val | Thr | Val | Ala | Glu | Gly | Asp | Glu | Val | Lys | Ala | Gly | Asp | Ala |
| | 1085 | | | | | 1090 | | | | 1095 | | | |
| Val | Ala | Ile | Ile | Glu | Ala | Met | Lys | Met | Glu | Ala | Thr | Ile | Thr | Ala |
| | 1100 | | | | | 1105 | | | | 1110 | | | |
| Ser | Val | Asp | Gly | Lys | Ile | Asp | Arg | Val | Val | Val | Pro | Ala | Ala | Thr |
| | 1115 | | | | | 1120 | | | | 1125 | | | |
| Lys | Val | Glu | Gly | Gly | Asp | Leu | Ile | Val | Val | Val | Ser | | | |
| | 1130 | | | | | 1135 | | | | 1140 | | | |

BIOMASS-RESOURCE-DERIVED POLYESTER AND PRODUCTION PROCESS THEREOF

TECHNICAL FIELD

The present invention relates to a biomass-resource-derived polyester having a diol unit and a dicarboxylic acid unit as a constituent unit, and a production process of the polyester.

BACKGROUND ART

In today's society, paper, plastics, aluminum foils and the like have been used widely as packaging materials of various foods, medicines, sundry goods and the like in the form of liquid, powder or solid, agricultural materials and building materials. In particular, plastics have been used in many applications such as bags and containers owing to their excellent strength, water resistance, moldability or formability, transparency, cost and the like. Plastics used for such applications now are, for example, polyethylene, polypropylene, polystyrene, polyvinyl chloride and polyethylene terephthalate. However, molded products made of these plastics are neither biodegraded nor hydrolyzed under natural environments, or have their markedly low decomposition rate, they may remain in the soil when buried therein or spoil a view when discarded after use. Even if they are incinerated, they may pose a problem such as emission of a harmful gas or damage to the incinerator.

A number of researches have been carried out on materials that are biodegradable into a carbon dioxide gas and water by microorganisms in the soil or water as a means for solving the above-described problems. Typical examples of the biodegradable materials include aliphatic polyester resins such as polylactic acid, polybutylene succinate, and polybutylene succinate adipate and aromatic-aliphatic copolymer polyester resins such as polybutylene adipate terephthalate.

Of these, polylactic acid is one of the most typical polyesters but for it, an extremely low biodegradation rate is a big problem (Non-patent Document 1). Polybutylene succinate, polybutylene succinate adipate and the like having similar mechanical properties to those of polyethylene are, on the other hand, aliphatic polyesters having a relatively high biodegradation rate. They are advantageous in that molded products of them after use can be easily biodegraded or they easily compost. Their biodegradation rate is however not sufficiently high and a means for controlling their rate has not yet been developed.

Such polyesters are now produced by making use of polycondensation of raw materials derived from fossil fuel resources. In view of concerns about depletion of fossil fuel resources or an increase in carbon dioxide in the air that poses a global-scale environmental problem in recent years, methods for producing raw materials of these polymers from biomass resources have attracted attentions. Since these resources are renewable carbon-neutral biomasses, such methods are expected to gain in particular importance in future.

There have heretofore been developed technologies for preparing a dicarboxylic acid such as succinic acid or adipic acid from glucose, dextrose, cellulose, or oil or fat derived from biomass resources by using the fermentation process (refer to Patent Document 1, Non-patent Documents 1, 2 and 3).

These processes however provide a target dicarboxylic acid by preparing an organic acid salt of the dicarboxylic acid through fermentation and then subjecting it to steps such as neutralization, extraction and crystallization. Many impurities such as nitrogen elements derived from fermentation microorganisms, ammonia and metal cations, as well as nitrogen elements contained in the biomass resources, are therefore biomass-resource-derived polyester (Patent Document 2).

Non-Patent Document: *Expected Materials on the Future*, Vol. 1, No. 11, p 31(2001)

Patent Document 1: Japanese Patent Laid-Open No. 2005-27533

Non-Patent Document 2: Biotechnology and Bioengineering Symp. No. 17(1986), 355-363

Non-Patent Document 3: Journal of the American Chemical Society No. 116(1994), 399-400

Non-Patent Document 4: Appl. Microbiol Biotechnol No. 51 (1999), 545-552

Patent Document 2: Japanese Patent Laid-Open No. 2005-139287

DISCLOSURE OF THE INVENTION

Problem that the Invention is to Solve

The above-described biomass-resource-derived dicarboxylic acid or dial containing many impurities is typically used after subjected to purification treatment for reducing its purity content. The present inventors have found that even the dicarboxylic acid or diol subjected to purification treatment contains nitrogen elements derived from microorganisms or enzymes, or nitrogen elements such as ammonia, sulfur elements, inorganic acids, organic acids and metal cations used in the purification step, as well as nitrogen elements contained in the biomass resources, so that a polyester obtained using such a dicarboxylic acid component and/or diol component derived from biomass resources as raw materials is not satisfactory in properties including hydrolysis resistance and therefore has difficulty in molding due to marked hydrolysis of the polymer during storage. It has been revealed by the study of the present inventors that the polyester disclosed in Patent Document 2, on the other hand, is accompanied with the problem that owing to a nitrogen content of the polyester as high as 44 ppm, the polyester contains a large amount of terminal carboxylic acid groups so that it lacks stability and it tends to generate foreign matters during molding.

An object of the present invention is therefore to provide, when a dicarboxylic acid component and/or diol component derived from biomass resources are used as raw materials, a biomass-resource-derived polyester containing a specific amount of terminal acid groups and capable of suppressing marked hydrolysis.

Means for Solving The Problems

The present inventors have carried out an extensive investigation with a view to overcoming the above-described problems. As a result, it has been found that when a dicarboxylic acid and/or dial derived from biomass resources are used as raw materials for a polyester, hydrolysis of the polyester due to water contained therein is accelerated remarkably by the impurities contained in the raw materials and a marked deterioration in mechanical properties of the polyester such as tensile tension occurs after storage. It has also been found that these problems can be overcome by storing the polyester after reducing the amount of a specific impurity therein to adjust the amount of a terminal acid group in the polyester to 50 equivalents/metric ton or less, leading to the completion of the present invention.

The subject-matters of the present invention will next be described.

(1) A biomass-resource-derived polyester comprising as a main repeating unit thereof a dicarboxylic acid unit and a dial unit, wherein at least one of the dicarboxylic acid and dial used as raw materials of the polyester is obtained from biomass resources and an amount of terminal acid in the polyester is 50 equivalents/metric ton or less.

(2) The biomass-resource-derived polyester as described above in (1), wherein the reduced viscosity (ηsp/c) of the polyester is 1.0 or greater.

(3) The biomass-resource-derived polyester as descried above in (1) or (2), wherein the water content in the polyester is, in terms of a mass ratio, 1 ppm or greater but not greater than 3000 ppm relative to the polyester.

(4) The biomass-resource-derived polyester as described above in any one of (1) to (3), wherein the YI value of the polyester is −10 or greater but not greater than 30.

(5) The biomass-resource-derived polyester as described above in any one of (1) to (4), wherein a nitrogen atom content in the polyester except nitrogen atoms contained in the covalently bonded functional group in the molecule of the polyester is, in terms of a mass ratio, 0.01 ppm or greater but not greater than 1000 ppm relative to the polyester.

(6) The biomass-resource-derived polyester as described above in any one of (1) to (5), wherein a sulfur atom content in the polyester is, in terms of a mass ratio, 0.0001 ppm or greater but not greater than 50 ppm relative to the polyester.

(7) The biomass-resource-derived polyester as described above in any one of (1) to (6), which comprises at least one tri- or higher functional compound unit selected from the group consisting of tri- or higher functional polyhydric alcohols, tri- or higher functional polycarboxylic acids, and tri- or higher functional oxycarboxylic acids.

(8) The biomass-resource-derived polyester as described above in (7), wherein the content of the tri- or higher functional compound unit is 0.0001 mole % or greater but units constituting the polyester.

(9) The biomass-resource-derived polyester as described above in any one of (1) to (6), wherein the dicarboxylic acid unit constituting the main repeating unit of the polyester is a biomass-resource-derived succinic acid unit.

(10) A process for producing a biomass-resource-derived polyester by reaction of a dicarboxylic acid and a dial, wherein at least one of the dicarboxylic acid as raw material and dial as raw material provided for the reaction is derived from biomass resources; a nitrogen atom content in the dicarboxylic acid as raw material and dial as raw material is, in terms of a mass ratio, 0.01 ppm or greater but not greater than 2000 ppm relative to the total amount of the raw materials; and the polyester has an amount of terminal acid of 50 equivalents/metric ton or less.

(11) A process for producing a biomass-resource-derived polyester by reaction of a dicarboxylic acid and a diol, wherein at least one of the dicarboxylic acid as a raw material and diol as raw material provided for the reaction is derived from biomass resources; and a sulfur atom content in the dicarboxylic acid as raw material and diol as raw material is, in terms of a mass ratio, 0.1 ppm or greater but not greater than 100 ppm relative to the total amount of the raw materials.

(12) The process for producing a biomass-resource-derived polyester as described above in (11), wherein the nitrogen atom content in the dicarboxylic acid as raw material and/or diol as raw material is, in terms of a mass ratio, 0.01 ppm or greater but not greater than 2000 ppm relative to the total amount of the raw materials.

(13) The process for producing a biomass-resource-derived polyester as described above in any one of (10) to (12), wherein the reaction is preformed in the presence of at least one tri- or higher functional compound selected from the group consisting of tri- or higher functional polyhydric alcohols, tri- or higher functional polycarboxylic acids and tri- or higher functional oxycarboxylic acids.

(14) A biomass-resource-derived polyester obtained by the process as described above in any one of (10) to (13).

(15) A biomass-resource-derived polyester resin composition, which comprises 99.9 to 0.1 wt. % of a polyester as described above in any one (1) to (9) and (14) and 0.1 to 99.9 wt. % of a thermoplastic resin, biodegradable resin, natural resin or polysaccharide.

(16) A molded product obtained by molding a biomass-resource-derived polyester as described above in any one of (1) to (9) and (14).

(17) A molded product obtained by molding a polyester resin composition as described above in (15).

(18) A pellet obtained from a biomass-resource-derived polyester as described above in any one of (1) to (9) and (14).

Advantages of the Invention

The present invention makes it possible to provide, when a dicarboxylic acid and/or a dial derived from biomass resources is used as raw materials, a polyester capable of suppressing hydrolysis which will otherwise be accelerated by impurities contained therein and decreasing deterioration in mechanical properties such as tensile elongation. In addition, development of this method contributes greatly to the resolution of environmental problems and depletion problems of fossil fuel resources, whereby resins having practically effective physical properties can be obtained. In particular, since a dial unit or dicarboxylic acid unit obtained from natural materials vegetated under the earth's environment in the present atmosphere by the fermentation process or the like is used as a monomer of the polyester, raw materials are available at a very low cost. The production areas of plant as raw materials are not limited but dispersed, which secures a very stable supply of raw materials. In addition, the plant as raw materials are produced under the earth's environment in the atmosphere so that a relatively good mass balance is achieved between absorption and release of carbon dioxide. Moreover, the polyester can be recognized as a very eco-friendly and safe one. Such a polyester according to the present invention is not only excellent in physical properties, structure and function of the materials but also has a merit that it has a potential possibility of actualizing a recycling society which cannot be expected from fossil-fuel-derived polyesters. The present invention provides a polyester production process which has a new perspective different from that of the conventional fossil-fuel-dependent polyester so that it will contribute greatly to the utilization and growth of plastic materials from an utterly new viewpoint that it is a new second-stage plastic. The polyester of the present invention emits neither harmful substance nor offensive odor even if disposal in soil is replaced by incineration.

BEST MODE FOR CARRYING OUT THE INVENTION

Figure 1:
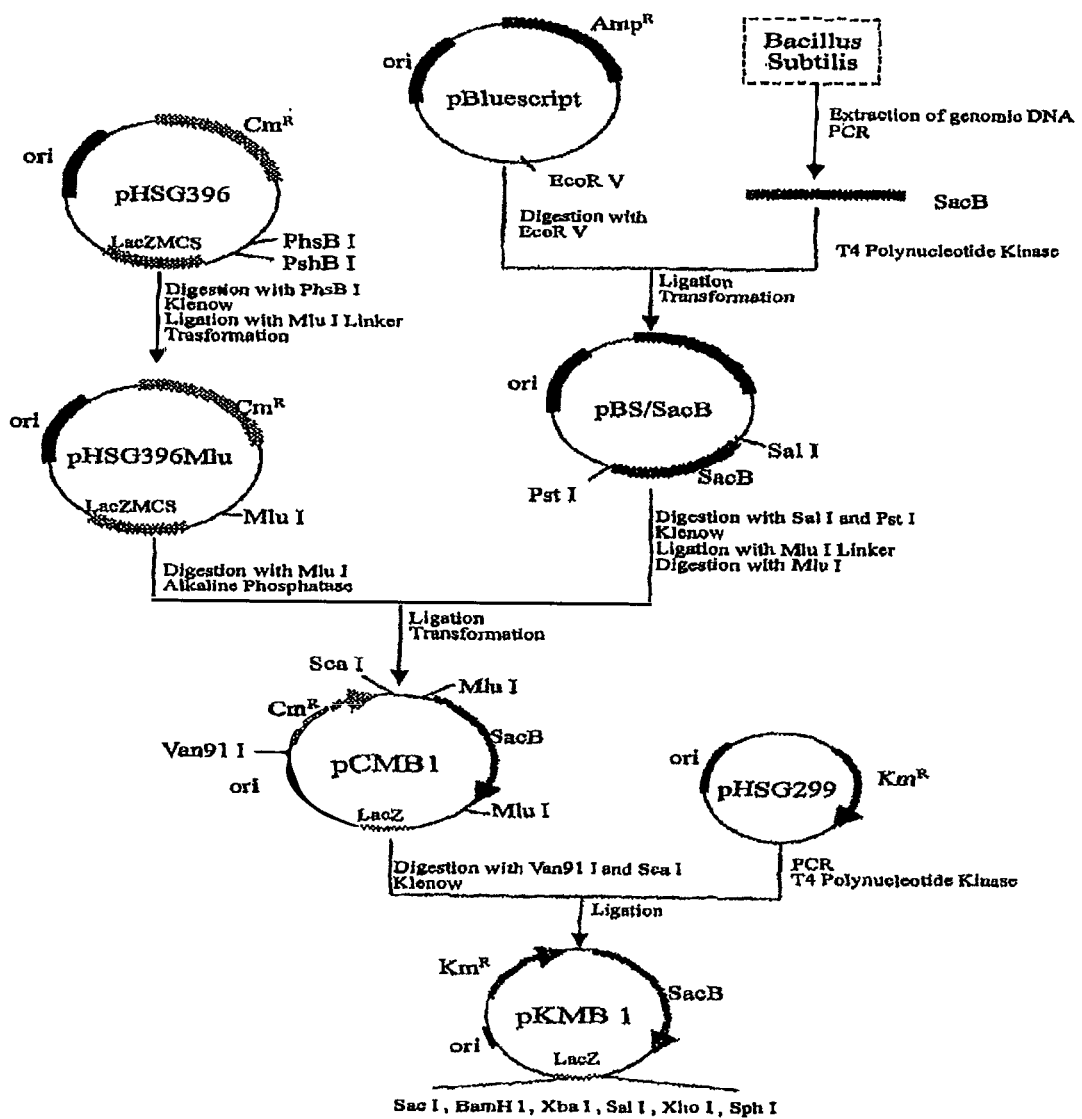
FIG. 1 schematically illustrates the construction of pKMB1.

The present invention will hereinafter be described specifically.
<Polyester>

The polyester which is a target of the present invention has a dicarboxylic acid unit and a dial unit as essential components. In the present invention, at least either one of dicarboxylic acid or dial constituting the dicarboxylic acid unit or dial unit, respectively, is preferably derived from biomass resources.

Dicarboxylic Acid Unit

Examples of the dicarboxylic acid constituting the dicarboxylic acid unit include aliphatic dicarboxylic acids or mixtures thereof, aromatic dicarboxylic acids or mixtures thereof, and mixtures of aromatic dicarboxylic acid and aliphatic dicarboxylic acid. Of these, dicarboxylic acids having, as a main component thereof, an aliphatic dicarboxylic acid are preferred. The term "main component" as used herein means that the component is contained in an amount of typically 50 mole % or greater, preferably 60 mole % or greater, more preferably 70 mole % or greater, especially preferably 90 mole % or greater based on the whole dicarboxylic acid unit.

Examples of the aromatic dicarboxylic acids include terephthalic acid and isophthalic acid. Examples of the derivatives of the aromatic dicarboxylic acid include lower alkyl esters of an aromatic dicarboxylic acid, more specifically, methyl ester, ethyl ester, propyl ester and butyl eater of an aromatic dicarboxylic acid. Of these, terephthalic acid is preferred as the aromatic dicarboxylic acid and dimethyl terephthalate is preferred as the derivative of an aromatic dicarboxylic acid. Even when an aromatic dicarboxylic acid as disclosed herein is used, a desired aromatic polyester, for example, a polyester of dimethyl terephthalate and 1,4-butanediol is available by using an arbitrary aromatic dicarboxylic acid.

As the aliphatic dicarboxylic acid, aliphatic dicarboxylic acids or derivatives thereof are used. Specific examples of the aliphatic dicarboxylic acid include linear or alicyclic dicarboxylic acids having typically 2 or greater but not greater than 40 carbon atoms such as oxalic acid, succinic acid, glutaric acid, adipic acid, sebacic acid, dodecanedioic acid, dimer acid and cyclohexanedicarboxylic acid. As the derivative of the aliphatic dicarboxylic acid, lower alkyl esters of the aliphatic dicarboxylic acid such as methyl ester, ethyl eater, propyl ester and butyl ester of the aliphatic dicarboxylic acid and cyclic acid anhydrides of the aliphatic dicarboxylic acid such as succinic anhydride are usable. Of these, adipic acid, succinic acid, and diner acid and mixtures thereof are preferred as the aliphatic dicarboxylic acid from the viewpoint of the physical properties of the polymer thus available, with the aliphatic dicarboxylic acids having succinic acid as a main component being especially preferred.

As the derivative of the aliphatic dicarboxylic acid, methyl adipate and methyl succinate, and mixture thereof are more preferred.

These dicarboxylic acids may be used either singly or as a mixture of two or more thereof.

In the present invention, these dicarboxylic acids are preferably derived from biomass resources.

The term "biomass resources" as used herein embraces resources in which the energy of sunlight has been stored in the form of starches or celluloses by the photosynthesis of plants; animal bodies which have grown by eating plant bodies; and products available by processing the plant bodies or animal bodies. Of these, plant resources are more preferred as biomass resources. Examples include wood, paddy straws, rice husks, rice bran, long-stored rice, corn, sugarcanes, cassava, sago palms, bean curd refuses, corn cobs, tapioca wastes, bagasse, plant oil wastes, potatoes, buckwheats, soybeans, oils or fats, used paper, residues after paper manufacture, residues of marine products, livestock excrement, sewage sludge and leftover food. Of these, wood, paddy straws, rice husks, rice bran, long-stored rice, corn, sugarcanes, cassava, sago palms, bean curd refuses, corn cobs, tapioca wastes, bagasse, plant oil wastes, potatoes, buckwheats, soybeans, oils or fats, used paper, and residues after paper manufacture are preferred, with wood, paddy straws, rice husks, long-stored rice, corn, sugarcanes, cassava, sago palms, potatoes, oils or fats, used paper, and residues after paper manufacture being more preferred. Corn, sugarcanes, cassava and sago palms are most preferred. These biomass resources typically contain a nitrogen element, and many alkali metals and alkaline earth metals such as Na, K, Mg and Ca.

These biomass resources are transformed into carbon sources after, not particularly limited to, known pretreatment and glycosylation steps such as chemical treatment with acids or alkalis, biological treatment with microorganisms and physical treatment. This step typically includes, but not particularly limited to, a miniaturization step by pretreatment to make biomass resources into chips, or shave or grind them. It includes if necessary a pulverization step in a grinder or mill. The biomass resources thus miniaturized are converted into carbon sources after the pretreatment and glycosylation steps. Specific examples of the pretreatment and glycosylation methods include chemical methods such as hydrochloric acid or phosphoric acid, alkali treatment, ammonia freeze explosion treatment, solvent extraction, supercritical fluid treatment and treatment with an oxidizing agent; physical methods such as fine grinding, steam explosion treatment, treatment with microwaves and exposure to electron beam; and biological treatment such as hydrolysis with microorganisms or enzymatic treatment.

As the carbon sources derived from the above-described biomass resources, typically used are fermentable carbohydrates such as hexoses such as glucose, mannose, galactose, fructose, sorbose and tagatose; pentoses such as arabinose, xylose, ribose, xylulose and ribulose; disaccharides and polysaccharides such as pentosan, saccharose, starch and cellulose; oils or fats such as butyric acid, caproic acid, caprylic acid, capric acid, lauric acid, myristic acid, palmitic acid, palmitoleic acid, stearic acid, oleic acid, linoleic acid, linolenic acid, monocutinic acid, arachic acid, eicosenoic acid, arachidonic acid, behenic acid, erucic acid, docosapentaenoic acid, docosahexaenoic acid, lignoceric acid, and ceracoreic acid; and polyalcohols such as glycerin, mannitol, xylitol And ribitol. Of these, glucose, fructose and xylose are preferred, with glucose being especially preferred. As carbon sources derived from plant resources in a broad sense, celluloses, a main component of paper, are preferred.

A dicarboxylic acid is synthesized using the above-described carbon sources in accordance with the fermentation process utilizing microbial conversion, a chemical conversion process including a reaction step such as hydrolysis, dehydration, hydration or oxidation, or a combination of the fermentation process and chemical conversion process. Of these, the fermentation process utilizing microbial conversion is preferred.

No particular limitation is imposed on the microorganism used for microbial conversion insofar as it has a producing capacity of a dicarboxylic acid. Examples of the microorganism include anaerobic bacteria such as those belonging to the genus *Anaerobiospirillum* (U.S. Pat. No. 5,143,833), facultative anaerobic bacteria (*E. coli* (J. Bacteriol., 57: 147-158) such as those belonging to the genus *Actinobacillus* (U.S. Pat. No. 5,504,004) and the genus *Escherichia* (U.S. Pat. No. 5,770,435), or *E. coli* mutant (International Patent Publication No. 2000-500333, U.S. Pat. No. 6,159,736 or the like), aerobic bacteria such as those belonging to the genus *Corynebacterium* (Japanese Patent Laid-open No. Hei 11-113588), aerobic bacteria (Japanese Patent Laid-Open No. 2003-235593) such as those belonging to the genus *Bacillus*, genus *Rizobium*, genus *Brevibacterium* or genus *Arthrobacter*, and anaerobic rumen bacteria such as Bacteroidesruminicola and Bacteroidesamylophilus. The above-described references are incorporated herein by reference.

More specifically, as the parent strain of the bacteria usable in the present invention, coryneform bacteria, *bacillus* bacteria and *rhizobium* bacteria are preferred, with coryneform bacteria being more preferred. These bacteria have a producing capacity of succinic acid by making use of microbial conversion.

Examples of the coryneform bacteria include microorganisms belonging to the genus *Corynebacterium*, microorganisms belonging to the genus *Brevibacterium* and microorganisms belonging to the genus *Arthrobacter*, with those belonging to the genus *Corynebacterium* and those belonging to the genus *Brevibacterium* being preferred. More preferred are microorganisms belonging to *Corynebacterium glutamicum*, *Brevibacterium flavum*, *Brevibacterium ammoniagenes* and *Brevibacterium lactofermentum*.

Especially preferred specific examples of the parent strain of the above-described bacteria include *Brevibacterium flavum* MJ-233 (FIRM BP-1497), *Brevibacterium flavum* MJ-233 AB-41 (FERM BP-1498), *Brevibacterium ammoniagenes* ATCC6872, *Corynebacterium glutamicum* ATCC31831, and *Brevibacterium lactofermentum* ATCC13869. Since *Brevibacterium flavum* is sometimes classified as *Corynebacteria glutamicum* (Lielbl, W., Ehrmann, M., Ludwig, W. and Schleifer, K. H., *International Journal of Systematic Bacteriology*, 1991, vol. 41, p 255-260), *Brevibacterium flavum* MJ-233 strain and its mutant MJ-233 AB-41 strain are regarded in the present invention to be equal to *Corynebacterium glutamicum* MJ-233 strain and MJ-233 AB-41 strain, respectively.

*Brevibacterium flavum* MJ-233 was deposited as accession number FERM P-3068, on Apr. 28, 1975, with the National Institute of Bioscience and Human-Technology, Agency of Industrial Science and Technology, Ministry of International Trade and Industry (present Patent Microorganism Depositary Center, National Institute of Advanced Industrial Science and Technology) (Center 6, 1-1, Higashi 1-chose, Tsukuba-shi, Ibaraki-ken, 305-8566 Japan) and was transferred to international deposition under the Budapest Treaty on May 1, 1981, and Deposit No. FERM BP-1497 was allotted thereto.

*Brevibacterium flavum* MJ-233-AB-41 was deposited as accession number FERM P-3812, on Nov. 17, 1976, with the National Institute of Bioscience and Human-Technology, Agency International Trade and Industry (present Patent Microorganism Depositary Center, National Institute of Advanced Industrial Science and Technology (Center 6, 1-1, Higashi 1-chome, Tsukuba-shi, Ibaraki-ken, 305-8566 Japan), and was transferred to international deposition under the Budapest Treaty on May 1, 1901, and Deposit No. FERM BP-1498 was allotted thereto.

Reaction conditions in the microbial conversion such as reaction temperature and pressure are determined, depending on the activity of microorganisms such as bacteria and fungi selected. Suitable conditions for obtaining a dicarboxylic acid may be selected as needed.

In the microbial conversion, a decrease in pH may deteriorate metabolic activity of microorganisms or stop the activity of microorganisms, which results in reduction in production yield or death of the microorganisms. Usually, a neutralizing agent is therefore employed. The pH in the reaction system is usually measured using a pH sensor and it is adjusted to fall within a predetermined pH range by the addition of the neutralizing agent. No particular limitation is imposed on the adding method of the neutralizing agent and it may be continuous addition or intermittent addition.

Examples of the neutralizing agent include ammonia, ammonium carbonate, urea, hydroxides of an alkali metal, hydroxides of an alkaline earth metal, carbonates of an alkali metal, and carbonates of an alkaline earth metal. Of these, ammonia, ammonium carbonate and urea are preferred. The hydroxides of an alkali (alkaline earth) metal include NaOH, KOH, $Ca(OH)_2$, and $Mg(OH)_2$ and mixtures thereof, while the carbonates of an alkali (alkaline earth) metal include $Na_2CO_3$, $K_2CO_3$, $CaCO_3$, $MgCO_3$, and $NaKCO_3$ and mixtures thereof.

The pH is adjusted to fall within a range in which each of the microorganisms such as bacteria and fungi can exhibit its activity most effectively. It is typically from pH 4 to 10, preferably from about 6 to 9.

As a method of purifying a dicarboxylic acid obtained by a production process including the fermentation process, there has been known a method using electrodialysis, a method using an ion exchange resin, and a salt exchange method. For example, a dicarboxylic acid may be purified using both electrodialysis and a water splitting step in combination for separating a dicarboxylate and thereby preparing a pure acid, followed by further purification by passing a product stream through a series of ion exchange columns or by using water splitting electrodialysis to convert into a supersaturated solution of a dicarboxylic acid (U.S. Pat. No. 5,034,105). As the salt exchange method, a dicarboxylic acid may be purified, for example, by mixing an ammonia salt of a dicarboxylic acid with ammonium hydrogen sulfate and/or sulfuric acid at a sufficiently low pH and causing a reaction between them to produce the corresponding dicarboxylic acid and ammonium sulfate (International Patent Publication No. 2001-514900). Specific methods using an ion exchange resin include a method of removing a solid content such as fungus body from a dicarboxylic acid solution by centrifugal separation, filtration or the like, desalting the resulting solution through an ion exchange resin, and separating and purifying the dicarboxylic acid from the solution by crystallization or column chromatography. Further purification methods include a method, as described in Japanese Patent Laid-Open No. Hei 3-30685, of carrying out fermentation while using calcium hydroxide as a neutralizing agent, removing a calcium sulfate precipitate formed by the addition of sulfuric acid, and then treating the residue with a strong acidic ion exchange resin and a weakly basic ion exchange resin; and a method, as described in Japanese Patent Laid-Open No. Hei 2-283289, of subjecting a succinate formed by the fermentation process to electrodialysis and then treating the product with a strongly acidic ion exchange resin and weakly basic ion exchange resin. Methods-described in U.S. Pat. No. 6,284,904 and Japanese Patent Laid-Open No. 2004-196760 are also preferred. In the present invention, any purification method may be used. A purified monomer as raw material suited for the present invention can be obtained by using, in any combination and if necessary in repetition, desired unit operations selected from those described in the above-described known literatures or Referential Examples of the present invention, for example, a method using electrodialysis, a method using an ion exchange resin, a method treating with an acid such as sulfuric acid, crystallization using water, alcohol, carboxylic acid or mixture thereof, washing, filtration and drying. Of these, an ion exchange method or salt exchange method is preferred from the viewpoints of cost and efficiency, of which the salt exchange method is especially preferred from the viewpoint of industrial productivity.

It is usually necessary to reduce the amount of impurities such as nitrogen compound and metal cation contained in the dicarboxylic acid by purification, thereby obtaining a practical polymer.

The dicarboxylic acid derived from biomass resources by the above-described process inevitably contains a nitrogen atom as an impurity. They are impurities from biomass resources themselves and those resulting from fermentation treatment and purification treatment including neutralization with an acid. More specifically, nitrogen atoms derived from amino acids, proteins, ammonium salts, urea, and fermentation microorganisms are contained in the dicarboxylic acid.

With regard to the nitrogen atom content in the dicarboxylic acid derived from the biomass resources by the above-described process, the upper limit is typically 2000 ppm or less, preferably 1000 ppm or less, more preferably 100 ppm or less, most preferably 50 ppm or less based on the mass of the dicarboxylic acid. The lower limit is typically 0.01 ppm or greater, preferably 0.05 ppm or greater. From the economical reason in the purification step, it is more preferably 0.1 ppm or greater, more preferably 1 ppm or greater, especially preferably 10 ppm or greater. Excessively great nitrogen atom contents tend to cause retardation of a polymerization reaction, an increase in the number of terminal carboxyl groups of the polymer thus produced, coloration, partial gelation and deterioration in stability. Although too low nitrogen atom contents are preferred, they are not advantageous economically because they may make the purification step complicated.

The nitrogen atom content is a value as measured by a known method such as elemental analysis or a method of separating an amino acid and ammonia from a sample under biogenic amino acid separating conditions and detecting it by ninhydrin colorimetry.

Use of the dicarboxylic acid having a nitrogen atom content falling within the above-described range is advantageous in reducing coloration of a polyester thus obtained. It is also effective for suppressing retardation of the polymerization reaction of the polyester.

Examples of a specific method for efficiently reducing the amount of ammonia contained as an impurity in the dicarboxylic acid include a reaction crystallization method using a weakly acidic organic acid having a higher pH than that of the target dicarboxylic acid.

When the dicarboxylic acid prepared by the fermentation process is used, it may contain a sulfur atom originating from the purification treatment including a neutralization step with an acid. Specific examples of the sulfur-atom-containing impurity include sulfuric acid, sulfates, sulfurous acid, organic sulfonic acids and organic sulfonates.

With regard to the sulfur atom content in the dicarboxylic acid, the upper limit is typically 100 ppm or less, preferably 20 ppm or less, more preferably 10 ppm or less, especially preferably 5 ppm or less, most preferably 0.5 ppm or less based on the mass of the dicarboxylic acid. The lower limit of it is, on the other hand, typically 0.001 ppm or greater, preferably 0.01 ppm or greater, more preferably 0.05 ppm or greater, especially preferably 0.1 ppm or greater. Excessively great sulfur atom contents tend to cause retardation of a polymerization reaction, partial gelation of the resulting polymer, an increase in the number of terminal carboxyl groups of the resulting polymer, and deterioration in stability. Although too low sulfur atom contents are preferred, they are not advantageous economically because they may make the purification step complicated. The sulfur atom content is a value as measured by known elemental analysis.

In the invention, when the biomass-resource-derived dicarboxylic acid obtained by the above-described process is used as a raw material for polyester, the oxygen concentration in a storage tank of the dicarboxylic acid to be connected to a polymerization system may be controlled to a predetermined value or less. By this control, coloration of the polyester, which will otherwise occur due to the oxidation reaction of nitrogen sources contained as an impurity, can be prevented.

A tank is typically employed for storing raw materials while controlling the oxygen concentration, but an apparatus other than a tank is also usable without particular limitation insofar as it can control the oxygen concentration. No specific limitation is imposed on the kind of the storage tank and known ones such as metal containers, metal containers having a glass or resin-lined inside, or containers made of glass or resin are usable. From the standpoint of strength, storage tanks made of a metal or those having a glass or resin lined inside are preferred. For the tank made of a metal, known materials are used. Specific examples include carbon steel, ferrite steel, martensitic stainless steels such as SUS 410, austenitic stainless steels such as SUS310, SUS304 and SUS316, clad steel, cast iron, copper, copper alloy, aluminum, inconel, hastelloy and titanium.

Although no particular limitation is imposed on the lower limit of the oxygen concentration in the storage tank of the dicarboxylic acid based on the total volume of the storage tank, it is typically 0.000011 or greater, preferably 0.01% or greater. The upper limit is on the other hand, 16% or less, preferably 14% or less, more preferably 12% or less. Too low oxygen concentrations are economically disadvantageous because they may make the equipment or control step complicated. Too high oxygen concentrations, on the other hand, tend to enhance the coloration of a polymer thus prepared.

With regard to the temperature of the dicarboxylic acid in the storage tank, the lower limit is typically −50° C. or greater, preferably 0° C. or greater. The upper limit is, on the other hand, typically 200° C. or less, preferably 100° C. or less, more preferably 50° C. or less. Storage at room temperature is most preferred because it does not need any temperature control. Too low temperatures tend to increase the storage cost, while too high temperatures tend to cause dehydration reaction or the like of the dicarboxylic acid simultaneously.

Although no particular limitation is imposed on the lower limit of the humidity in the storage tank of the dicarboxylic acid based on the total volume of the storage tank, it is typically 0.0001% or greater, preferably 0.001% or greater, more preferably 0.01% or greater, most preferably 0.1% or greater. The upper limit is 00% or less, preferably 60% or less, more preferably 40% or less. Too low humidities tend to be economically disadvantageous because the humidity control step becomes too complicated. Too high humidities tend to cause problems such as attachment of the dicarboxylic acid to the storage tank or pipes, blocking of the dicarboxylic acid and, if the storage tank is made of a metal, corrosion of the tank.

The pressure in the storage tank of the dicarboxylic acid is typically atmospheric pressure (normal pressure).

The dicarboxylic acid to be used in the present invention is preferably less colored typically. The upper limit of the yellowness (YI) of the dicarboxylic acid to be used in the present invention is typically 50 or less, preferably 20 or less, more preferably 10 or less, still more preferably 6 or less, especially preferably 4 or less. Although no particular limitation is imposed on the lower limit, it is typically −20 or greater, preferably −10 or greater, more preferably −5 or greater, especially preferably −3 or greater, most preferably −1 or greater. The polymer available from the dicarboxylic acid having a high YI has the drawback that it is highly colored. The dicarboxylic acid having a low YI is preferred, but use of it is economically disadvantageous because it needs a lot of time for its preparation as well as expensive equipment investment. In the present invention, the YI is a value determined by the measurement based on JIS K7105.

(2) Diol Unit

The term "diol unit" as used herein means a unit derived from aromatic diols and/or aliphatic diols. Known diol compounds are usable as them, but aliphatic diols are preferred.

Although no particular limitation is imposed on the aliphatic diol insofar as it is an aliphatic or alicyclic compound having two OH groups, examples of it include aliphatic dials having carbon atoms, as the lower limit thereof, of 2 or greater and, as the upper limit, of typically 10 or less, preferably 6 or less. Of these, diols having an even number of carbon atoms and mixtures thereof are preferred because polymers having a higher melting point are available from them.

Specific examples of the aliphatic dial include ethylene glycol, 1,3-propylene glycol, neopentyl glycol, 1,6-hexamethylene glycol, decamethylene glycol, 1,4-butanediol and 1,4-cyclohexanedimethanol. These may be used either singly or as a mixture of two or more of them.

Of these, ethylene glycol, 1,4-butanediol, 1,3-propylene glycol, and 1,4-cyclohexanedimethanol are preferred, of which ethylene glycol and 1,4-butanediol, and mixtures thereof are preferred. Furthermore, aliphatic diols having 1,4-butanediol as a main component thereof are more preferred, with 1,4-butanediol being especially preferred. The term "main component" as used herein means that it is contained in an amount of typically 50 sole % or greater, preferably 60 mole % or greater, more preferably 70 mole % or greater, especially preferably 90 mole % or greater based on all the dial units.

Although no particular limitation is imposed on the aromatic dial insofar as it is an aromatic compound having two OH groups, examples of it include, aromatic dials having 6 or greater carbon atoms as a lower limit and 15 or less carbon atoms as an upper limit. Specific examples of it include hydroquinone, 1,5-dihydroxynaphthalene, 4,4'-dihydroxydiphenyl, bis(p-hydroxyphenyl)methane and bis(p-hydroxyphenyl)-2,2-propane. The content of the aromatic diol in the total amount of all the diols is typically 30 mole % or less, preferably 20 mole % or leas, more preferably 10 mole % or less.

Furthermore, a both-hydroxy-terminated polyether (polyether having a hydroxyl at both terminals) may be used in combination with the above-described aliphatic diol. With regard to the number of carbon atoms of the both-hydroxy-terminated polyether, the lower limit is typically 4 or greater, preferably 10 or greater, while the upper limit is typically 1000 or less, preferably 200 or less, more preferably 100 or less.

Specific examples of the both-hydroxy-terminated polyether include diethylene glycol, triethylene glycol, polyethylene glycol, polypropylene glycol, polytetramethylene glycol, poly-1,3-propanediol and poly-1,6-hexamethylene glycol. Moreover, copolymer polyether between polyethylene glycol and polypropylene glycol, and the like can be also used. The using amount of the both-hydroxy-terminated polyether is typically 90 wt. % or less, preferably 50 wt. % or less, more preferably 30 wt. % or less in terms of a calculated content in the polyester.

In the present invention, these diols may be derived from biomass resources. More specifically, the diol compound may be prepared directly from carbon sources such as glucose by the fermentation process or it may be prepared by the conversion of a dicarboxylic acid, dicarboxylic anhydride or cyclic ether, which has been obtained by the fermentation process, by a chemical reaction.

For example, 1,4-butanediol may be prepared by a chemical reaction of succinic acid, succinic anhydride, succinate ester, maleic acid, maleic anhydride, maleate ester, tetrahydrofuran or γ-butyrolactone, or it may be prepared from 1,3-butadiene obtained by the fermentation process. Of these, a method of obtaining 1,4-butanediol by the hydrogenation of succinic acid in the presence of a reduction catalyst is efficient and is therefore preferred.

Examples of the catalyst to be used for hydrogenation of succinic acid include Pd, Ru, Re, Rh, Ni, Cu, and Co, and compounds thereof. Specific examples of it include Pd/Ag/Re, Ru/Ni/Co/ZnO, Cu/Zn oxide, Cu/Zn/Cr oxide, Ru/Re, Re/C, Ru/Sn, Ru/Pt/Sn, Pt/Re/alkali, Pt/Re, Pd/Co/Re, Cu/Si, Cu/Cr/Mn, ReO/CuO/ZnO, CuO/CrO, Pd/Re, Ni/Co, Pd/CuO/CrO$_3$, phosphoric acid-Ru, Ni/Co, Co/Ru/Mn, Cu/Pd/KOH and Cu/Cr/Zn. Of these, Ru/Sn and Ru/Pt/Sn are preferred because of their catalytic activity.

A process of preparing a dial compound from biomass resources by using known organic chemical catalytic reactions in combination is also used preferably. For example, when pentose is used as a biomass resource, a diol such as butane diol can easily be prepared by using known dehydration reaction and catalytic reaction in combination.

The diol derived from biomass resources sometimes contains a nitrogen atom as an impurity originating from the biomass resources themselves, fermentation treatment or purification treatment including a neutralization step with an acid. In this case, specifically, it contains a nitrogen atom derived from amino acids, proteins, ammonia, urea, and fermentation microorganisms.

With regard to the nitrogen atom content in the dial prepared by the fermentation process, the upper limit is typically 2000 ppm or less, preferably 1000 ppm or less, more preferably 100 ppm or less, most preferably 50 ppm or less based on the mass of the dial. Although no particular limitation is imposed on the lower limit, it is typically 0.01 ppm or greater, preferably 0.05 ppm or greater. From the viewpoint of the economy of the purification step, it is more preferably 0.1 ppm or greater, still more preferably 1 ppm or greater, especially preferably 10 ppm or greater. Excessively high contents tend to cause retardation of a polymerization reaction and an increase in the number of terminal carboxyl groups, coloration, partial gelation and deterioration in stability of the resulting polymer. Excessively low contents, on the other hand, are economically disadvantageous because they may make the purification step complicated.

In another mode, the upper limit of the nitrogen atom content in the dicarboxylic acid as raw material and diol is typically 2000 ppm or less, preferably 1000 ppm or less, more preferably 100 ppm or less, most preferably 50 ppm or less based on the total mass of the above-described raw materials. Although no particular limitation is imposed on the lower limit, it is typically 0.01 ppm or greater, preferably 0.05 ppm or greater, 0.1 ppm or greater.

When the diol prepared by the fermentation process is used, it may contain a sulfur atom originating from the purification treatment including neutralization step with an acid. Specific examples of the sulfur-containing impurity include sulfuric acid, sulfurous acid, and organic sulfonates.

With regard to the sulfur atom content in the diol, the upper limit is typically 100 ppm or less, preferably 20 ppm or less, more preferably 10 ppm or less, especially preferably 5 ppm or less, most preferably 0.5 ppm or less based on the mass of the diol. Although no particular limitation is imposed on the lower limit, it is typically 0.001 ppm or greater, preferably 0.01 ppm or greater, more preferably 0.05 ppm or greater, especially preferably 0.1 ppm or greater. Excessively great sulfur atom contents tend to cause retardation of a polymerization reaction and partial gelation, increase in the number of terminal carboxyl groups, and stability deterioration of the resulting polymer. Although too low sulfur atom contents are preferred, they are not advantageous economically because they may make the purification step complicated. The sulfur atom content is a value as measured by known elemental analysis.

In another mode, the upper limit of the sulfur atom content in the dicarboxylic acid as raw material and diol is, in terms of atoms, typically 100 ppm or less, preferably 20 ppm or less, more preferably 10 ppm or less, especially preferably 5 ppm or less, most preferably 0.5 ppm or less based on the total mass of the raw materials. Although no particular limitation is imposed on the lower limit, it is typically 0.001 ppm or greater, preferably 0.01 ppm or greater, more preferably 0.05 ppm or greater, especially preferably 0.1 ppm or greater.

In the present invention, when the biomass-resource-derived diol obtained by the above-described process is used as a raw material of a polyester, the oxygen concentration or temperature in a storage tank of the dial connected to a polymerization system may be controlled in order to suppress coloration of the polyester which will otherwise occur by the impurity. This control makes it possible to suppress the coloration of the impurity itself or oxidation reaction of the diol accelerated by the impurity. For example, when 1,4-butanediol is employed, coloration of a polyester due to an oxidation product of the dial such as 2-(4-hydroxybutyloxy)tetrahydrofuran can be prevented.

A tank is typically employed for storing raw materials while controlling the oxygen concentration, but any apparatus is usable without particular limitation insofar as it can control the oxygen concentration. No specific limitation is imposed on the kind of the storage tank and known ones such as those made of a metal, those made of a metal having a glass or resin-lined inside, or containers made of glass or resin are usable. From the standpoint of strength, storage tanks made of a metal or those having a glass or resin-lined inside are preferred. For the tanks made of a metal, known materials are used. Specific examples include carbon steel, ferrite steel, martensitic stainless steels such as SUS410, austenitic stainless steels such as SUS310, SUS304 and SUS316, clad steel, cast iron, copper, copper alloy, aluminum, inconel, hastelloy and titanium.

Although no particular limitation is imposed on the lower limit of the oxygen concentration in the storage tank of the diol based on the total volume of the storage tank, but it is typically 0.00001% or greater, preferably 0.0001% or greater, more preferably 0.001% or greater, most preferably 0.01% or greater. The upper limit is typically 10% or less, preferably 5% or less, more preferably 1% or less, most preferably 0.1% or less. Too low oxygen concentrations are economically disadvantageous because they may make the control step complicated. Too high oxygen concentrations, on the other hand, tend to enhance the coloration of the resulting polymer due to the oxidation reaction product of the diol.

The lower limit of the storage temperature in the storage tank of the diol is typically 15° C. or greater, preferably 30° C. or greater, more preferably 50° C. or greater, most preferably 100° C. or greater. The upper limit is 230° C. or less, preferably 200° C. or less, more preferably 180° C. or less, most preferably 160° C. or less. Too low temperatures are economically disadvantageous for polyester manufacture because it tends to take much time to raise the temperature at the time of polyester production and in addition, the diol sometimes solidifies. Too high temperatures, on the other hand, are not only economically disadvantageous because of necessity of high-pressure storage equipment but also tend to enhance deterioration of the diol.

The pressure in the storage tank of the dial is typically atmospheric pressure (normal pressure). Too high or too low pressures are economically disadvantageous because they make controlling equipment complicated.

In the present invention, the upper limit of the content, in the diol, of the oxidation product of the diol to be used for the production of a polymer having a good hue is typically 10000 ppm or less, preferably 5000 ppm or less, more preferably 3000 ppm or less, most preferably 2000 ppm or less. Although no particular limitation is imposed on the lower limit, it is typically 1 ppm or greater. Owing to economic reasons of the purification step, it is preferably 10 ppm or greater, more preferably 100 ppm or greater.

In the present invention, the diol is typically used as a raw material of a polyester after a purification step by distillation.

In the present invention, any polyesters produced by a reaction of components composed mainly of various compounds belonging to the above-described respective ranges of the dicarboxylic acid unit and dial unit are embraced in the polyester of the present invention. Following polyesters can be exemplified specifically as typical examples. Examples of the polyester produced using succinic acid include polyester composed of succinic acid and ethylene glycol, polyester composed of succinic acid and 1,3-propylene glycol, polyester composed of succinic acid and neopentyl glycol, polyester composed of succinic acid and 1,6-hexamethylene glycol, polyester composed of succinic acid and 1,4-butanediol, and polyester composed of succinic acid and 1,4-cyclohexanedimethanol.

Examples of the polyester produced using oxalic acid include polyester composed of oxalic acid and ethylene glycol, polyester composed of oxalic acid and 1,3-propylene glycol, polyester composed of oxalic acid and neopentyl glycol, polyester composed of oxalic acid and 1,6-hexamethylene glycol, polyester composed of oxalic acid and 1,4-butanediol, and polyester composed of oxalic acid and 1,4-cyclohexanedimethanol.

Examples of the polyester produced using adipic acid include polyester composed of adipic acid and ethylene glycol, polyester composed of adipic acid and 1,3-propylene glycol, polyester composed of adipic acid and neopentyl glycol, polyester composed of adipic acid and 1,6-hexamethylene glycol, polyester composed of adipic acid and 1,4-butanediol, and polyester composed of adipic acid and 1,4-cyclohexanedimethanol.

Polyesters obtained using the above-described dicarboxylic acid in combination are also preferred. Examples include polyester composed of succinic acid, adipic acid and ethylene glycol, polyester composed of succinic acid, adipic acid and 1,4-butanediol, polyester composed of terephthalic acid, adipic acid and 1,4-butanediol and polyester composed of terephthalic acid, succinic acid and 1,4-butanediol.

The present invention also embraces a copolymer polyester composed of, in addition to the diol component and dicarboxylic acid component, a copolymerizable component as a third component. As specific examples of the copolymerizable component, at least one polyfunctional compound selected from the group consisting of bifunctional oxycarboxylic acids and tri- or higher functional polyhydric alcohols, tri- or higher functional polycarboxylic acids and/or anhydrides thereof, and tri- or higher functional oxycarboxylic acids for forming a crosslinked structure. Of these copolymerizable components, bifunctional and/or tri- or higher functional oxycarboxylic acids are especially preferred because they facilitate preparation of a copolyester having a high degree of polymerization. Above all, use of a tri- or higher functional oxycarboxylic acid is most preferred because even a very small amount of it facilitates production of a polyester having a high degree of polymerisation without using a chain extender which will be described later.

Specific examples of the bifunctional oxycarboxylic acid include lactic acid, glycolic acid, hydroxybutyric acid, hydroxycaproic acid, 2-hydroxy-3,3-dimethylbutyric acid, 2-hydroxy-3-methylbutyric acid, 2-hydroxyisocaproic acid, and caprolactone. They may be derivatives of an oxycarboxylic acid such as esters or lactones of the oxycarboxylic acid and polymers of the oxycarboxylic acid. Moreover, these oxycarboxylic acids may be used either singly or as mixtures of two or more thereof. In the case where they have optical isomers, the optical isomers may be any of D-form, L-form, or racemic-form and they may be in the form of a solid, liquid, or aqueous solution. Of these, easily available lactic acid or glycolic acid is especially preferred. Lactic acid or glycolic acid in the form of a 30 to 95% aqueous solution is preferred because it is easily available. When a bifunctional oxycarboxylic acid is used as a copolymerizable component in order to produce a polyester having a high degree of polymerization, a desired copolyester can be obtained by the addition of any bifunctional oxycarboxylic acid during polymerization. The lower limit of the using amount at which it exhibits its effect is typically 0.02 mole % or greater, preferably 0.5 mole % or greater, more preferably 1.0 mole % or greater based on the raw material monomer. The upper limit of the using amount is, on the other hand, typically 30 mole % or less, preferably 20 mole % or less, more preferably 10 mole % or less.

Specific modes of the polyester includes, when lactic acid is used as the bifunctional oxycarboxylic acid, a succinic acid-1,4-butanediol-lactic acid copolyester and a succinic acid-adipic acid-1,4-butanediol-lactic acid copolyester; and when glycolic acid is used, a succinic acid-1,4-butanediol-glycolic acid copolyester.

Specific examples of the tri- or higher functional polyhydric alcohol include glycerin, trimethylolpropane and pentaerythritol. They may be used either singly or as a mixture of two or more thereof.

When pentaerythritol is used as the tri- or higher functional polyhydric alcohol as the copolymerizable component, a succinic acid-1,4-butanediol-pentaerythritol copolyester or a succinic acid-adipic acid-1,4-butanediol-pentaerythritol copolyester can be obtained. A desired copolyester can be produced by changing the tri- or higher functional polyhydric alcohol as needed. High molecular weight polyesters obtained by chain extension (coupling) of these copolyesters are also embraced in the polyester of the present invention.

Specific examples of the tri- or higher functional polycarboxylic acid or anhydride thereof include propanetricarboxylic acid, pyromellitic anhydride, benzophenonetetracarboxylic anhydride, and cyclopentatetracarboxylic anhydride. They may be used either singly or as a mixture of two or more thereof.

Specific examples of the tri- or higher functional oxycarboxylic acid include malic acid, hydroxyglutaric acid, hydroxymethylglutaric acid, tartaric acid, citric acid, hydroxyisophthalic acid, and hydroxyterephthalic acid. They may be used either singly or as a mixture of two or more thereof. Of these, malic acid, tartaric acid, and citric acid, and mixtures thereof are especially preferred because of easy availability. When malic acid is used as a trifunctional oxycarboxylic acid serving as the copolymerizable component, examples of the copolyester thus available include succinic acid-1,4-butanediol-malic acid copolyester, succinic acid-adipic acid-1,4-butanediol-malic acid copolyester, succinic acid-1,4-butanediol-malic acid-tartaric acid copolyester, succinic acid-adipic acid-1,4-butanediol-malic acid-tartaric acid copolyester, succinic acid-1,4-butanediol-malic acid-citric acid copolyester, and succinic acid-adipic acid-1,4-butanediol-malic acid-citric acid copolyester. A desired copolyester can be produced by changing the tri-functional oxycarboxylic acid as needed.

When a bifunctional oxycarboxylic acid is used in combination further, examples of the copolyester thus available include succinic acid-1,4-butanediol-malic acid-lactic acid copolyester, succinic acid-adipic acid-1,4-butanediol-malic acid-lactic acid copolyester, succinic acid-1,4-butanediol-malic acid-tartaric acid-lactic acid copolyester, succinic acid-adipic acid-1,4-butanediol-malic acid-tartaric acid-lactic acid copolyester, succinic acid-1,4-butanediol-malic acid-citric acid-lactic acid copolyester, and succinic acid-adipic acid-1,4-butanediol-malic acid-citric acid-lactic acid copolyester.

The upper limit of the amount of the tri- or higher functional compound unit is typically 5 mole % or less, preferably 1 mole % or less, still more preferably 0.50 mole % or less, especially preferably 0.3 mole % or less based on 100 mole % of all the monomer units constituting the polyester in order to avoid gelation. When a tri- or higher functional compound is used as a copolymerizable component for facilitating the production of a polyester having a high degree of polymerization, the lower limit of the using amount at which it exhibits its effect is typically 0.0001 mole % or greater, preferably 0.001 mole % or greater, more preferably 0.005 mole % or greater, especially preferably 0.01 mole % or greater.

For the production of the polyester of the present invention, a chain extender such as carbonate compound or diisocyanate compound can be used. The using amount of it is, in terms of a carbonate bond or urethane bond content, typically 10 mole % or less, preferably 5 mole % or less, more preferably 3 mole % or less based on all the monomer units constituting the polyester. When the polyester of the present invention is used as a biodegradable resin, a diisocyanate or carbonate bond present therein may inhibit the biodegradability so that it is used in the following amount based on all the monomer units constituting the polyester. The carbonate bond content is less than 1 mole %, preferably 0.5 mole % or less, more preferably 0.1 mole % or less, while the urethane bond content is less than 0.06 mole %, preferably 0.01 mole % or less, more preferably 0.001 mole % or less. The carbonate bond or urethane bond content can be determined by NMR measurement such as $^{13}C$ NMR.

Specific examples of the carbonate compound include diphenyl carbonate, ditolyl carbonate, bis(chlorophenyl) carbonate, m-cresyl carbonate, dinaphthyl carbonate, dimethyl carbonate, diethyl carbonate, dibutyl carbonate, ethylene carbonate, diamyl carbonate, and dicyclohexyl carbonate. In addition, carbonate compounds derived from hydroxy compounds, which may be the same or different, such as phenols and alcohols are also usable.

Specific examples of the diisocyanate compound include known diisocyanates such as 2,4-tolylene diisocyanate, a mixture of 2,4-tolylene diisocyanate and 2,6-tolylene diisocyanate, diphenylmethane diisocyanate, 1,5-naphthylene diisocyanate, xylylene diisocyanate, hydrogenated xylylene diisocyanate, hexamethylene diisocyanate, and isophorone diisocyanate.

Production of a high molecular weight polyester using the above-described chain extender (coupling agent) can be performed in a manner known per se in the art. After completion of the polycondensation, the chain extender is added under a homogeneous molten state to a reaction system in a solventless manner and is reacted with a polyester obtained by the polycondensation.

More specifically, a polyester resin having an increased molecular weight is available by reacting, with the above-described chain extender, a polyester which has been obtained by the catalytic reaction of the diol and the dicarboxylic acid (or anhydride thereof), has substantially a hydroxyl group as the terminal group, and has a weight average molecular weight (Mw) of 20,000 or greater, preferably 40,000 or greater. Owing to the use of a small amount of the coupling agent, the prepolymer having a weight-average molecular weight of 20,000 or greater is free from the influence of a remaining catalyst even under severe molten condition. As a result, a high molecular weight polyester can be produced without generating a gel during the reaction.

Accordingly, when the above-described diisocyanate, for example, is used as a chain extender for the purpose of increasing the molecular weight further, a polyester having a linear structure in which prepolymers each made of a diol and a dicarboxylic acid and having a weight average molecular weight of 20,000 or greater, preferably 40,000 or greater have been chained via a urethane bond derived from the diisocyanate is produced.

The pressure upon chain extension is typically 0.01 MPa or greater but not greater than 1 MPa, preferably 0.05 MPa or greater but not greater than 0.5 MPa, more preferably 0.07 MPa or greater but not greater than 0.3 MPa, with the normal pressure being most preferred.

With respect to the reaction temperature upon chain extension, the lower limit is typically 100° C. or greater, preferably 150° C. or greater, more preferably 190° C. or greater, most preferably 200° C. or greater, while the upper limit is typically 250° C. or less, preferably 240° C. or less, more preferably 230° C. or less. Too low reaction temperatures raise a viscosity and disturb homogeneous reaction. They sometimes tend to need a high stirring power. Too high reaction temperatures tend to cause gelation or decomposition of the polyester simultaneously.

With respect to the chain extension time, the lower limit is typically 0.1 minute or greater, preferably 1 minute or greater, more preferably 5 minutes or greater, while the upper limit is typically 5 hours or less, preferably 1 hour or less, more preferably 30 minutes or less, most preferably 15 minutes or less. Too short extension time tends to disturb the appearance of addition effect. Too long extension time, on the other hand, tends to cause gelation or decomposition of the polyester simultaneously.

As other chain extenders, dioxazoline and silicate esters are usable. Specific examples of the silicate esters include tetramethoxysilane, dimethoxydiphenylsilane, dimethoxydimethylsilane and diphenyldihydroxysilane.

Although no particular limitation is imposed on the using amount of the silicate ester from the standpoints of environmental preservation and safety, a small using amount is sometimes preferred in order to avoid the possibility of making the operation complicated or adversely affecting the polymerization rate. The content of the silicate ester is therefore preferably 0.1 mole % or less, more preferably $10^{-5}$ mole % or less based on all the monomer units constituting the polyester.

Thus, the term "polyester" as used herein is a generic name that collectively embraces polyesters, copolyesters, high molecular weight polyesters having chain-extended (coupled), and modified polyesters.

In the present invention, polyesters substantially free of a chain extender are preferred. A small amount of a peroxide may however be added in order to heighten the melt tension insofar as a compound having a low toxicity is added.

In the present invention, a terminal group of the polyester may be sealed with a carbodiimide, epoxy compound, a monofunctional alcohol or carboxylic acid.

As the carbodiimide compound, compounds (including polycarbodiimide compounds) having, in the molecule thereof, at least one carbodiimide group are unable. Specific examples include monocarbodiimide compounds such as dicyclohexylcarbodiimide, diisopropylcarbodiimide, dimethylcarbodiimide, diisobutylcarbodiimide, dioctylcarbodiimide, t-butylisopropylcarbodiimide, diphenylcarbodiimide, di-t-butylcarbodiimide, di-β-naphthylcarbodiimide and N,N'-di-2,6-diisopropylphenylcarbodiimide. As the polycarbodiimide compound, those having a degree of polymerization of typically 2 or greater, preferably 4 or greater, as the lower limit, and typically 40 or less, preferably 30 or less as the upper limit are used. Examples of them include those prepared by the process as described in U.S. Pat. No. 2,941,956; Japanese Patent Publication No. Sho 47-33279; *J. Org. Chem.* 28, 2069-2075 (1963); *Chemical Review* 1981, Vol. 81 No. 4, pp. 619-621, and the like.

Examples of the organic diisocyanate which is a raw material for the production of the polycarbodiimide compound include aromatic diisocyanates, aliphatic diisocyanates, and alicyclic diisocyanates, and mixtures thereof. Specific examples include 1,5-naphthalene diisocyanate, 4,4'-diphenylethane diisocyanate, 4,4'-diphenyldimethylmethane diisocyanate, 1,3-phenylene diisocyanate, 1,4-phenylene diisocyanate, 2,4-tolylene diisocyanate, 2,6-tolylene diisocyanate, a mixture of 2,4-tolylene diisocyanate and 2,6-tolylene diisocyanate, hexamethylene diisocyanate, cyclohexane-1,4-diisocyanate, xylylene diisocyanate, isophorone diisocyanate, 4,4'-dicyclohexylmethane diisocyanate, methylcyclohexane diisocyanate, tetramethylxylylene diisocyanate, 2,6-diisopropylphenyl isocyanate and 1,3,5-triisopropylbenzene-2,4-diisocyanate.

Specific examples of the industrially available polycarbodiimides include "CARBODILITE HMV-8CA" (product of Nisshinbo Industries), "CARBODILITE LA-1" (product of Nisshinbo Industries), "STABAXOL P" (product of Rhine Chemie), and "STABAXOL P100" (product of Rhine Chemie).

The carbodiimide compounds may be used either singly or as a mixture of a plurality of them.

<Production of Polyester>

A polyester composed mainly of a diol unit and a dicarboxylic acid unit can be produced in a manner known per as in the art in the production of polyesters. The polymerization reaction for producing polyesters can be carried out under conventionally employed appropriate conditions and no particular limitation is imposed on them. Described specifically, it can be produced by the ordinarily employed malt polymerization in which an esterification reaction and/or ester exchange reaction of the above-described dicarboxylic acid component and diol component, and the oxycarboxylic acid unit or tri- or higher functional component if it is introduced, is carried out, followed by a polycondensation reaction under reduced pressure; or by the known thermal dehydration condensation method in an organic solvent. From the standpoints of economy and simplicity of the production steps, melt polymerization in a solventless manner is preferred.

In the present invention, when the biomass-resource-derived dicarboxylic acid and/or diol prepared in the above-described manner is used as a raw material for a polyester, the polyester may be produced in a reaction tank whose oxygen concentration is controlled not to exceed a specific value during the polyester production reaction. This makes it possible to suppress coloration of the polyester which will otherwise occur by the oxidation reaction of a nitrogen compound contained as an impurity, or coloration of the polyester due to a reaction product of dial oxidation, for example, 2-(4-hydroxybutyloxy)tetrahydrofuran produced by the oxidation reaction of 1,4-butanediol when 1,4-butanediol is used as the diol. As a result, a polyester having a good hue can be produced.

The term "production reaction" as used herein defines a reaction from the starting of temperature elevation after raw materials are charged in an esterification tank to returning of the pressure of the reaction tank from reduced pressure to normal pressure or greater after preparation of a polymer having a desired viscosity under reduced pressure in a polycondensation tank.

No particular limitation is imposed on the lower limit of the oxygen concentration in the reaction tank during the production reaction, it is typically $1.0 \times 10^{-9}$% or greater, preferably $1.0 \times 10^{-7}$% or greater based on the total volume of the reaction tank. The upper limit is typically 10% or less, preferably 10 or less, more preferably 0.1% or less, most preferably 0.01% or less. Too low oxygen concentrations tend to make the controlling step complicated, while too high oxygen concentrations tend to color the polyester markedly because of the above-described reasons.

When the biomass-resource-derived dicarboxylic acid and/or diol obtained by the above-described process is used as a raw material of a polyester, a stirring rate prior to the termination of the polymerization reaction under reduced pressure may be controlled. This makes it possible to produce a biomass-resource-derived polyester which has been inhibited from decomposition and has a high viscosity.

The term "final stirring rate" as used herein means the minimum stirring rotation speed of a stirrer when a polymer having a desired viscosity is prepared by a polycondensation reaction which will be described later. The stopping operation of the stirrer for taking out the polymer thus prepared is not included in the definition of the polycondensation reaction.

With regard to the stirring rate before termination of the polymerization reaction under reduced pressure, the lower limit is typically 0.1 rpm or greater, preferably 0.5 rpm or greater, more preferably 1 rpm or greater, while the upper limit is 10 rpm or less, preferably 7 rpm or less, more preferably 5 rpm or less, most preferably 3 rpm or less. Too low stirring rates tend to retard the polymerization rate or cause unevenness in the viscosity of the resulting polymer. On the other hand, too high stirring rates tend to decompose the polymer, in the preparation of the biomass-resource-derived polymer having a high impurity content, due to shear heat. In the invention, it is preferred that the desired polyester is produced by stirring ordinarily at a rotation speed of 10 rpm or less, for 5 minutes or more, preferably 10 minutes or more and, more preferably 30 minutes or more.

With regard to the stirring rate at the starting time of the polymerization under reduced pressure, the lower limit is typically 10 rpm or greater, preferably 20 rpm or greater, more preferably 30 rpm or greater, while the upper limit is typically 200 rpm or less, preferably 100 rpm or less, more preferably 50 rpm or less. Too low stirring rates tend to retard the polymerization rate or prepare a polymer having an uneven viscosity. Too high stirring rates, on the other hand, tend to cause, during the preparation of particularly a biomass-resource-derived polymer having a high impurity content, decomposition of the resulting polymer due to shear heat.

The stirring rate during polymerization reaction under reduced pressure may be decreased continuously or in stages while observing a viscosity increase of the polyester. More preferably, it is important to set an average stirring rate 10 minutes before termination of the polycondensation reaction under reduced pressure lower than that 30 minutes after the initiation of the polycondensation reaction under reduced pressure. By this adjustment, it is possible to suppress thermal decomposition of a biomass-resource-derived polyester having a high impurity content and apt to undergo thermal decomposition during preparation of it, whereby a polymer can be prepared stably.

By controlling the stirring rate at the time of esterification reaction and/or ester exchange reaction, preparation of a by-product, for example, tetrahydrofuran when 1,4-butanediol is used as the diol can be reduced and the polymerization rate can be raised.

With regard to the stirring rate at the time of esterification reaction, the lower limit is typically 30 rpm or greater, preferably 50 rpm or greater, more preferably 90 rpm or greater, while the upper limit is 1000 rpm or less, preferably 500 rpm or less. Too low stirring rates tend to deteriorate a distillation efficiency and retard the esterification reaction. They tend to cause, for example, dehydration reaction or dehydration cyclization of the diol, leading to such drawbacks that an imbalance in a diol/dicarboxylic acid ratio occurs, thereby decreasing the polymerization rate and an excessive amount of the diol must be charged. Too high stirring rates are, on the other hand, economically disadvantageous because they consume extra power.

When the biomass-resource-derived dicarboxylic acid is used as a raw material of a polyester, the oxygen concentration and humidity may be controlled at the time of transfer of the dicarboxylic acid from the storage tank to the reactor. This makes it possible to prevent corrosion inside a transfer tube which will otherwise occur by a sulfur component contained as an impurity. Moreover, coloration due to the oxidation reaction of a nitrogen source can be prevented, making it possible to produce a polyester with good hue.

As the transfer tube, ordinarily employed tubes such as those made of a metal, those made of a metal having a glass or resin-lined inside, or those made of glass or resin are usable. From the standpoint of strength, tubes made of a metal or these made of a metal having a glass or resin-lined inside are preferred. For the tubes made of a metal, known materials are used. Specific examples include carbon steel, ferrite steel, martensitic stainless steels such as SUS410, austenitic stainless steels such as SUS310, SUS304 and SUS316, clad steel, cast iron, copper, copper alloy, aluminum, inconel, hastelloy and titanium.

Although no particular limitation is imposed on the lower limit of the oxygen concentration in the transfer tube based on the total volume of the transfer tube, it is typically 0.000010 or greater, preferably 0.01% or greater. The upper limit is, on the other hand, typically 16% or less, preferably 14% or less, more preferably 12% or less. Too low oxygen concentrations are economically disadvantageous because they may make the equipment investment or control step complicated. Too high oxygen concentrations, on the other hand, tend to enhance the coloration of a polymer thus prepared.

Although no particular limitation is imposed on the lower limit of the humidity in the transfer tube, it is typically 0.0001% or greater, preferably 0.001% or greater, more preferably 0.01% or greater, most preferably 0.1% or greater. The upper limit is 80% or less, preferably 60% or less, more preferably 40% or leas. Too low humidities tend to be economically disadvantageous because the step for humidity control becomes too complicated. Too high humidities tend to cause problems such as corrosion of the storage tank or pipes. When the humidity is too high, problems such as attachment of the dicarboxylic acid to the storage tank or pipes and blocking of the dicarboxylic acid occur and such attachment phenomena tend to accelerate the corrosion of the pipes.

The lower limit of the temperature in the transfer tube is typically −0.50° C. or greater, preferably 0° C. or greater. The upper limit is, on the other hand, typically 200° C. or lean, preferably 100° C. or less, more preferably 50° C. or less. Too low temperatures tend to increase the storage cost, while too high temperatures tend to cause dehydration reaction of the dicarboxylic acid simultaneously.

The pressure in the transfer tube is typically from 0.1 kPa to 1 MPa, but the transfer tube is used under the pressure of about 0.05 MPa or greater but not greater than 0.3 MPa from the viewpoint of operability.

When a polyester is produced, the dial is used in a substantially equimolar amount to 100 males of the dicarboxylic acid or derivative thereof, however, it is usually employed in 0.1 to 20 moles % excess in consideration of the distillation during the esterification reaction and/or ester exchange reaction and/or polycondensation reaction. When an aromatic polyester is produced, on the other hand, the number of terminal carboxyl groups tend to increase so that the diol is used in 10 to 60 mole % excess based on 100 moles of the dicarboxylic acid or derivative thereof.

The polycondensation reaction is preferably performed in the presence of a polymerization catalyst. The polymerization catalyst may be added in any stage without particular limitation insofar as it is prior to the polycondensation reaction. It may be added at the time of charging raw materials or at the time of starting pressure reduction.

As the polymerization catalyst, compounds containing a metal element in Group I to Group XIV of the periodic table except hydrogen and carbon are unable. Specific examples include organic-group-containing compounds such as carboxylates, alkoxy salts, organic sulfonates and β-diketonate salts each containing at least one metal selected from the group consisting of titanium, zirconium, tin, antimony, cerium, germanium, zinc, cobalt, manganese, iron, aluminum, magnesium, calcium, strontium, sodium and potassium, and inorganic compounds such as oxides or halides of the above-described metals, and mixtures thereof. These catalyst components may be contained in the raw materials of a polyester derived from biomass resources because of the above-described reason. In this case, the raw materials may be used as are as metal-containing raw materials without purifying them particularly. Polyesters having a higher degree of polymerization are sometimes prepared easily by using raw materials having a lower content of metal elements in Group I such as sodium or potassium. In such a case, raw materials purified until they become substantially free from metal elements in Group I are preferred.

Of these, metal compounds containing titanium, zirconium, germanium, zinc, aluminum, magnesium, or calcium, or a mixture thereof are preferred, of which titanium compounds, zirconium compounds and germanium compounds are especially preferred.

The catalyst is preferably a compound in the liquid form or compound soluble in an ester oligomer or polyester, because the catalyst in the molten or dissolved form at the time of polymerization increases the polymerization rate.

As the titanium compounds, tetraalkyl titanates are preferred. Specific examples include tetra-n-propyl titanate, tetraisopropyl titanate, tetra-n-butyl titanate, tetra-t-butyl titanate, tetraphenyl titanate, tetracyclohexyl titanate, and tetrabenzyl titanate, and mixtures thereof. In addition, titanium (oxy) acetylacetonate, titanium tetraacetylacetonate, titanium (diisoproxide) acetylacetonate, titanium his (ammonium lactate)dihydroxide, titanium bis(ethyl acetoacetate)diisopropoxide, titanium (triethanolaminate)isopropoxide, polyhydroxytitanium stearate, titanium lactate, titanium triethanolaminate and butyl titanate dimer are also preferred. Moreover, titanium oxide and composite oxide containing titanium and silicon (for example, titania/silica composite oxide (product name: C-94), product of Acordis Industrial Fibers) are also preferred. Of these, tetra-n-propyl titanate, tetraisopropyl titanate, tetra-n-butyl titanate, titanium (oxy)acetylacetonate, titanium tetraacetylacetonate, titanium bis(ammonium lactate)dihydroxide, polyhydroxytitanium stearate, titanium lactate, butyl titanate dimer, titanium oxide, and titania/silica composite oxide (for example, product names C-94, product of Acordis Industrial Fibers) are more preferred, with tetra-n-butyl titanate, titanium (oxy) acetylacetonate, titanium tetraacetylacetonate, polyhydroxytitanium stearate, titanium lactate, butyl titanate dimer, and titania/silica composite oxide (product name: C-94; product of Acordis Industrial Fibers) being still more preferred. In particular, tetra-n-butyl titanate, polyhydroxytitanium stearate, titanium (oxy) acetylacetonate, titanium tetraacetylacetonate, and titania/silica composite oxide (product name: C-94; product of Acordis Industrial Fibers) are preferred.

Specific examples of the zirconium compound include zirconium tetraacetate, zirconium acetate hydroxide, zirconium tris(butoxy)stearate, zirconyl diacetate, zirconium oxalate, zirconyl oxalate, potassium zirconium oxalate, polyhydroxyzirconium stearate, zirconium ethoxide, zirconium tetra-n-propoxide, zirconium tetraisopropoxide, zirconium tetra-n-butoxide, zirconium tetra-t-butoxide, and zirconium tributoxyacetylacetonate, and mixtures thereof. In addition, zirconium oxide and composite oxides containing zirconium and silicon are preferred. Of these, zirconyl diacetate, zirconium tris(butoxy) stearate, zirconium tetraacetate, zirconium acetate hydroxide, zirconium ammonium oxalate, potassium zirconium oxalate, polyhydroxyzirconium stearate, zirconium tetra-n-propoxide, zirconium tetraisopropoxide, zirconium tetra-n-butoxide, and zirconium tetra-t-butoxide are preferred, of which zirconyl diacetate, zirconium tetraacetate, zirconium acetate hydroxide, zirconium tris(butoxy)stearate, ammonium zirconium oxalate, zirconium tetra-n-propoxide, and zirconium tetra-n-butoxide are more preferred. Particularly, zirconium trim (butoxy) stearate is preferred because a polyester having a high degree of polymerization and free of coloration is easily available.

Specific examples of the germanium compound include inorganic germanium compounds such as germanium oxide and germanium chloride and organic germanium compounds such as tetraalkoxygermanium. In view of price and availability, germanium oxide, tetraethoxygermanium, tetrabutoxygermanium, and the like are preferred, with germanium oxide being especially preferred.

When the above-described metal compound is used as the polymerization catalyst, the lower limit of the using amount of it is, in terms of a metal amount based on the resulting polyester, typically 5 ppm or greater, preferably 10 ppm or greater and the upper limit is typically 30000 ppm or less, preferably 1000 ppm or less, more preferably 250 ppm or less, especially preferably 130 ppm or less. Too large amounts of the catalyst are not only economically disadvantageous but also deteriorate the thermal stability of the polymer. Too small amounts, on the other hand, lower the polymerization activity and tend to induce decomposition of the polymer during the preparation thereof. The concentration of the terminal carboxyl group of the resulting polyester decreases with a reduction in the using amount of the catalyst so that a method of reducing the using amount of the catalyst is preferred.

With regard to the temperature of the esterification reaction/or ester exchange reaction of the dicarboxylic acid component and diol component, the lower limit is typically 150° C. or greater, preferably 180° C. or greater and the upper limit is typically 260° C. or less, preferably 250° C. or less. The reaction atmosphere is typically an inert gas atmosphere such as nitrogen or argon. The reaction pressure is typically from normal pressure to 10 kPa, with normal pressure being preferred.

With regard to the reaction time, the lower limit is typically 1 hour or greater, while the upper limit is typically 10 hours or less, preferably 4 hours or less.

The polycondensation reaction after the esterification reaction and/or ester exchange reaction of the dicarboxylic acid component and the diol component is performed under vacuum while controlling the lower limit of the pressure to typically $0.01 \times 10^3$ Pa or greater, preferably $0.05 \times 10^3$ Pa or greater and the upper limit to typically $1.4 \times 10^3$ Pa or less, preferably $0.4 \times 10^3$ Pa or less. With regard to the reaction temperature during the polycondensation reaction, the lower limit is typically 150° C. or greater, preferably 180° C. or greater and the upper limit is typically 260° C. or less, preferably 250° C. or less. The lower limit of the reaction time is typically 2 hours or greater, while the upper limit is typically 15 hours or less, preferably 10 hours or less.

In the invention, as a reactor for producing the polyester, known vertical or horizontal stirred tank reactors can be used. For example, a method of carrying out melt polymerization, which has a step of an esterification reaction and/or ester exchange reaction and a step of polycondensation under reduced pressure, in two stages in reactors which are the same or different and using, as a reactor for polycondensation under reduced pressure, a stirred tank reactor fitted with a decompression exhaust tube connecting a vacuum pump and the reactor can be employed. And, a method of recovering volatile components generated during the polycondensation reaction and unreacted monomers in a condenser in the middle of the decompression exhaust tube connecting the vacuum pump and the reactor can be employed preferably.

In the invention, processes used for producing an aliphatic ester include a process of carrying out an esterification reaction and/or ester exchange reaction between a dicarboxylic acid component containing the above-described aliphatic dicarboxylic acid and an aliphatic dial component and then increasing the degree of polymerization of the polyester while distilling off the diol formed by the ester exchange reaction of the terminal alcohol group of the polyester; and a process of increasing the degree of polymerization of the polyester while distilling off the aliphatic dicarboxylic acid and/or cyclic acid anhydride thereof from the terminal aliphatic carboxyl group of the polyester. In the latter process, the aliphatic carboxylic acid and/or cyclic acid anhydride thereof is removed typically by distilling off the aliphatic dicarboxylic acid and/or cyclic acid anhydride thereof by heating during the polycondensation reaction under reduced pressure, that is, a latter-stage reaction of the melt polymerization. Under the polycondensation reaction conditions, the aliphatic dicarboxylic acid is easily converted into the cyclic acid anhydride thereof so that it is usually distilled off by heating in the form of a cyclic acid anhydride. During this distillation, linear or cyclic ether and/or diol derived from the dial may be removed together with the aliphatic dicarboxylic acid and/or cyclic acid anhydride thereof. It is preferred to employ a method of distilling off the cyclic monomers of the dicarboxylic acid component and diol component together, because it improves a polymerization rate.

On the other hand, in producing an aromatic polyester, the former process of heightening the degree of polymerization of the polyester while using excess diol and distilling off the added portion of the diol as described above is preferred.

During the production process of the polyester or after production of the polyester, various additives, for example, a plasticizer, ultraviolet stabilizer, coloration preventive, matting agent, deodorant, flame retardant, weathering stabilizer, antistatic, yarn friction reducing agent, release agent, antioxidant, ion exchange agent, and inorganic fine particles and organic compounds as coloring pigments may be added as needed within a range not impairing the properties of the polyester. Examples of the coloring pigment include inorganic pigments such as carbon black, titanium oxide, zinc oxide and iron oxide and organic pigments such as cyanine, styrene, phthalocyanine, anthraquinone, perynone, isoindolinone, quinophthalone, quinocridone and thioindigo. A quality modifier such as calcium carbonate or silica can also be added.

In the present invention, the temperature of the polyester when it is taken out from a polymerization reactor after completion of the polymerization reaction may be controlled. This makes it possible to take out a high viscosity polyester while suppressing thermal decomposition of it.

With regard to the temperature of the polyester when it is taken out from the polymerization reactor, assuming that the resin temperature at the time when the pressure of the polymerization reactor is returned from the reduced pressure to the normal pressure or greater after completion of the polymerization is Te, the lower limit is (Te−50)° C. or greater, preferably (Te−30)° C. or greater, more preferably (Te−20)° C. or greater, most preferably (Te−10)° C. or greater, while the upper limit is (Te+20)° C. or less, preferably (Te+10)° C. or less, more preferably Te° C. or less. Too low temperatures tend to cause a problem in productivity because an increase in the viscosity of the polyester at the time of discharging it from the reactor disturbs smooth discharge of it. At too high temperatures, on the other hand, the thermal decomposition of the polyester occurs considerably.

The temperature of the polyester at the time of discharging it from the tank can be measured by a thermocouple attached inside the polymerization reactor to measure the temperature thereof.

In the present invention, the polyester in the form of strands taken out from the polymerization reactor may be brought into contact with an aqueous medium of a specific temperature or less after completion of the polymerization reaction. This enables to obtain a high viscosity polyester while suppressing the decomposition of it.

Although no particular limitation is imposed on the medium for cooling the polyester, examples include dials such as ethylene glycol, alcohols such as methanol and ethanol, acetone and water. Of these, water is most preferred. These aqeuous solvents may be used in combination of two or more thereof.

With regard to the temperature of the solvent, the lower limit is typically −20° C. or greater, preferably −10° C. or greater, more preferably 0° C. or greater, most preferably 4° C. or greater, while the upper limit is typically 20° C. or less, preferably 15° C. or less, more preferably 10° C. or less. Too low temperatures tend to be economically disadvantageous because they increase the operation cost of cooling equipment of the medium. Too high temperatures tend to cause marked thermal decomposition of the polyester when it is taken out in the form of strands.

With regard to the cooling time of the polyester, the lower limit is typically 0.1 second or greater, preferably 1 second or greater, more preferably 5 seconds or greater, most preferably 10 seconds or greater, while the upper limit is typically 5 minutes or less, preferably 2 minutes or less, more preferably 1 minute or less, most preferably 30 seconds or less. Too short cooling time tends to cause marked fusion of strands and disturbs pelletization. Too long cooling time tends to act on productivity adversely.

Although no particular limitation is imposed on the cooling method, examples include a method of taking out the polyester from the polymerization reactor in the form of strands and causing it to go into the cooling medium or a method of showering the strands with the cooling medium.

<Pellets of Polyester>

After completion of the polymerization reaction, the polyester taken out from the polymerization reactor in the form of strands is cooled with water, air or the like. Then, it is pelletized by a known fixed or rotary cutter or pelletizer. The pellets thus obtained may be stored.

The shape of the pellets is typically spherical or cylindrical with a circular or elliptical cross-section.

The diameter of the polyester pellets is adjusted by controlling the diameter of a discharging outlet of the polymerization reactor, discharging rate of strands, taking-up rate, cutting speed or the like. Described specifically, it is adjusted, for example, by controlling the pressure in the reactor at the time of discharging the polymer therefrom or a cutting speed of a rotary strand cutter.

With respect to the diameter of the polyester pellets thus obtained, the lower limit (minimum diameter) is typically 0.1 mm or greater, preferably 0.2 mm or greater, more preferably 0.5 mm or greater, most preferably 1 mm or greater, while the upper limit (maximum diameter) is 20 mm or less, preferably 10 mm or less, more preferably 7 ma or less, most preferably 4 mm or less. Too small diameters tend to cause marked deterioration of the pellets due to hydrolysis during the storage of the pellets. Too large diameters, on the other hand, tend to cause unevenness in the product because of inferiority in the feed stability of the pellets at the time of molding.

In the polyester pellets of the present invention, the proportion of powders having the maximum diameter less than 1 mm is preferably 2.0 wt. % or less, more preferably 1.0 wt. % or less. When the proportion of the powder having the maximum diameter less than 1 mm is too large, presence of the powder increases the residence time of the pellets in the molding machine owing to inferior feed stability of the pellets in the screw of the machine at the time of melt molding, and thermal deterioration which may occur owing to an increase in their surface area causes mixing of foreign matters such as scorch or hard spots in the molded product, resulting in the problems such as deterioration in mechanical strength or appearance of the molded product.

The term "diameter of the polyester pellets" as used herein means the diameter or length of the cross-section of the polyester pellets. The term "the cross-section of the polyester pellets" means the cross-section of the polyester pellets having the maximum cross-sectional area.

In the present invention, a water content in the polyester pellets during storage may be controlled. Although no particular limitation is imposed on the lower limit of the water content, as a mass ratio, based on the polyester, it is typically 0.1 ppm or greater, preferably 0.5 ppm or greater, more preferably 1 ppm or greater, most preferably 10 ppm or greater. The upper limit is typically 3000 ppm or less, preferably 2000 ppm or less, more preferably 1000 ppm or less, especially preferably 000 ppm or less, most preferably 500 ppm or less. Too low water contents tend to be economically disadvantageous because they make the equipment or controlling step complicated. In addition, it takes much time for drying so that they tend to cause coloration of the polyester or deterioration thereof such as generation of hard spots. Too high water contents, on the other hand, tend to cause marked deterioration of the polyester due to hydrolysis during storage of pellets.

The water containing amount (water content) in the polyester pellets may be measured by heating and melting 0.5 g of a pellet sample at 200° C. by using a moisture vaporizer ("VA-100", product of Mitsubishi Chemical) to evaporate water from the sample and then determining the total water content thus evaporated by coulometric titration based on the principle of the Karl Fischer reaction by using a trace moisture meter ("CA-100", product of Mitsubishi Chemical).

In the polyester pellets of the present invention, the polyester undergoes hydrolysis by moisture and has deteriorated properties so that the pellets may be stored in a hermetically sealed condition. The term "hermetically sealed condition" as used herein means a condition under which the dry state of the polyester can be maintained.

Examples of the hermetically sealing method include storage in a space equipped with a hermetically sealing function; storage in a bag equipped with a hermetically sealing function; covering the polyester pellets with a sheet equipped with a hermetically sealing function; and storage in a silo under a dry atmosphere (including dry air or circulation of nitrogen). Of these, storage in a bag equipped with a hermetically sealing function is preferred.

The bag is preferably made of a highly airtight material. Films or sheets made of a synthetic resin are preferred. Specific examples include sheets made of a polyolefin resin such as polyethylene or polypropylene or polyvinyl chloride resin and these sheets reinforced with a polyester or polyamide film or various fiber base materials. These sheets may have a barrier layer stacked thereover as needed for blocking water vapor or oxygen. A composite film such as polyester/aluminum/polyethylene film is one example of such a film stack.

Various packaging materials having such properties are commercially available. Of these, those easily sealed by heating are preferred. The materials are formed into packaging bags by heat fusion and/or sewing.

No particular limitation is imposed on the shape of the packaging bag and known bag shapes such as flat bag, gadget bag, square-bottom bag and flexible containers can be employed. These bags preferably have a bottom surface in consideration that the cross-sectional shape of the base of the package when the pellets are actually packaged therein is made substantially rectangular. Of these, gadget bags, square-bottom bags and flexible containers are preferred. Bags having a substantially rectangular bottom shape are more preferred because the packages can easily have a base with a substantially rectangular cross-section while having the pellets therein.

The polyester pellets derived from biomass sources contain impurities so that they are susceptible to coloration or deterioration. They may therefore be stored with light shielding.

Although no particular limitation is imposed on the light shielding method insofar as it can shield the polyester from the light, specific examples include storage in a space equipped with a light shielding function, storage in a bag equipped with a light shielding function, and covering the polyester pellets with a sheet equipped with a light shielding function. Of these, storage in a bag equipped with a light shielding function is preferred.

With respect to the light shielding degree, the upper limit of the illuminance of the space is typically 300 lux or less, preferably 70 lux or less, more preferably 1 lux or less, most preferably 0.001 lux or less, while the lower limit is not particularly limited. Too high illuminance tends to cause marked coloration of the polyester, while too low illuminance is economically disadvantageous because control of it is difficult.

With respect to the temperature during the storage of the polyester pellets, the lower limit is −50° C. or higher, preferably −30° C. or higher, more preferably 0° C. or higher, while the upper limit is 80° C. or less, preferably 50° C. or less, more preferably 30° C. or less. Storage at room temperature is most preferred because it does not need temperature control step. Too low temperatures are economically disadvantageous because they make the control step complicated. Too high temperatures, on the other hand, tend to cause marked deterioration of the polyester.

Although no particular limitation is imposed on the external pressure during the storage of the polyester pellets, it is typically atmospheric pressure (normal pressure).

A polyester composition which will be described later may be stored under the above-described conditions after pelletization.

<Physical Properties of Polyester>

The polyester pellets of the present invention are available from the polyester having the following physical properties. Their physical properties do not deteriorate even after storage.

The physical properties of the polyester of the present invention will be explained using a polyester composed of an aliphatic diol and an aliphatic dicarboxylic acid such as polybutylene succinate and polybutylene succinate adipate, as an example. It has similar properties to those of the general-purpose polymers, more specifically, it has a density from 1.2 to 1.3 g/cm$^3$, malting point from 80 to 120° C., tensile strength from 30 to 80 Mpa, tensile elongation at break from 300 to 6001, Young modulus from 400 to 700 MPa, Izod impact strength from about 5 to 20 kJ/m$^2$, and glass transition point from −45 to −25° C. If the polyester is used for a special purpose, it can have properties falling within more-wide desired ranges without limitation to the above-described ranges. Moreover, it can have melting point, melt index and melt viscoelasticity sufficient to permit preparation of a molded product by various molding means. These properties can be controlled freely by changing the kind of polyester raw materials or additives thereto, polymerization conditions, or molding conditions in accordance with the intended use.

Detailed ranges of the typical physical properties of the polyester of the present invention will hereinafter be disclosed.

Although no particular limitation is imposed on the melting point of the polyester of the present invention, it is typically from 40 to 270° C., preferably from 50 to 230° C., more preferably from 60 to 130° C. The melting point is determined by the above-described components so that it is possible to produce a polyester having a melting point within the above-described range by selecting proper components.

With respect to the number-average molecular weight, in terms of polystyrene, of the polyester of the present invention, the lower limit is typically 5000 or greater, preferably 10000 or greater, more preferably 15000 or greater, while the upper limit is typically 500000 or less, preferably 300000 or less.

With respect to the composition ratio of the copolyester, a molar ratio of the diol unit to the dicarboxylic acid unit must be substantially 1.

The content of nitrogen atoms contained in the polyester of the present invention other than those contained in the covalently bonded functional groups is 1000 ppm or less based on the mass of the polyester. The content of nitrogen atoms in the polyester other than those contained in the covalently bonded functional groups is preferably 500 ppm or less, more preferably 100 ppm or less, still more preferably 50 ppm or less, of which 40 ppm or less is preferred, 30 ppm or less is more preferred and 20 ppm or less is most preferred. The content of nitrogen atoms in the polyester other than those contained in the covalently bonded functional groups is mainly derived from nitrogen atoms in the raw materials. The content of nitrogen atoms in the polyester other than those contained in the covalently bonded functional groups is preferably 1000 ppm or less because if so, coloration or generation of foreign matters at the time of molding is suppressed and heat- or light-induced deterioration or hydrolysis of the molded product does not occur easily.

In addition, for some using purpose, the content of nitrogen atoms in the polyester other than those contained in the covalently bonded functional groups not greater than 100 ppm or less is preferred, because coloration or generation of foreign matters of the polyester is suppressed at such a content. The lower the nitrogen atom content, the more eminent its effect becomes.

On the other hand, the content of nitrogen atoms in the polyester other than those contained in the covalently bonded functional groups is preferably 0.01 ppm or greater, more preferably 0.05 ppm or greater, still more preferably 0.1 ppm or greater, especially preferably 1 ppm or greater. Nitrogen atom contents less than 0.01 ppm are disadvantageous from the standpoint of energy because a certain load is applied during the purification of the raw materials. In addition, an adverse effect on the environment cannot be neglected;

Nitrogen atom contents of 1 ppm or greater are preferred because they accelerate a biodegradation rate in a soil when the polyester is an aliphatic polyester. Use of the raw materials having a nitrogen atom content falling within the above-described range is effective for accelerating biodegradability of the polyester thus obtained without decreasing the polymerization rate of the polyester in the polymerization reaction. The nitrogen atom content can be measured by chemiluminescence, a conventionally known method which will be described later. The term "ppm" as used herein means mass ppm.

The term "covalently bonded functional groups in the polyester" as used herein means urethane functional groups derived from the above-described diisocyanate compounds or carbodiimide compounds, unreacted isocyanate functional groups, urea functional groups and isourea functional groups, and unreacted carbodiimide functional groups. Accordingly, in the invention, the "content of nitrogen atom in the polyester other than those contained in the covalently bonded functional groups" is a value obtained by subtracting, from the total nitrogen atom content in the polyester, the nitrogen atom contents belonging to the urethane functional groups, unreacted isocyanate functional groups, urea functional groups, and isourea functional groups, and unreacted carbodiimide functional groups. The content of the urethane functional groups, unreacted isocyanate functional groups, urea functional groups, and isourea functional groups, and unreacted carbodiimide functional groups can be determined from the above-described $^{13}$C-NMR, spectrophotometry such as IR, or a feeding amount at the time of producing the polyester.

With regard to a ratio of the nitrogen content in the polyester of the present invention to an ammonia content in the raw materials is preferably 0 or greater but not greater than 0.9, more preferably 0 or greater but not greater than 0.6, especially preferably 0.3 or less.

With regard to the sulfur atom content in the polyester of the present invention, the upper limit is 50 ppm or less, preferably 5 ppm or less, more preferably 3 ppm or less, most preferably 0.3 ppm or less in terms of atoms based on the mass of the polyester. Although no particular limitation is imposed on the lower limit, it is 0.0001 ppm or greater, preferably 0.001 ppm or greater, more preferably 0.01 ppm or greater, especially preferably 0.05 ppm or greater, most preferably 0.1 ppm or greater. Too high sulfur contents tend to deteriorate thermal stability or hydrolysis resistance of the polyester. The system with a too low sulfur atom content tends to be economically disadvantageous in the production of the polyester because of a marked increase in the purification cost.

In the polymer of the present invention, the polyester obtained using raw materials derived from biomass resources tends to contain therein volatile organic components, for example, tetrahydrofuran and acetaldehyde. The upper limit of their content in the polyester is typically 10000 ppm or less, preferably 3000 ppm or less, more preferably 1000 ppm or less, most preferably 500 ppm or less. Although no particular limitation is imposed on the lower limit, it is typically 1 ppb or greater, preferably 10 ppb or greater, more preferably 100 ppb or greater. Too high volatile contents may become responsible for an odor and in addition, may cause foaming during melt molding or worsening of storage stability. The system with a too low volatile content is preferred, but is economically disadvantageous because it needs a remarkably large amount of equipment investment and also tremendous production time.

The reduced viscosity ($\eta$sp/c) of the polyester produced in the present invention is 0.5 or greater because the resulting polyester can have enough mechanical properties for its practical use. In particular, 1.0 or greater is preferred, with 1.8 or greater being more preferred and with 2.0 or greater being especially preferred. The upper limit of the reduced viscosity ($\eta$sp/c) is typically 6.0 or less, preferably 5.0 or less, more preferably 4.0 or less in view of operability such as easy discharge and moldability or formability, each of the polyester after polymerization reaction.

The reduced viscosity in the present invention is measured under the following conditions:

[Measurement Conditions of Reduced Viscosity ($\eta$sp/c)]
Viscosity tube: Ubbelohde's viscosity tube
Measurement temperature 30° C.
Solvent: phenol/tetrachloroethane (1:1 weight ratio) solution
Polyester concentration; 0.5 g/dl The polyester of the present invention is preferably soluble uniformly when 0.5 g of it is dissolved in a phenol/tetrachloroethane (1:1 weight ratio) solution (volume: 1 dl) at room temperature. If an insoluble component of the polyester appears, the amount of an insoluble component is typically 1 wt. % or less, more preferably 0.1 wt. % or less, especially preferably 0.01 wt. % or less in the total amount of the polyester.

The concentration of the terminal carboxyl group in the polyester of the present invention is typically 100 equivalents/metric ton or less, more preferably 50 equivalents/metric ton or less, especially preferably 35 equivalents/metric ton or less, more preferably 25 equivalents/metric ton or less, while it is 0.1 equivalent/metric ton or greater, preferably 0.5 equivalent/metric ton or greater, especially 1 equivalent/metric ton or greater. Too high concentrations tend to deteriorate thermal stability of the polymer at the time of its molding or hydrolysis resistance during a relatively long period of use or storage. The polymer having a too low concentration of carboxyl groups is preferred, but is economically disadvantageous because it requires a substantial equipment investment and also much time for its production.

Presence of a large amount of nitrogen-containing compounds or sulfur-containing compounds in the dicarboxylic acid and/or diol tends to cause an increase in the concentration of terminal carboxyl groups in the polymer, because such impurities become crosslinking points of the polymer or accelerate thermal decomposition reaction of the polymer. In order to control the concentration of terminal carboxyl groups within the above-described range, a method of controlling the amount of the nitrogen-containing compounds or sulfur-containing compounds within the above-described range, a method of reducing the using amount of the catalyst, or a method of producing the polymer at lower polymerization temperature is preferably employed.

The amount of terminal carboxyl groups is typically calculated by a known titration method. In the present invention, it is a value obtained by dissolving the polyester thus obtained in benzyl alcohol and conducting titration with 0.1N NaOH and is a carboxyl equivalent per $1\times10^6$ g.

The polyester produced by the present invention is preferably a less colored polyester. With respect to the yellowness (YI) of the polyester of the present invention, the upper limit is typically 50 or less, preferably 30 or less, more preferably 20 or less, still more preferably 15 or less, especially preferably 10 or less. Although no particular limitation is imposed on the lower limit, it is typically −20 or greater, preferably −10 or greater, more preferably −5 or greater, especially preferably −3 or greater, most preferably −1 or greater. The polyester having a high YI has the drawback that its use for, for example, film or sheet is limited. The polyester having a low YI, on the other hand, is preferred, but may be economically disadvantageous because production of such a polymer requires a complicated production process and substantial equipment investment. In the present invention, the YI is a value as measured by the method based on JIS K7105.

<Polyester Composition>

A polyester composition is available by blending (kneading) the aliphatic polyester obtained in the above-described process with a conventionally known resin. As such a resin, various conventionally-known general-purpose resins such as thermoplastic resins, biodegradable resins and natural resins are usable. Biodegradable polymers and general-purpose thermoplastic resins are preferred. They may be used either singly or as a mixture of two or more thereof. These various resins may be derived from biomass resources.

The aliphatic polyester of the present invention is blended (kneaded) with a known resin to yield a polyester composition having desired and wide range of properties. For example, a blending ratio is not particularly limited because physical properties of the composition vary greatly with a blending ratio. A composition obtained by blending polybutylene succinate and polylactic acid, which will be described later, can have properties similar to those of the general-purpose polymers, more specifically, it has a tensile strength from 30 to 60 Mpa, tensile elongation at break from 3 to 400%, Young modulus in tension from 500 to 3000 Mpa, tensile yield strength from 30 to 50 Mpa, flexural strength from 30 to 100 Mpa, flexural modulus from 600 to 4000 Mpa, and Izod impact test strength from 5 to 20 kJ/me. A polyester composition obtained by blending with a flexible aromatic polyester also can have physical properties similar to those of the general-purpose polymers, more specifically, it has a tensile strength from 30 to 70 Mpa, tensile elongation at break from 400 to 8000 and tensile yield strength from 10 to 30 Mpa. A polyester composition obtained by blending with a general-purpose resin such as nylon, polycarbonate, polyacetal, ABS, PET or polystyrene can have physical properties similar to those of general-purpose polymers, more specifically, it has a density from 1 to 1.4 g/cm$^3$, melting point from 150 to 270° C., tensile strength from 30 to 80 Mpa, tensile elongation at break from 100 to 6004, and glass transition point from −85 to 150° C. These properties can be adjusted freely by changing the kind of the raw materials of polyester or various resins, a ratio of blended amount or molding conditions depending on the using purpose.

The general-purpose thermoplastic resin to be blended with the biomass-resource-derived polyester of the present invention can be selected desirably from general-purpose thermoplastic resins such as polyesters derived from petroleum which will be described later, polyvinyl acetate, polyvinyl alcohol, polyester, polycarbonate and polyamide. In this case, compatibility with the biomass-resource-derived polyester must be considered. A blending amount is also an important factor for appropriately retaining the properties of the biomass-resource-derived polyester of the present invention. The blending amount of the biomass-resource-derived polyester is typically from 99.9 to 20 wt. % and it can be blended with from about 0.1 to 80 wt. % of the general-purpose plastic resin. In order to retain the properties of the biomass-resource-derived polyester such as biodegradability, however, the blending amount of the general-purpose thermoplastic resin is reduced to from 50 to 1 wt. S, preferably from about 30 to 3 wt. %, though depending on the purpose. Then, it is possible to impart predetermined physical properties to the polyester while retaining the biodegradability.

Examples of the biodegradable polymer include aliphatic polyester resins, polycaprolactone, polylactic acid, polyvinyl alcohol, polyethylene succinate, polybutylene succinate, polysaccharides and other biodegradable resins.

With respect to the blending amount of the biodegradable polymers, when biodegradable resins are employed as both resins for imparting only biodegradability to the resulting composition, appropriate biodegradability appears even by blending from about 0.1 to 99.9 wt. % of the biodegradable polymer with from 99.9 to 0.1 wt. % of the biomass-resource-derived polyester of the present invention. From the viewpoint of the biomass-resource-derived polyester of the present invention, however, it is preferred to blend from 99.9 to 40 wt. % of the biomass-resource-derived polyester with from about 0.1 to 60 wt. % of the biodegradable polymer, with the blending of the biodegradable polymer in an amount of from about 5 to 50 wt. % being more preferred.

Examples of the natural resin or polysaccharide to be incorporated in the biomass-resource-derived polyester of the present invention include cellulose acetate, chitosan, cellulose, chroman indene, rosin, lignin and casein. These natural resins and polysaccharides have a property of decaying, in their essential natural state, in the presence of water and air and returning to the soil or becoming a fertiliser. It is possible to mix from 99.9 to 0.1 wt. % of the biomass-resource-derived polyester of the present invention with from about 0.1 to 99.9 wt. % of the natural resin or polysaccharide. It is more preferred to mix from about 5 to 50 wt. % of the natural resin or polysaccharide in order to retain not only biodegradability necessary for the biomass-resource-derived polyester but also various properties such as mechanical properties, water resistance and weather resistance which the plastic are required to have essentially.

Compatibility between the biomass-resource-derived polyester of the present invention and the natural resin or polysaccharide is also a problem. If this problem is overcome, when a material made of a composition composed of the biomass-resource-derived polyester of the present invention and the natural resin is discarded after use, the decomposition of the natural resin or polysaccharide occurs and the material may be effective as a soil improver or fertilizer, though early biodegradation and disappearance cannot be expected. Such a polyester resin is sometimes recommended to be discarded positively to nature, particularly to soil so that the material which has overcome the problem of compatibility has increased significance as a green plastic product. Specific compositions of each resin will next be disclosed, but not particularly limited thereto.

Examples of the aliphatic polyester resins include aliphatic polyester resins having, as essential components, aliphatic and/or alicyclic diol units and aliphatic and/or alicyclic dicarboxylic acid unit and aliphatic oxycarboxylic acid resins.

Specific examples of the aliphatic and/or alicyclic diol unit constituting the aliphatic polyester resin include ethylene glycol unit, diethylene glycol unit, triethylene glycol unit, polyethylene glycol unit, propylene glycol unit, dipropylene glycol unit, 1,3-butanediol unit, 1,4-butanediol unit, 3-methyl-1,5-pentanediol unit, 1,6-hexanediol unit, 1,9-nonanediol unit, neopentyl glycol unit, polytetramethylene glycol unit and 1,4-cyclohexanedimethanol unit. These units may be used as a mixture of two or more of them.

Specific examples of the aliphatic and/or alicyclic dicarboxylic acid unit constituting the aliphatic polyester resin include succinic acid unit, oxalic acid unit, malonic acid unit, glutaric acid unit, adipic acid unit, pimelic acid unit, suberic acid unit, azelaic acid unit, sebacic acid unit, undecanedioic acid unit, dodecanedioic acid unit, 1,4-cyclohexanedicarboxylic acid unit. These units may be used as a mixture of two or more of them.

Specific examples of the aliphatic oxycarboxylic acid unit constituting the aliphatic oxycarboxylic acid resin include glycolic acid unit, lactic acid unit, 3-hydroxybutyric acid unit, 4-hydroxybutyric acid unit, 4-hydroxyvaleric acid unit, 5-hydroxyvaleric acid unit, and 6-hydroxycaproic acid unit. These units may be used as a mixture of two or more of them.

The aliphatic polyester resin may be copolymerized with an oxycarboxylic acid unit such as lactic acid unit or 6-hydroxycaproic acid unit. The above-described oxycarboxylic acid unit is used in an amount, as the upper limit, of typically 70 mole % or less, preferably 50 mole % or less, more preferably 30 mole % or less, most preferably 10 mole % or less based on 100 mole % of all the monomer units constituting the polyester.

The aliphatic polyester resin may be copolymerized with a tri- or higher functional alcohol or carboxylic acid. More specifically, it may be copolymerized with a tri- or higher functional polyhydric alcohol, polycarboxylic acid or polyoxycarboxylic acid such as trimethylolpropane, glycerin, pentaerythritol, propanetricarboxylic acid, malic acid, citric acid, tartaric acid, hydroxyglutaric acid, hydroxymethylglutaric acid, hydroxyisophthalic acid or hydroxyterephthalic acid. With regard to the amount of the tri- or higher functional compound unit which may be a cause for generation of a gel, the upper limit is typically 5 mole % or less, preferably 1 mole % or less, more preferably 0.50 mole % or less, especially 0.3 mole % or less based on 100 mole % of all the monomer units constituting the polyester. When a tri- or higher functional compound is used as a copolymerizable component for easily preparing a polyester having a high degree of polymerization, the lower limit of its using amount that can bring about its effect is typically 0.0001 mole % or greater, preferably 0.001 mole % or greater, more preferably 0.005 mole % or greater, especially preferably 0.01 mole % or greater. The aliphatic oxycarboxylic acid resin may be copolymerized with an aliphatic and/or alicyclic diol unit or an aliphatic and/or alicyclic dicarboxylic acid unit such as 1,4-butanediol unit, succinic acid unit or adipic acid unit; or a tri- or higher functional aliphatic polyhydric alcohol unit, aliphatic polycarboxylic acid unit or aliphatic polyoxycarboxylic acid unit such as trimethylolpropane unit, glycerin unit, pentaerythritol unit, propanetricarboxylic acid unit, malic acid unit, citric acid unit, or tartaric acid unit. The upper limit of the amount of the above-described unit is typically 90 mole % or less, preferably 70 mole % or less, more preferably 50 mole % or less based on 100 mole % of all the monomer units constituting the polyester.

The diol (polyhydric alcohol) unit, dicarboxylic acid (polycarboxylic acid) unit and oxycarboxylic acid unit constituting the aliphatic polyester resin have an aliphatic compound unit as a main component, but the aliphatic polyester resin may contain a small amount of another component, for example, an aromatic compound unit such as aromatic diol (polyhydric alcohol) unit, aromatic dicarboxylic acid (polycarboxylic acid) unit or aromatic oxycarboxylic acid unit without impairing biodegradability of the resin. Specific examples of the aromatic diol (polyhydric alcohol) unit include bisphenol A unit and 1,4-benzenedimethanol unit; those of the aromatic dicarboxylic acid (polycarboxylic acid) unit include terephthalic acid unit, isophthalic acid unit, trimellitic acid unit, pyromellitic acid unit, benzophenonetetracarboxylic acid unit, phenylsuccinic acid unit and 1,4-phenylenediacetic acid unit; and those of the aromatic oxycarboxylic acid unit include hydroxybenzoic acid unit. The introduction amount of these aromatic compound units is 50 mole % or less, preferably 30 mole % or less based on the whole polymer.

No particular limitation is imposed on the production process of the aliphatic polyester resin and a publicly known manner can be employed. An urethane bond, amide bond, carbonate bond, ether bond, ketone bond or the like may be introduced into the aliphatic polyester resin without adversely affecting the biodegradability thereof. As the aliphatic polyester, that having an increased molecular weight or being crosslinked by using, for example, an isocyanate compound, epoxy compound, oxazoline compound, acid anhydride, peroxide, or the like may be used. Further, it may be sealed, at the and group thereof, with a carbodiimide, epoxy compound, monofunctional alcohol or carboxylic acid.

Examples of the polysaccharides include cellulose, modified cellulose such as cellulose acetate, chitin, chitosan, starch and modified starch.

Examples of the other biodegradable resin include polyvinyl alcohol, modified polyvinyl alcohol, and polyalkylene glycols such as polyethylene glycol and polypropylene glycol.

Examples of the general-purpose thermoplastic resin include polyolefin resins such as polyethylene, polypropylene, ethylene-vinyl acetate copolymer and ethylene-α-olefin copolymer, halogenated resins such as polyvinyl chloride, polyvinylidene chloride, chlorinated polyolefin and polyvinylidene fluoride; styrene resins such as polystyrene and acrylonitrile-butadiene-styrene copolymer, polyester resins such as polyethylene terephthalate and polybutylene terephthalate; elastomers such as polyisoprene, polybutadiene, acrylonitrile-butadiene copolymer rubber, styrene-butadiene copolymer rubber and styrene-isoprene copolymer rubber;

polyamide resins such as nylon 66 and nylon 6: and polyvinyl acetate, methacrylate resins, polycarbonate resins, polyacetal, polyphenylene oxide and polyurethane. Their various properties may be adjusted by using a compatibilizer agent in combination.

The mixing ratio (weight ratio) of the polyester of the present invention to the above-described resin in the polyester composition will be described above specifically. The general mixing ratio, to be used in common, of the polyester resin of the present invention to various resins is preferably 99.9/0.1 or greater but not greater than 0.1/99.9, more preferably 99/1 or greater but not greater than 1/99, most preferably 90/2 or greater but not greater than 2/98.

The composition can also be obtained by adding various conventionally known additives.

The additives are those used for resins and examples include crystal nucleating agent, antioxidant, antiblocking agent, ultraviolet absorber, light stabilizer, plasticiser, heat stabiliser, colorant, flame retardant, release agent, antistatic, antifog agent, surface wetness improver, incineration assistant, pigment, lubricant, dispersing aid, and various surfactants. These additives are added typically in an amount of from 0.01 to 5 wt. % based on the total weight of the composition. These additives may be used either singly or as a mixture of two or more of them.

The polyester composition is also available by incorporating various conventionally-known fillers therein. As a functional additive, chemical fertilizer, soil improver, plant activator or the like can also be added. The fillers can be classified roughly into inorganic fillers and organic fillers. They may be used either singly or as a mixture of two or more of then.

Examples of the inorganic filler include anhydrous silica, mica, talc, titanium oxide, calcium carbonate, diatomaceous earth, allophane, bentonite, potassium titanate, zeolite, sepiolite, smectite, kaolin, kaolinite, glass, limestone, carbon, wollastonite, calcined pearlite, silicates such as calcium silicate and sodium silicate, aluminum oxide, magnesium carbonate, hydroxides such as calcium hydroxide, and salts such as ferric carbonate, zinc oxide, iron oxide, aluminum phosphate and barium sulfate. The content of the inorganic filler is typically from 1 to 80 wt. %, preferably from 3 to 70 wt. %, more preferably from 5 to 60 wt. % based on the total weight of the composition. Some of the inorganic fillers, for example, calcium carbonate and limestone, have properties of a soil improver. If a biomass-resource-derived polyester composition containing a particularly large amount of the above-described inorganic filler is discarded to soil, the inorganic filler after biodegradation remains in the soil and functions as a soil improver. The resulting composition has therefore increased significance as green plastic. Usefulness of the polyester of the present invention can be enhanced by molding the polyester composition added with a chemical fertilizer, soil improver, plant activator, or the like and using the product thus obtained as a material to be discarded in the soil such as agricultural material or civil engineering material.

Examples of the organic filler include native starch, modified starch, pulp, chitin-chitosan, coconut shell flour, wood powder, bamboo powder, bark powder, kenaf powder, and straw powder. These powders may be used either singly or as a mixture of two or more of them. The amount of the organic filler is typically from 0.01 to 70 wt. % based on the total weight of the composition. Particularly, the organic filler remains in the soil and plays a role as a soil improver or fertilizer after biodegradation of the polyester composition so that it enhances the role of the composition as green plastic.

To the production of the composition, any conventionally known mixing/kneading technology can be applied. As a mixer, horizontal cylindrical type, V-shaped type and double conical type mixers, blenders such as ribbon blender and super mixer, and various continuous mixers are usable. As a kneader, batch kneaders such as roll and internal mixer, one-stage and two-stage continuous kneaders, twin screw extruder and single screw extruder are usable. Examples of the kneading method include a method of melting the composition under heating, adding each additive, filler or thermoplastic resin to the molten composition, and kneading the mixture. A blending oil may be added in order to disperse the various additives uniformly.

The polyester or composition thereof according to the present invention can be molded by various molding methods employed for general-purpose plastics. Examples include compression molding (compression molding, lamination molding, stampable molding), injection molding, extrusion or co-extrusion (film extrusion using inflation or T-die method, lamination, sheet extrusion, pipe extrusion, wire/cable extrusion, profile extrusion), hollow molding (blow molding of every kind), calendering, foam molding (melt foam molding, solid-phase foam molding), solid forming (uniaxial stretching, biaxial stretching, rolling, formation of oriented nonwoven cloth, thermoforming (vacuum forming, compression air forming, plastic forming), powder molding (rotation molding), and nonwoven fabric forming (dry method, adhesion method, entanglement method, spunbond method, and the like).

The polyester or composition thereof according to the present invention may be subjected to secondary processing suited for various purposes in order to impart it with surface functions such as chemical function, electrical function, magnetic function, mechanical function, friction/abrasion/lubrication function, optical function, thermal function or biocompatibility. Examples of the secondary processing include embossing, painting, adhesion, printing, metalizing (plating or the like), mechanical processing, and surface treatment (antistatic treatment, corona discharge treatment, plasma treatment, photochromism treatment, physical vapor deposition, chemical vapor deposition, coating or the like).

By the above-described molding methods, various molded products such as monolayer film, multilayer film, stretched film, shrink film, laminate film, monolayer sheet, multilayer sheet, stretched sheet, pipe, wire/cable, monofilament, multifilament, various nonwoven fabrics, flat yarn, staple, crimped fibers, stretched tape or band, striated tape, split yarn, composite fibers, blow bottle and foam. The molded products thus obtained are expected to be used for shopping bags, garbage bags, various films such as agricultural films, various containers such as cosmetic containers, detergent containers, food container, and containers for bleaching agent, fishing lines, fish nets, ropes, binding materials, surgical yarns, sanitary cover stock materials, cooling boxes, buffer materials, medical materials, electric appliance materials, chassis for household electric appliances and automobile materials.

EXAMPLES

The present invention will hereinafter be described more specifically. It should however be borne in mind that the present invention is not limited to or by these Examples without departing from the scope of the present invention.

The characteristic values in the following examples were measured by the following methods. The term ppm as used herein means mass ppm.

Dilute solution viscosity (reduced viscosity): Polyester was dissolved in phenol/tetrachloroethane (1/1 (mass ratio) mixture) so as to give its concentration of 0.5 g/dL and time t (sec) required for falling of the resulting solution through a viscosity tube in a temperature-controlled bath of 30° C. was measured. In addition, time to (sec) required for falling of the solvent alone was also measured at 30° C. and a reduced viscosity $\eta_{sp}/C$ $(=(t-t_0)/t_0 \cdot C)$ was calculated (C represents the concentration of the solution).

Nitrogen atom content: 10 ag of a sample was weighed on a quartz boat. It was burnt using a total nitrogen analyzer (TN-10, product of Mitsubishi Chemical) and a nitrogen atom content of it was determined by chemiluminescence.

Sulfur atom content: About 0.1 g of a sample was weighed on a platinum boat. It was burned in a quartz tubular furnace AQF-100 (concentration system) (product of Mitsubishi Chemical). A sulfur content in the combustion gas was caused to absorb by a 0.1% aqueous solution of hydrogen peroxide. The sulfate ion in the resulting solution was then measured using ion chromatography (ICS-1000, product of Dionex).

Water containing amount (water content): After water was evaporated from 0.5 g of a sample by heating and melting at 200° C. in a moisture vaporizer (VA-100, product of Mitsubishi Chemical), a total water content thus evaporated was determined in accordance the coulometric titration based on the principle of Karl Fischer reaction by using a trace moisture meter (CA-100, product of Mitsubishi Chemical).

Amount of terminal carboxyl groups: It was determined by dissolving the resulting polyester in benzyl alcohol, followed by titration with 0.1N NaOH. It was a carboxyl equivalent per $1 \times 10^6$ g.

YI: It was determined in accordance with the method of JIS K7105.

Referential Example 1

<Construction of Gene Disruption Vector>
(A) Extraction of *Bacillus subtilis* Genomic DNA

*Bacillus subtilis* (ISW1214) was cultured in 10 mL of an LB medium [composition: obtained by dissolving 10 g of tryptone, 5 g of yeast extract and 5 g of NaCl in 1 L of distilled water] until a late logarithmic growth phase and bacterial cells thus grown-were collected. The resulting bacterial cells were suspended in 0.15 mL of a solution containing a 10 mM NaCl/20 mM Tris buffer (pH 8.0)/1 mM EDTA·2Na solution containing lysozyme to give its concentration of 10 mg/mL.

Next, Proteinase K was added to the resulting suspension to give its final concentration of 100 μg/mL and the resulting mixture was kept at 37° C. for 1 hour. Sodium dodecyl sulfate solution was then added to give its final concentration of 0.5% and the mixture was kept at 50° C. for 6 hours to cause bacteriolysis. After addition of an equal amount of phenol/chloroform solution to the resulting lysate solution and mild shaking at room temperature for 10 minutes, the whole amount of the mixture was centrifuged (5,000×g, 20 minutes, from 10 to 12° C.). The supernatant fraction was collected and sodium acetate solution was added to the supernatant fraction at a concentration of 0.3M. To the resulting mixture was added two times the amount of ethanol, followed by mixing. The precipitate obtained by centrifugation (15,000×g, 2 minutes) was washed with 700 ethanol, and then air-dried. To the resulting DNA was added 5 mL of a 10 mM tris buffer (pH 7.5)-1 mM EDTA·2Na solution. The resulting mixture was allowed to stand overnight at 4° C. and then, used as a template DNA for PCR performed later.

(B) Amplification and Cloning of Sacs Gene by PCR

A *Bacillus subtilis* SacB gene was obtained by performing PCR using the DNA prepared in the above (A) as a template and synthetic DNAs (SEQ ID NO: 1 and SEQ ID NO: 2) designed based on the nucleotide sequence of the gene (GenBank Database Accession. No. X02730) which had already been reported.

Composition of reaction liquid: 1 μL of the template DNA, 0.2 μL of PfxDNA polymerase (product of Invitrogen), 1-fold concentration of a supplied buffer, 0.3 μM of each of primers, 1 mM MgSO₄, and 0.25 μM dNTPs were mixed to give a total volume of 20 μL.

Reaction temperature condition: DNA Thermal Cycler PTC-200 (product of MJ Research) was used and a cycle composed of 94° C. for 20 seconds and 60° C. for 2 minutes was repeated for 35 times. Heat retention at 94° C. at the first cycle was conducted for 1 minute and 20 seconds, while heat retention at 68° C. at the last cycle was conducted for 5 minutes.

Confirmation of the amplified product was performed by separation by 0.751 agarose (SeaKem GTG agarose: product of FMC BioProducts) gel electrophoresis, followed by visualization with ethidium bromide staining, whereby a fragment of about 2 kb was detected. The target DNA fragment was recovered from the gel by using QIAQuick Gel Extraction Kit (product of QIAGEN).

After phosphorylation of the 5'-end of the recovered DNA fragment with T4 Polynucleotide Kinase (product of Takara Shuzo), the resulting fragment was inserted into the EcoRV site of an *Escherichia coli* vector (pBluescript II, product of STRATEGENE) by using Ligation Kit ver. 2 (product of Takara Shuzo), and with the plasmid DNA thus obtained, *Escherichia coli* (DH5α strain) was transformed. The recombinant *Escherichia coli* obtained in such a manner was smeared onto an LB agar medium [obtained by dissolving 10 g of tryptone, 5 g of yeast extract, 5 g of NaCl, and 15 g of agar in 1 L of distilled water] containing 50 μg/mL ampicillin and 50 μg/mL X-Gal.

Clones which had formed a white colony on the medium were transferred to an LB agar medium containing 50 μg/mL ampicillin and 100 sucrose and were cultured at 37° C. for 24 hours. Of those clones, those which failed to grow on the medium containing sucrose were subjected to liquid culture in a conventional manner, followed by the formation of the plasmid DNA. A strain permitting functional expression of an SacB gene in *Escherichia coli* must be incapable of growing in the sucrose-containing medium. The plasmid INA thus obtained was digested with restriction enzymes SalI and PstI. The plasmid MOL thus obtained was confirmed to have an inserted fragment of about 2 kb and the plasmid was named pBS/SacB.

(C) Construction of Chloramphenicol-Resistant SacB Vector 500 ng of *Escherichia coli* plasmid vector pHSG396 (chloramphenicol resistant marker, product of Takara Shuzo) was reacted with 10 units of restriction enzyme PshBI at 37° C. for 1 hour, followed by recovery by phenol/chloroform extraction and ethanol precipitation. After blunting of the both ends with Klenow Fragment (product of Takara Shuzo), ligation with MluI linker (product of Takara Shuzo) by using Ligation Kit ver. 2 (product of Takara Shuzo) and circularization, *Escherichia coli* (DH5α strain) was transformed. The recombinant *Escherichia coli* thus obtained was smeared onto an LB agar medium containing 34 µg/mL chloramphenicol. A plasmid DNA was isolated from the resulting clones in a conventional manner. A clone having a cleavage site of a restriction enzyme MluI was selected and named pHSG396Mlu.

On the other hand, pBS/SacB thus constructed in the above (B) was digested with restriction enzymes SalI and PstI and then, the both ends thereof were blunted with the Klenow Fragment. The MluI linker was ligated by using Ligation Kit ver. 2 (product of Takara Shuzo). A DNA fragment of about 2.0 kb containing a SacB gene was then separated by 0.75% agarose gel electrophoresis and then, recovered. The resulting SacB gene fragment was ligated to the pHSG396Mlu fragment, which had been digested with restriction enzyme MluI and then dephosphorylated, at the end of the fragment, with Alkaline Phosphatase Calf intestine (product of Takara Shuzo), by using Ligation Kit ver. 2 (product of Takara Shuzo), whereby *Escherichia coli* (DH5α strain) was transformed. The recombinant *Escherichia coli* thus obtained was smeared onto an LB agar medium containing 34 g/mL chloramphenicol. The colonies thus obtained were transferred to an LB agar medium containing 34 µg/mL chloramphenicol and 100 sucrose, and cultured at 37° C. for 24 hours. Plasmid DNA was isolated in a Conventional manner from the clones which had failed to grow on the sucrose-containing medium among these clones. The plasmid DNA thus obtained was analyzed by digestion with MluI. As a result, the plasmid DNA was confirmed to have an inserted fragment of about 2.0 kb and it was named pCMB1.

(D) Acquisition of Kanamycin-Resistant Gene

A kanamycin-resistant gene was obtained by PCR using a DNA of *Escherichia coli* plasmid vector pHSG299 (kanamycin resistant marker: product of Takara Shuzo) as a template and synthetic DNAs shown in SEQ ID NO: 3 and SEQ ID NO: 4 as primers.

Composition of reaction liquid: 1 ng of the template DNA, 0.1 µL of Pyrobest DNA polymerase (product of Takara Shuzo), 1-fold concentration of a supplied buffer, 0.5 µM of each primer, and 0.25 µM dNTPs were mixed to give a total amount of 20 µL.

Reaction temperature condition: DNA Thermal Cycler PTC-200 (product of MJ Research) was used and a cycle composed of 94° C. for 20 seconds, 62° C. for 15 seconds, and 72° C. for 1 minute and 20 seconds was repeated 20 times. Heat retention at 94° C. at the first cycle was conducted for 1 minute and 20 seconds, while heat retention at 72° C. at the last cycle was conducted for 5 minutes.

Confirmation of the amplified product was performed by separation by 0.75% agarose (SeaKem GTG agarose: product of FMC BioProducts) gel electrophoresis, followed by visualization with ethidium bromide staining, whereby a fragment of about 1.1 kb was detected. The target D fragment was recovered from the gel by using QIAQuick Gel Extraction Kit (product of QIAGEN). A 5'-end of the DNA fragment thus recovered was phosphorylated with T4 Polynucleotide Kinase (product of Takara Shuzo).

(E) Construction of Kanamycin-Resistant SacB Vector

A DNA fragment of about 3.5 kb obtained by digesting, with restriction enzymes Van91I and ScaI, the pCMB1 constructed in the above (C) was separated by 0.75% agarose gel electrophoresis and, then recovered. The resulting DNA fragment was mixed with the kanamycin resistant gene prepared in the above (D) and ligated thereto by using Ligation Kit ver. 2 (product of Takara Shuzo). With the plasmid DNA thus obtained, *Escherichia coli* (DH5α strain) was transformed. The recombinant *Escherichia coli* thus obtained was smeared onto an LB agar medium containing 50 g/mL kanamycin.

It was confirmed that the strain grown on the kanamycin-containing medium had failed to grow on the sucrose-containing medium. The plasmid D prepared from the strain was digested with restriction enzyme HindIII to generate Fragments of 354, 473, 1807, and 1997 bp, suggesting that the plasmid DNA definitely had a structure as illustrated in FIG. 1. The plasmid was named pXMB1.

Reference Example 2

<Construction of LDH Gene Disrupted Strain>
(A) Extraction of Genomic DNA from *Brevibacterium flavum* MJ233-ES Strain A *Brevibacterium flavum* MJ-233 strain was cultured until a late logarithmic growth phase in 10 mL of medium A (obtained by dissolving 2 g of urea, 7 g of $(NH_4)_2SO_4$, 0.5 g of $KH_2PO_4$, 0.5 g of $K_2PO_4$, 0.5 g of $MgSO_4·7H_2O$, 6 mg of $FeSO_4·7H_2O$, 6 mg of $MnSO_4·4-5H_2O$, 200 µg of biotin, 100 µg of thiamine, 1 g of yeast extract, 1 g of casamino aid, and 20 g of glucose in 1 L of distilled water). A genomic DNA was prepared using the cells thus obtained by the method as described above in (A) of Referential Example 1.

(B) Cloning of Lactate Dehydrogenase Gene

A lactate dehydrogenase gene of MJ233 strain was obtained by PCR using the DNA prepared in the above (A) as a template and synthetic DNAs (SEQ ID NO: 5 and SEQ ID NO: 6) designed based on the nucleotide sequence of the gene described in Japanese Patent Laid-Open No. Hei 11-206305.

Composition of reaction liquid: 1 µL of the template DNA, 0.2 µL of TaqDNA polymerase (product of Takara Shuzo), 1-fold concentration of an attached buffer, 0.2 g t of each primer, and 0.25 µM of dNTPs were mixed to give a total amount of 20 µL.

Reaction temperature conditions By using DNA Thermal Cycler PTC-200 (product of MJ Research), a cycle composed of 94° C. for 20 seconds, 55° C. for 20 seconds, and 72° C. for 1 minute was repeated 30 times. Heat retention at 94° C. at the first cycle was conducted for 1 minute and 20 seconds, while heat retention at 72° C. at the last cycle was conducted for 5 minutes.

Confirmation of the amplified product was performed by separation by 0.75% agarose (SeaKem GTG agarose: product of FMC BioProducts) gel electrophoresis and visualization with ethidium bromide staining, whereby a fragment of about 0.95 kb was detected. The target DNA fragment was recovered from the gel by using QIAQuick Gel Extraction Kit (product of QIAGEN).

The DNA fragment thus recovered was mixed with a PCR product cloning vector pGEM-TEasy, (product of Promega) and ligated thereto using Ligation Kit ver. 2 (product of Takara Shuzo). *Escherichia coli* (DH5α strain) was then transformed using the resulting plasmid DNA. The recombinant *Escherichia coli* thus obtained was smeared onto an LB agar medium containing 50 µg/mL ampicillin and 50 µg/mL X-Gal.

Clones which had formed a white colony on the medium were subjected to liquid culture in a conventional manner, and then the plasmid DNA was purified. The resulting plasmid DNA was digested with restriction enzymes SacI and SphI, whereby an inserted fragment of about 1.0 kb was recognised and it was named pGEMT/CgLDH.

(C) Construction of Plasmid for Disrupting Lactate Dehydrogenase Gene

By digestion of the pGEMT/CgLDH prepared in the above (B) with restriction enzymes EcoRV and XbaI, a coding region of lactate dehydrogenase of about 0.25 kb was cut out. By blunting the end of the remaining DNA fragment of about 3.7 kb by the Klenow Fragment and circularizing it using Ligation Kit ver. 2 (product of Takara Shuzo), *Escherichia coli* (DH5α strain) was transformed. The recombinant *Escherichia coli* thus obtained was smeared onto an LB agar medium containing 50 sg/mL ampicillin. The strain grown on the medium was subjected to liquid culture in a conventional manner, and then the plasmid DNA was purified. The resulting plasmid DNA was digested with restriction enzymes SacI and SphI. A clone which was recognized to have an inserted fragment of about 0.75 kb was selected and it was named pGEMT/ΔLDH.

Next, the MA fragment of about 0.75 kb obtained by digesting the pGEMT/ΔLDH with the restriction enzymes SacI and SphI was separated by 0.75% agarose gel electrophoresis and recovered to prepare a lactate dehydrogenase gene fragment containing a defective region. The resulting DNA fragment was mixed with the pKMB1 constructed in Referential Example 1 by digestion with the restriction enzymes SacI and SphI, and ligated thereto by using Ligation Kit ver. 2 (product of Takara Shuzo). With the plasmid DNA thus obtained, *Escherichia coli* (DH5α strain) was transformed. The recombinant *Escherichia coli* thus obtained was smeared onto an LE agar medium containing 50 µg/mL of kanamycin and 50 µg/mL of X-Gal.

Figure 2:
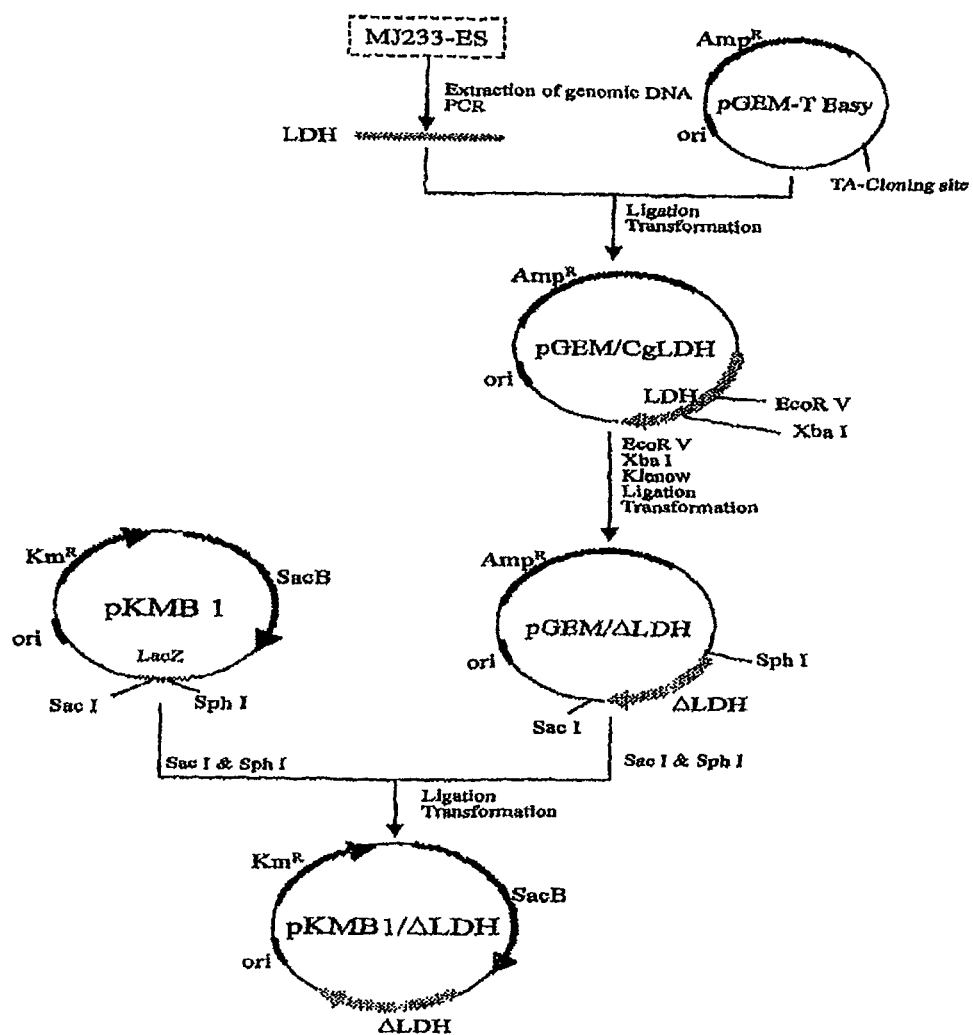
FIG. 2 schematically illustrates the construction of pKMB1/ΔLDH.

After clones which had formed a white colony on the medium were subjected to liquid culture in a conventional manner, the plasmid DNA was purified. By digesting the plasmid DNA thus obtained with restriction enzymes SacI and SphI, a clone having an inserted fragment of about 0.75 kb was selected and named pKMB1/ΔLDH (FIG. 2).

(D) Construction of Lactate Dehydrogenase Gene-Disrupted Strain Derived from *Brevibacterium flavum* MJ233-ES Strain A plasmid DNA to be used for transformation of the *Brevibacterium flavum* MJ-233 strain was prepared from an *Escherichia coli* JM110 strain transformed with pKMB1/ΔLDH by a calcium chloride method (*Journal of Molecular Biology*, 53, 159, 1970).

The transformation of the *Brevibacterium flavum* MJ233-ES strain was performed by an electric pulse method (*Res. Microbiol.*, Vol. 144, p. 181-185, 1993), and the resulting transformant was smeared onto an LBG agar medium [obtained by dissolving 10 g of tryptone, 5 g of yeast extract, 5 g of NaCl, 20 g of glucose, and 15 g of agar in 1 L of distilled water) containing 50 µg/mL kanamycin.

Since pKMB1/ΔLDH was an unreplicable plasmid in the *Brevibacterium flavum* MJ233-ES strain, homologous recombination was caused between a lactate dehydrogenase gene on the plasmid and the same gene on the genome of the *Brevibacterium flavum* MJ-233 strain. As a result, the strain grown on the above-described medium must have, on the genome thereof, a kanamycin-resistant gene and SacB gene derived from the plasmid.

Next, the strain obtained by homologous recombination was subjected to liquid culture on an LBG medium containing 50 µg/mL kanamycin. The culture solution corresponding to about 1000000 cells was smeared onto an LBG medium containing 10% sucrose. As a result, about 10 strains which were presumed to be sucrose-insensitive as a result of loss of the SacB gene caused by the second homologous recombination were obtained.

The strains thus obtained include a strain in which the lactate dehydrogenase gene has been replaced by a mutation type derived from pKMB1/ΔLDH and a strain in which the lactate dehydrogenase gene has been reverted to a wild type. Whether the lactate dehydrogenase gene is a mutation type or a wild type can be confirmed easily by subjecting a cell obtained by liquid culture in an LBG medium to direct PCR and detecting the lactate dehydrogenase gene. Analysis of the lactate dehydrogenase gene by using PCR amplification primers (SEQ ID NO: 7 and SEQ ID NO: 8) may reveal that the wild type has a DNA fragment of 720 bp and a mutation type having a depletion region has a DNA fragment of 471 bp.

As a result of analysis of the sucrose-insensitive strain by the above-mentioned method, a strain having only a mutation type gene was selected and the strain was named *Brevibacterium flavum* MJ233/ΔLDH.

(E) Confirmation of Lactate Dehydrogenase Activity

*Brevibacterium flavum* MJ233/ΔLDH strain prepared by the above (D) was inoculated into medium A and then aerobically cultured at 30° C. for 15 hours with shaking. The resulting culture was centrifuged (3,000×g, 4° C. for 20 minutes). The cells were collected and then, washed with a sodium-phosphate buffer [composition: 50 mM sodium phosphate buffer (pH 7.3)).

Then, 0.5 g (wet weight) of the washed cells was suspended in 2 mL of the sodium-phosphate buffer. The resulting suspension was subjected to a ultrasonicator (product of Branson) while ice cooling, whereby cell debris was obtained. The resulting cell debris was centrifuged (10,000× g, 4° C. for 30 minutes) and the supernatant was then obtained as a crude enzyme solution. Similarly, a crude enzyme solution of *Brevibacterium flavum* MJ233-ES strain was prepared as a control and then subjected to the following activity measurement.

The enzymatic activity of lactate dehydrogenase was confirmed by measuring, as a change in absorbance at 340 nm, oxidation of coenzyme NADH to NAD$^+$ caused by lactic acid generated using pyruvic acid as a substrate [L. Kanarek and R. L. Hill, *J. Biol. Chem.* 239, 4202 (1964)]. The reaction was effected at 37° C. in the presence of 50 mM potassium-phosphate buffer (pH 7.2), 10 mx pyruvic acid and 0.4 mM NADH. Consequently, the lactate dehydrogenase activity of the crude enzyme solution prepared from *Brevibacterium flavum* MJ233/ΔLDH strain was one tenth or less of the lactate dehydrogenase activity of the crude enzyme solution prepared from *Brevibacterium flavum* MJ233-ES strain.

Referential Example 3

<Construction of Coryneform Bacteria Expression Vector>

(A) Preparation of Promoter Fragment for Coryneform Bacteria

A DNA fragment (which will hereinafter be called T24 promoter) of coryneform bacteria shown in SEQ ID NO: 4 in Japanese Patent Laid-Open No. Hei 7-95891 and reported to have high promoter activity was used. The promoter fragment was obtained by PCR using the *Brevibacterium flavum* MJ233 genomic DNA prepared in (A) of Referential Example 2 as a template and synthetic DNAs (SEQ ID NO: 9 and SEQ ID NO: 10) designed based on a sequence described as SEQ ID NO: 4 in Japanese Patent Laid-Open No. Hei 7-95891.

Composition of reaction liquid: 1 µL of the template DNA, 0.2 µL of PfxDNA polymerase (product of Invitrogen Japan), 1-fold concentration of an attached buffer, 0.3 µM of each primer, 1 mM of MgSO$_4$, and 0.25 pH dNTPs were mixed to give a total volume of 20 μL.

Reaction temperature condition: DNA Thermal Cycler PTC-200 (product of MJ Research) was used and a cycle composed of 94° C. for 20 seconds, 60° C. for 20 seconds, and 72° C. for 30 seconds was repeated 35 times. Heat retention at 94° C. at the first cycle was conducted for 1 minute and 20 seconds while heat retention at 72° C. at the final cycle was conducted for 2 minutes.

Confirmation of the amplified product was performed by separation by 2.0% agarose (SeaKem GTG agarose: product of FMC BioProducts) gel electrophoresis and visualization with ethidium bromide staining, whereby a fragment of about 0.25 kb was detected. The target DNA fragment was recovered from the gel by using QIAQuick Gel Extraction Kit (product of QIAGEN).

The 5'-end of the recovered DNA fragment was phosphorylated with T4 Polynucleotide Kinase (product of Takara Shuzo) and was ligated to an SmaI site of an *Escherichia coli* vector pUC 19 (Takara Shuzo) by using Ligation Kit ver. 2 (product of Takara Shuzo). With the plasmid DNA thus obtained, *Escherichia coli* (DH5α strain) was transformed. The resulting recombinant *Escherichia coli* was smeared onto an LB agar medium containing 50 μg/mL ampicillin and 50 μg/mL X-Gal.

After six clones which had formed a white colony on the resulting medium were subjected to liquid culture in a conventional manner, the plasmids DNA were purified and the base sequences thereof were determined, respectively. A clone having a TZ4 promoter inserted therein so as to have transcription activity in a direction opposite to the lac promoter on pUC 19 was selected from them and it was named pUC/TZ4.

Next, a DNA linker composed of synthetic DNAs (SEQ ID NO: 11 and SEQ ID NO: 12) each having a phosphorylated 5'-end and having, at both ends, cohesive ends corresponding to BamHI and PstI was mixed with the DNA fragment prepared by digesting the pUC/TZ4 with restriction enzymes BamHI and PstI to ligate them each other by using Ligation Kit ver. 2 (product of Takara Shuzo). With the plasmid DNA thus obtained, *Escherichia coli* (DH5α strain) was transformed. The above-described MM linker includes a ribosome binding sequence (AGGAGG) and a cloning site (PacI, NotI, and ApaI arranged in this order from upstream) downstream of the ribosome binding sequence.

Clones which had formed, a white colony on the medium were subjected to liquid culture in a conventional manner, and then the plasmids DNA were purified, respectively. A plasmid DNA capable of being digested with restriction enzyme NotI was selected from the plasmids DNA thus obtained and it was named pUC/TZ4-SD.

A promoter fragment of about 0.3 kb obtained by digesting the pUC/TZ4-SD thus constructed with a restriction enzyme PstI, blunted at the end thereof with the Klenow Fragment, and digested with restriction enzyme KpnI was separated by 2.0% agarose gel electrophoresis and then, recovered.

(B) Construction of expression Vector for Coryneform bacteria pHSG298par-rep described in Japanese Patent Laid-Open No. Hei 12-93183 was used as a plasmid replicable autonomously and stably in coryneform bacteria. The plasmid is equipped with a replication region and a stabilization-function-having region of a natural plasmid pBY503 that *Brevibacterium stationis* IF012144 strain possesses, and a kanamycin resistant gene and a replication region of *Escherichia coli* derived from *Escherichia coli* vector pHSG298 (Takara Shuzo). DNA prepared by digesting the pHSG298par-rep with a restriction enzyme SseI, blunting its ends with the Klenow Fragment, and digesting it with a restriction enzyme KpnI was mixed with the TZ4 promoter fragment prepared in the above (A) and ligated thereto by using Ligation Kit ver. 2 (product of Takara Shuzo). With the plasmid DNA thus obtained, *Escherichia coli* (DH5α strain) was transformed. The resulting recombinant *Escherichia coli* was smeared onto an LB agar medium containing 50 μg/mL kanamycin.

Figure 3:
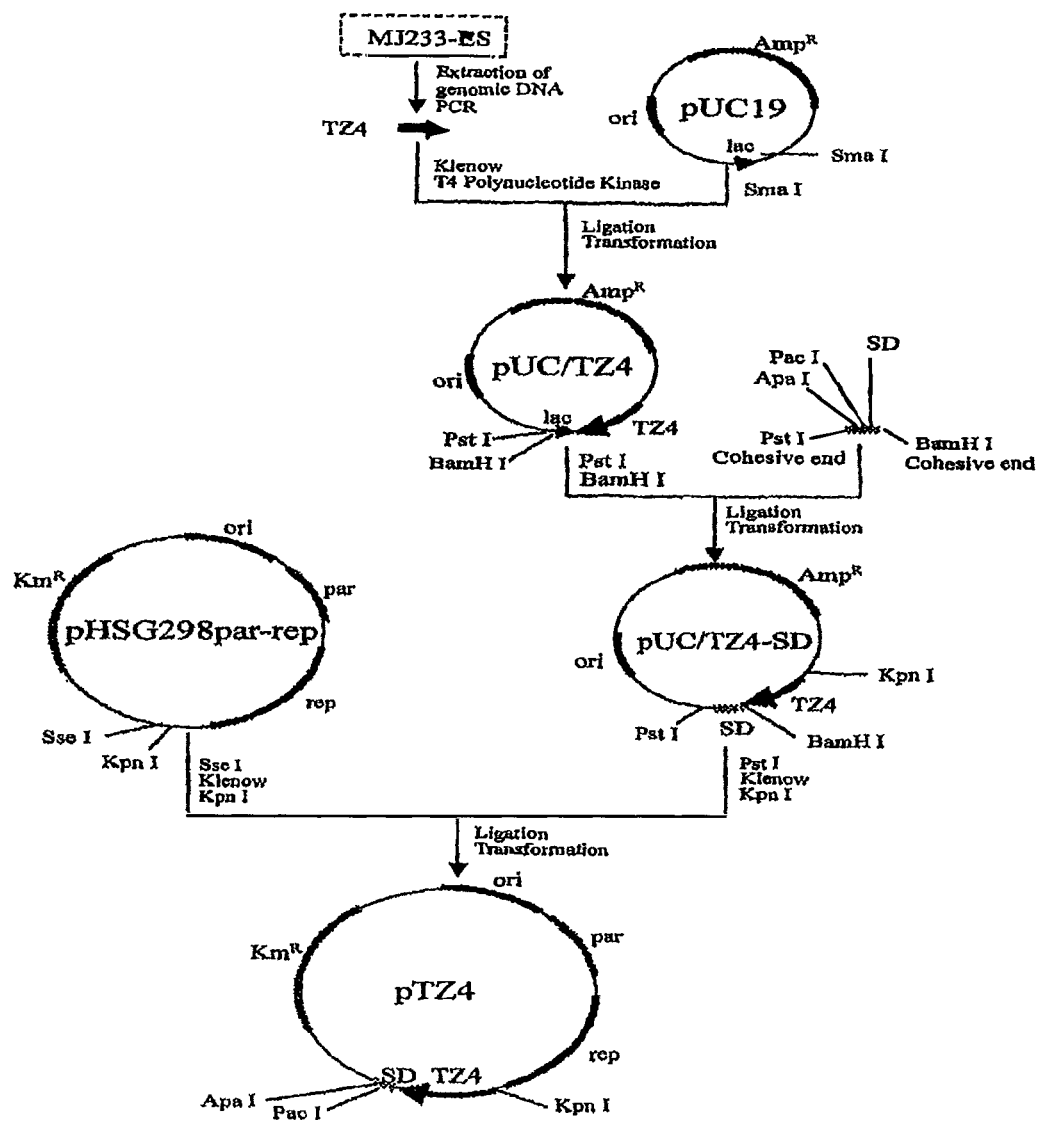
FIG. 3 schematically illustrates the construction of a pTZ vector.

After the strains grown on the resulting medium were subjected to liquid culture in a conventional manner, the plasmid DNAs were purified. Of the plasmid DNAs, a plasmid DNA capable of being digested with restriction enzyme NotI was selected and it was named pTZ4 (FIG. 3 shows the construction procedure).

Referential Example 4

<Construction of Pyruvate Carboxylase Activity-Enhanced Strain>

(A) Acquisition of Pyruvate Carboxylase Gene

A pyruvate carboxylase gene derived from the *Brevibacterium flavum* MJ233 strain was obtained by PCR using the DNA prepared in the above (A) of Referential Example 2 as a template and synthetic DNAs (SEQ ID NO: 13 and SEQ ID NO: 14) designed based on the sequence (GenBank Database Accession No. AP005276) of the pyruvate carboxylase gene of a *Corynebacterium glutamicum* ATCC 13032 strain whose entire genomic sequence had been reported.

Composition of reaction liquid: 1 μL of the template DNA, 0.2 μL of PfxDNA polymerase (product of Invitrogen), 1-fold concentration of an attached buffer, 0.3 μM of each primer, 1 mM MgSO$_4$, and 0.25 WM dNTPs were mixed to give a total volume of 20 μL.

Reaction temperature condition: DNA Thermal Cycler PTC-200 (product of MJ Research) was used and a cycle composed of 94° C. for 20 seconds and 68° C. for 4 minutes was repeated 35 times. Heat retention at 94° C. at the first cycle was conducted for 1 minute and 20 seconds, while heat retention at 68° C. at the final cycle was conducted for 10 minutes. After completion of PCR reaction, 0.1 μL of Takara Ex Taq (Takara Shuzo) was added and the mixture was kept further at 72° C. for 30 minutes.

Confirmation of the amplified product was performed by separation by 0.750 agarose (SeaKem GTG agarose: product of FMC BioProducts) gel electrophoresis and visualization with ethidium bromide staining, whereby a fragment of about 3.7 kb was detected. The target DNA fragment was recovered from the gel by using QIAQuick Gel Extraction Kit (product of QIAGEN).

The DNA fragment thus recovered was mixed with PCR product-cloning vector pGM-TEasy (product of Promega) and ligated thereto using Ligation Kit ver. 2 (product of Takara Shuzo). *Escherichia coli* (DH5α strain) was then transformed using the resulting plasmid DNA. The recombinant *Escherichia coli* thus obtained was smeared onto an LB agar medium containing 50 μg/mL ampicillin and 50 μg/mL X-Gal.

After the clone which had formed a white colony on the medium was subjected to liquid culture in a conventional manner, the plasmid DNA was purified. The resulting plasmid DNA was digested with restriction enzymes PacI and ApaI, whereby an inserted fragment of about 3.7 kb was recognized and it was named pGEM/MJPC.

A base sequence of the inserted fragment in pGEM/MJPC was determined by using the base sequencing device (model 377 XL) and BigDye Terminator Cycle Sequencing Nit ver. 3, each, product of Applied Biosystems. The base sequence thus obtained and a predicted amino acid sequence are described in SEQ. ID NO: 15 and only the amino acid sequence is shown in SEQ. ID NO: 16. The amino acid sequence showed a very high homology (99.40) to that derived from the *Corynebacterium glutamicum* ATCC 13032 strain so that it was concluded that the PGEM/MJPC insert fragment was a pyruvate carboxylase gene derived from the *Brevibacterium flavum* MJ233 strain.

(3) Construction of Plasmid for Enhancing Pyruvate Carboxylase Activity

The pyruvate carboxylase gene fragment of about 3.7 kb obtained by digesting the pGEM/MJPC, which had been prepared in the above (A), with the restriction enzymes PacI and ApaI was separated by 0.75% agarose gel electrophoresis and then, recovered.

The resulting DNA fragment was mixed with pTZ4, which had been constructed by digestion with restriction enzymes PacI and Apa1 in Referential Example 3, and ligated thereto by using Ligation Kit ver. 2 (product of Takara Shuzo). With the plasmid DNA thus obtained, *Escherichia coli* (DH5α strain) was transformed. The resulting recombinant *Escherichia coli* was smeared onto an LB agar medium containing 50 sg/mL kanamycin.

Figure 4:
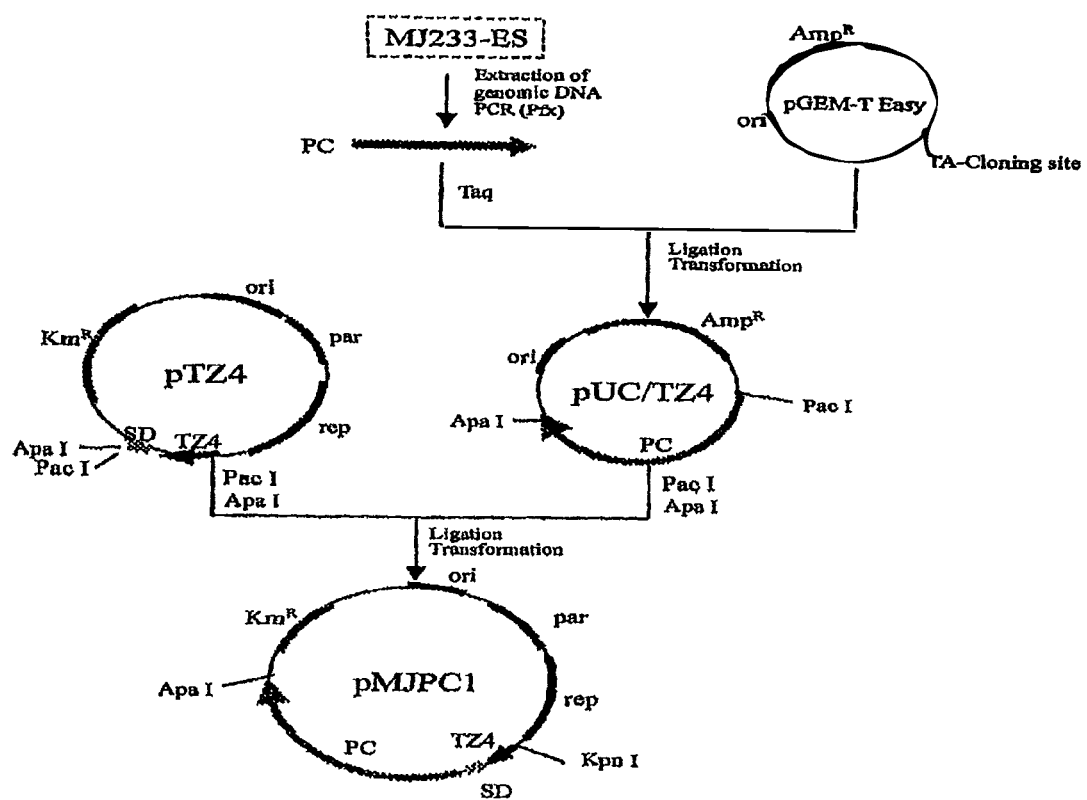
FIG. 4 schematically illustrates the construction of pMJPC1.

After the strains grown on the medium were subjected to liquid culture in a conventional manner, the plasmid DNA was purified. The plasmid DNA thus obtained was digested with restriction enzymes PacI and ApaI. A plasmid having an inserted fragment of about 3.7 kb was selected and named pMJPC1 (FIG. 4).

(C) Transformation to *Brevibacterium flavum* MJ233/ΔLDH Strain

A plasmid DNA replicable in the *Brevibacterium flavum* MJ233 strain and used for transformation by pMJPC1 was prepared from the *Escherichia coli* (DH5a strain) transformed in the above (B).

The transformation to a *Brevibacterium flavum* MJ233/ ΔLDH strain was performed by the electric pulse method (*Res. Microbiol., Vol.* 144, p. 181-185, 1993). The transformant thus obtained was smeared onto an LBG agar medium [obtained by dissolving 10 g of tryptone, 5 g of yeast extract, 5 g of NaCl, 20 g of glucose, and 15 g of agar in 1 L of distilled water] containing 50 μg/mL kanamycin.

After the strain which had grown on the medium was subjected to liquid culture in a conventional manner, a plasmid DNA was extracted. As a result of analysis by digestion with a restriction enzyme, it was confirmed that the strain retained pMJPC1, and the strain was named *Brevibacterium flavum* MJ233/PC/ΔLDH strain.

(D) Pyruvate Carboxylase Enzymatic Activity

The transformant strain *Brevibacterium flavum* MJ233/ PC/ΔLDH obtained in the above (C) was cultured overnight in 100 ml of medium A containing 20 glucose and 25 mg/l kanamycin. After harvesting of the cells thus obtained, they were washed with 50 ml of 50 mM potassium phosphate buffer (pH 7.5), followed by re-suspension in 20 al of a buffer having a similar composition thereto. The suspension was subjected to sonication with SONIFIER 350 (product of Branson) and the centrifuged supernatant was then provided as a cell-free extract. The pyruvate carboxylase activity was determined using the resulting cell-free extract. The measurement of enzymatic activity was carried out by allowing the enzyme to react at 25° C. in a reaction solution containing 100 MH Tris/HCL buffer (pH 7.5), 0.1 mg/10 al biotin, 5 mM magnesium chloride, 50 mM sodium hydrogen carbonate, 5 mM sodium pyruvate, 5 mM adenosine triphosphate sodium, 0.32 mM NADH, 20 units/1.5 ml malate dehydrogenase (product of WAKO, originated from yeast). One unit (1 U) was defined as the amount of enzyme for catalyzing a decrease of 1 μmol of NADH per minute. The specific activity in the cell-free extract in which pyruvate carboxylase had been expressed was 0.2 U/mg of protein. On the other hand, from the calls prepared similarly by incubating the parent MJ233/ΔLDH strain by using medium A, no pyruvate carboxylase activity was detected by the activity measurement method.

Referential Example 5

<Preparation of Fermentation Liquid>

100 mL of a medium having a composition of 4 g of urea, 14 g of ammonium sulfate, 0.5 g of monobasic potassium phosphate, 0.5 g of dibasic potassium phosphate, 0.5 g of magnesium sulfate·7 hydrate, 20 mg of ferrous sulfate·7 hydrate, 20 mg of manganese sulfate-hydrate, 200 μg of D-biotin, 200 μg of thiamin hydrochloride, 1 g of yeast extract, 1 g of casamino acid, and 1000 ml of distilled water was charged in a 500-mL conical flask and then sterilized by heating at 120° C. for 20 minutes. The resulting medium was cooled to room temperature, followed by the addition thereto of 4 mL of a 50% aqueous glucose solution sterilized in advance and 50 μL of a 5% kanamycin solution subjected to aseptic filtration. The *Brevibacterium flavum* MJ233/PC/ ΔLDH strain prepared in Referential Example 4 (C) was inoculated to the resulting medium and seed culture was carried out at 30° C. for 24 hours.

A medium containing 12 g of urea, 42 g of ammonium sulfate, 1.5 q of monobasic potassium phosphate, 1.5 g of dibasic potassium phosphate, 1.5 g of magnesium sulfate·7 hydrate, 60 mg of ferrous sulfate·7 hydrate, 60 mg of manganese sulfate·hydrate, 600 μg of D-biotin, 600 μg of thiamin hydrochloride, 3 g of yeast extract, 3 g of casamino acid, 1 ml of antifoaming agent (Adecanol LG294: product of Asahi Denka), and 2500 mL of distilled water was charged in a 5-L fermenter, and sterilized by heating at 120° C. for 20 minutes. After cooling to room temperature, 500 mL of a 120 aqueous glucose solution sterilised in advance was added. To the resulting mixture was added the whole amount of the seed culture solution obtained above and the mixture was kept at 30° C. The main culture was carried out with aeration at a rate of 500 mL per minute and agitation at a rate of 500 rpm. After 12 hours, the glucose was consumed almost completely.

A 3-L conical flask was charged with a medium containing 1.5 g of magnesium sulfate·7 hydrate, 60 mg of ferrous sulfate·7 hydrate, 60 mg of manganese sulfate·hydrate, 600 μg of D-biotin, 600 μg of thiamin hydrochloride, 5 ml of antifoaming agent (Adecanol LG294: product of Asahi Denka), and 1.5 L of distilled water. The resulting medium was sterilized by heating at 120° C. for 20 minutes. After cooling to room temperature, cells collected by centrifugal separation, at 10000×g for 5 minutes, of the culture solution obtained by the above-described main culture were added to the resulting medium, followed by re-suspension to give its O.D. (660 nm) of 60. In a 5-L jar fermenter, 1.5 L of the resulting suspension and 1.5 L of a 20% glucose solution sterilized in advance were charged and mixed. The resulting mixture was kept at 35° C. The reaction was effected while maintaining the pH at 7.6 with 2M ammonium carbonate, aerating at 500 mL/min and stirring at 300 rpm. Almost all the amount of glucose was consumed about 50 hours after the reaction was started. Accumulation of 57 g/L of succinic acid was observed. The resulting fermentation liquid was separated into cells and supernatant by centrifugal separation at 10000×g for 5 minutes and ultrafiltration (NTU-3000-C1R, product of Nitto Denko). The above-described operation was performed 30 times to yield 103 L of a supernatant of a succinic acid fermentation liquid.

<Purification of Succinic Acid from Succinic Acid Fermentation Liquid>

The supernatant of a succinic acid fermentation liquid (103 L, succinic acid content: 5.97 kg) obtained as described above was concentrated in a jacketed agitation tank under reduced pressure, whereby 17.8 kg (calculated value) of a concentrate having a succinic acid concentration of 32.9% and ammonia concentration of 11.9% was obtained. To the resulting concentrate was added 8.58 kg of acetic acid (product of Daicel Chemical) and the resulting mixture was cooled to 30° C. To the reaction mixture was added 4.0 kg of methanol (product of Kishida Chemical), followed by cooling to 15° C. After stirring for one hour, stirring was continued for 4 hours at 20° C.

Crystals thus precipitated were filtered through a centrifugal filter to yield 4.95 kg of crystals containing 74.6% of succinic acid, 3.5% of acetic acid and 12.2% of ammonia.

To 11.3 kg of acetic acid was added 4.9 kg of the resulting crystals and the latter was dissolved in the former at 85° C. The resulting solution was then cooled immediately to 20° C. The crystals had already precipitated, but stirring was continued for further 3 hours and then filtration was conducted through a centrifugal filter, whereby 2.44 kg of crystals containing 87.9% of succinic acid, 8.4% of acetic acid and 0.6% of ammonia were obtained.

The resulting crystals were washed with 3.5 L of demineralized water cooled to 5° C. while sprinkling it to them. Filtration of them through a centrifugal filter yielded 2.08 kg of crystals containing 90% of succinic acid, 1.7% of acetic acid, and 0.05% (about 500 ppm) of ammonia.

In 28.5 L of demineralized water, 2.0 kg of the resulting crude succinic acid crystals were dissolved and the resulting solution was caused to pass through a tower filled with 1 L of an ion exchange resin (SK1BH, product of Mitsubishi Chemical) at SV-2, whereby about 33 L of a treated solution was obtained. The resulting solution was concentrated to about 5.2 L while continuously feeding it to a rotary evaporator under reduced pressure. Crystals had already been precipitated at that stage. After the concentrate was cooled to 5° C. and stirring was continued for 2 hours, the reaction mixture was filtered to yield 1.76 kg of crystals having a succinic acid content of 96.7%. Drying of the crystals in a vacuum drier produced 1.68 kg of succinic acid.

<Preparation of 1,4-butanediol>

From the biomass-resource-derived succinic acid obtained by the above-described process, 1,4-butanediol was prepared in a known manner. Such 1,4-butanediol was obtained by the process as described below.

A mixture of 100 parts by weight of biomass-resource-derived succinic acid, 317 parts by weight of methanol and 2 parts by weight of concentrated sulfuric acid (97%) was stirred for 2 hours under reflux. After cooling, 3.6 parts by weight of sodium hydrogen carbonate was added to the reaction mixture, followed by stirring at 60° C. for 30 minutes. After distillation under normal pressure and filtration of the distillation residue, distillation was conducted under reduced pressure to yield dimethyl succinate (yield: 93%). In the presence of 15 parts by weight of a CuO—ZnO catalyst (T-8402, product of Süd-chemie), 100 parts by weight of the resulting dimethyl succinate was heated to 230° C. in 1 hour in an autoclave (HASTELLOY C) having a capacity about 4 times the volume of the dimethyl succinate charged while stirring under hydrogen pressure of 5 MPa. The reaction mixture was then stirred for 9 hours at 230° C. under hydrogen pressure of 15 MPa. The reaction mixture was cooled and then degasified. The catalyst was filtered off from the reaction mixture. The filtrate was distilled under reduced pressure to yield purified 1,4-butanediol (yield: 819). The purified 1,4-butanediol thus prepared contained 0.7 ppm of nitrogen atoms, but it contained no sulfur atoms. In addition, 1,4-butanediol contained 1000 ppm of 2-(4-hydroxybutyloxy)tetrahydrofuran as an oxidation product.

<Preparation of Polyester and Pellets Thereof by Using Biomass-Resource-Derived Succinic Acid Having a Nitrogen Atom Content of 5 ppm and a Sulfur Atom Content of 0.2 ppm>

Example 1

A reactor equipped with a stirrer, nitrogen gas inlet, heater, thermometer, and pressure reduction exhaust port was charged with 100 parts by weight of biomass-resource-derived succinic acid (YI=2.5) having a nitrogen atom content of 5 ppm and a sulfur atom content of 0.2 ppm, 88.5 parts by weight of industrial-grade 1,4-butanediol manufactured by Mitsubishi Chemical, 0.37 part by weight of malic acid, and 5.4 parts by weight of a 88% aqueous solution of lactic acid having 0.98 wt. % of germanium dioxide dissolved therein as a catalyst. After pressure reduction (ultimate vacuum: 0.2 kPa), a pressure recovery operation to atmospheric pressure was performed three times with a nitrogen gas, whereby the atmosphere in the system became a nitrogen one.

The temperature in the system was then raised to 220° C. while stirring at 150 rpm and reaction was conducted at this temperature for 1 hour. The temperature was then raised to 230° C. in 30 minutes and at the same time, the pressure was reduced to $0.07 \times 10^3$ Pa in 1.5 hours. The reaction was conducted for 1.8 hours under the sane degree of pressure reduction. After pressure reduction, the stirring rotation speed of the stirrer was reduced in stages to 150 rpm, 60 rpm and 40 rpm and the rotation speed for 30 minutes prior to the completion of the polymerization was set at 6 rpm. The polyester thus obtained was withdrawn in the form of strands from the bottom of the reactor at 220° C. After the strands were caused to go into water of 10° C., they were cut into white pellets (yellowness degree YI: 11). The white polyester pellets thus obtained had a minimum diameter of 2 nm and maximum diameter of 3.5 mm. Drying of the pellets at 80° C. for H hours under vacuum yielded pellets having a water content of 358 ppm. The polyester after drying had a nitrogen atom content of 2 ppm and a sulfur atom content of 0.1 ppm and the polyester had a reduced viscosity (ηsp/c) of 2.5 and an amount of terminal carboxyl groups of 26 equivalents/metric ton. The polyester (0.5 g) thus obtained was dissolved uniformly in 1 dL of phenol/tetrachloroethane (1/1 (mass ratio) mixture) at room temperature.

The resulting dry pellets were stored for a half year in a bag made of a polyester/aluminum/polyethylene composite film under light shielding condition, but a marked deterioration in tensile elongation property of the pellets was not observed.

When the pellets were dried by heating at 100° C. for 72 hours under vacuum in order to reduce its water content further, coloration of the polymer was observed, suggesting that drying for a long period of time is not preferred.

Example 2

In a similar manner to that employed in Example 1 except for the use of 100 parts by weight of the biomass-resource-derived succinic acid of Example 1 having a nitrogen atom content of 5 ppm and a sulfur atom content of 0.2 ppm, 32 parts by weight of industrial-grade adipic acid manufactured by Asahi Kasei, 111.6 parts by weight of industrial-grade 1,4-butanediol manufactured by Mitsubishi Chemical, 0.48 part by weight of malic acid, and 7.2 parts by weight of a 88% aqueous solution of lactic acid having germanium dioxide dissolved therein in a concentration of 0.98% by weight in advance as a catalyst, white pellets (yellowness degree YI: 13) similar to those obtained in Example 1 were obtained (reduced viscosity (ηsp/c): 2.4, an amount of terminal carboxyl group: 22 equivalents/metric ton). The polymerization reaction time under reduced pressure of $0.07 \times 10^3$ Pa was 1.6 hours. The polyester (0.5 g) thus obtained was dissolved uniformly in 1 dL of phenol/tetrachloroethane (1/1 (mass ratio) mixture) at room temperature.

Example 3

Under similar conditions to those employed in Example 2 except for the use of 100 parts by weight of the biomass-resource-derived succinic acid of Example 1 having a nitrogen atom content of 5 ppm and a sulfur atom content of 0.2 ppm, 81.4 parts by weight of industrial-grade 1,4-butanediol manufactured by Mitsubishi Chemical, 6.3 parts by weight of ethylene glycol, 0.37 part by weight of malic acid, and 5.4 parts by weight of a 881 aqueous solution of lactic acid having germanium dioxide dissolved therein in a concentration of 0.98% by weight in advance as a catalyst, white pellets similar to those obtained in Example 1 were obtained (reduced viscosity (ηsp/c): 2.4, an amount of terminal carboxyl group: 21 equivalents/metric ton). The polyester (0.5 g) thus obtained was dissolved uniformly in 1 dL of phenol/tetrachloroethane (1/1 (mass ratio) mixture) at room temperature.

Example 4

Under similar conditions to those employed in Example 1 except for the use of 100 parts by weight of the biomass-resource-derived succinic acid of Example 1 having a nitrogen atom content of 5 ppm and a sulfur atom content of 0.2 ppm, 81.4 parts by weight of industrial-grade 1,4-butanediol manufactured by Mitsubishi Chemical, 12.3 parts by weight of 1,4-cyclohexanedimethanol, 0.37 part by weight of malic acid, and 5.4 parts by weight of a 880 aqueous solution of lactic acid having 0.98 wt. % of germanium dioxide dissolved therein in advance as a catalyst, white pellets similar to those obtained in Example 1 were obtained (reduced viscosity (ηsp/c): 2.6, an amount of terminal carboxyl group: 17 equivalents/metric ton). The polymerization reaction time under reduced pressure of $0.07 \times 10^3$ Pa was 3.8 hours. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 12 ppm and a Sulfur Atom Content of 5 ppm>

Example 5

Under similar conditions to those employed in Example 1 except for the use of 100 parts by weight of biomass-resource-derived succinic acid (yellowness degree YI: 7) having a nitrogen atom content of 12 ppm and a sulfur atom content of 5 ppm instead of 100 parts by weight of the biomass-resource-derived succinic acid of Example 1 having a nitrogen atom content of 5 ppm and a sulfur atom content of 0.2 ppm, white pellets similar to those obtained in Example 1 were obtained. The polymerization reaction time under reduced pressure of $0.07 \times 10^3$ Pa was 2 hours.

The polyester thus obtained (yellowness degree YI: 22) had a nitrogen atom content of 3.6 ppm, a sulfur atom content of 2.6 ppm, a reduced viscosity (ηsp/c) of 2.3 and an amount of terminal carboxyl groups of 19 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 16 ppm and a Sulfur Atom Content of 2 ppm>

Example 6

Under similar conditions to those employed in Example 1 except for the use of 100 parts by weight of biomass-resource-derived succinic acid (yellowness degree YI: 3) having a nitrogen atom content of 16 ppm and a sulfur atom content of 2 ppm instead of 100 parts by weight of the biomass-resource-derived succinic acid of Example 1 having a nitrogen atom content of 5 ppm and a sulfur atom content of 0.2 ppm, white pellets similar to those obtained in Example 1 were obtained. The polymerization reaction time under reduced pressure of $0.07 \times 10^3$ Pa was 2.1 hours.

The polyester thus obtained (yellowness degree YI: 19) had a nitrogen atom content of 3.4 ppm, a sulfur atom content of 1.4 ppm, a reduced viscosity (ηsp/c) of 2.4 and an amount of terminal carboxyl groups of 15 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 115 ppm and a Sulfur Atom Content of 0.3 ppm>

Example 7

Under similar conditions to those employed in Example 1 except for the use of 100 parts by weight of biomass-resource-derived succinic acid having a nitrogen atom content of 115 ppm and a sulfur atom content of 0.3 ppm instead of 100 parts by weight of the biomass-resource-derived succinic acid of Example 1 having a nitrogen atom content of 5 ppm and a sulfur atom content of 0.2 ppm, pellets similar to those obtained in Example 1 were prepared. The polymerization reaction time under reduced pressure of $0.07 \times 10^3$ Pa was 2.9 hours.

The polyester thus obtained (yellowness degree YI: 23) had a nitrogen atom content of 19 ppm, a sulfur atom content of 0.2 ppm, a reduced viscosity (ηsp/c) of 2.5 and an amount of terminal carboxyl groups of 19 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 180 ppm and a Sulfur Atom Content of 1 ppm>

Example 8

Under similar conditions to those employed in Example 1 except for the use of 100 parts by weight of biomassresource-derived succinic acid having a nitrogen atom content of 180 ppm and a sulfur atom content of 1 ppm instead of 100 parts by weight of the biomass-resource-derived succinic acid of Example 1 having a nitrogen atom content of 5 ppm and a sulfur atom content of 0.2 ppm, polyester pellets similar to those obtained in Example 1 were obtained. The polymerization reaction time under reduced pressure of $0.07 \times 10^3$ Pa was 2.6 hours.

The polyester thus obtained (yellowness degree YI: 37) had a nitrogen atom content of 22 ppm, a sulfur atom content of 0.6 ppm, a reduced viscosity ($\eta sp/c$) of 2.5 and an amount of terminal carboxyl groups of 19 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 230 ppm and a Sulfur Atom Content of 1 ppm>

Example 9

Under similar conditions to those employed in Example 1 except for the use of 100 parts by weight of biomass-resource-derived succinic acid (yellowness degree YI: 11) having a nitrogen atom content of 230 ppm and a sulfur atom content of 1 ppm instead of 100 parts by weight of the biomass-resource-derived succinic acid of Example 1 having a nitrogen atom content of 5 ppm and a sulfur atom content of 0.2 ppm, polyester pellets similar to those obtained in Example 1 were prepared. The polymerisation reaction time under reduced pressure of $0.07 \times 10^3$ Pa was 2.6 hours.

The polyester thus obtained (yellowness degree YI: 39) had a nitrogen atom content of 27 ppm, a sulfur atom content of 0.6 ppm, a reduced viscosity (rap/c) of 2.4 and an amount of terminal carboxyl groups of 19 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 30 ppm and a Sulfur Atom Content of 18 ppm>

Example 10

Under similar conditions to those employed in Example 1 except for the use of 100 parts by weight of biomass-resource-derived succinic acid having a nitrogen atom content of 30 ppm and a sulfur atom content of 18 ppm instead of 100 parts by weight of the biomass-resource-derived succinic acid of Example 1 having a nitrogen atom content of 5 ppm and a sulfur atom content of 0.2 ppm, polyester pellets similar to those obtained in Example 1 were prepared. The polymerization reaction time under reduced pressure of $0.07 \times 10^3$ Pa was 3.3 hours.

The brown polyester thus obtained (yellowness degree YI: 42) had a reduced viscosity ($\eta sp/c$) of 2.4 and an amount of terminal carboxyl groups of 18 equivalents/metric ton. The polyester (0.5 g) thus obtained was dissolved almost uniformly in 1 dL of phenol/tetrachloroethane (1/1 (mass ratio) mixture) at room temperature, but trace insoluble matters were observed.

<Polyester Prepared Using Biomass-Resource-Derived Succinic Acid Having a Nitrogen Atom Content of 5 ppm and a Sulfur Atom Content of 0.2 ppm and Biomass-Resource-Derived 1,4-Butanediol Having a Nitrogen Atom Content of 0.7 ppm>

Example 11

Under similar conditions to Example 1 except for the use of 88.5 parts by weight of biomass-resource-derived 1,4-butanediol having a nitrogen atom content of 0.7 ppm instead of 88.5 parts by weight of the industrial-grade 1,4-butanediol of Example 1 manufactured by Mitsubishi Chemical, polyester pellets similar to those obtained in Example 1 were obtained. The polymerization reaction time under reduced pressure of $0.07 \times 10^3$ Pa was 3 hours.

The polyester thus obtained (yellowness degree YI: −1) had a reduced viscosity ($\eta sp/c$) of 2.5 and an amount of terminal carboxyl groups of 21 equivalents/metric ton. The polyester (0.5 g) thus obtained was dissolved uniformly in 1 dL of phenol/tetrachloroethane (1/1 (mass ratio) mixture) at room temperature.

Example 12

A reactor equipped with a stirrer, nitrogen gas inlet, heater, thermometer, and pressure reduction exhaust port was charged with 100 parts by weight of the biomass-resource-derived succinic acid of Example 1 having a nitrogen atom content of 5 ppm and a sulfur atom content of 0.2 ppm, 80.4 parts by weight of biomass-resource-derived 1,4-butanediol having a nitrogen atom content of 0.7 ppm, and 0.37 part by weight of malic acid. After pressure reduction (ultimate vacuum: 0.2 kPa), a pressure recovery operation to atmospheric pressure was performed three times with a nitrogen gas, whereby an atmosphere in the system was changed to a nitrogen one.

The temperature in the system was then raised to 220° C. while stirring and reaction was conducted at this temperature for 1 hour. Then, a catalyst solution obtained by diluting 0.11 part by weight of tetra-n-butyl titanate in 0.4 part by weight of butanol was added to the reaction system. The temperature was raised to 230° C. in 30 minutes, while the pressure was reduced to $0.07 \times 10^3$ Pa in 1.5 hours. The reaction was conducted for 2 hours under the same degree of pressure reduction. While controlling the resin temperature to 220° C., the polyester thus obtained was withdrawn in the form of strands from the bottom of the reactor at 220° C. After the strands were caused to go into water of 10° C., they were cut by a cutter, whereby pellets similar to Example 1 (reduced viscosity ($\eta sp/c$) of 2.5 and an amount of terminal carboxyl groups of 12 equivalents/metric ton) were obtained. The polyester (0.5 g) thus obtained was dissolved uniformly in 1 dL of phenol/tetrachloroethane (1/1 (mass ratio) mixture) at room temperature.

<Polyester Prepared Using Petroleum-Derived Succinic Acid Containing Neither Nitrogen Atom Nor Sulfur Atom and Biomass-Resource-Derived 1,4-Butanediol Containing a Nitrogen Atom Content of 0.7 ppm>

Example 13

Under similar conditions to those employed in Example 1 except for the use of 100 parts by weight of succinic acid (industrial grade, manufactured by Kawasaki Kasei Chemicals, yellow ness degree YI: 2) containing neither nitrogen atom nor sulfur atom instead of the succinic acid of Example 1 and 88.5 parts by weight of biomass-resource-derived 1,4-butanediol instead of the petroleum-derived 1,4-butanediol of Example 1, polyester pellets similar to those obtained in Example 1 were obtained. The polymerization reaction time under reduced pressure of $0.07 \times 10^3$ Pa was 3.4 hours.

The polyester thus obtained (yellowness degree YI: 7) had a nitrogen atom content of 0.5 ppm, a reduced viscosity (ηsp/c) of 2.5 and an amount of terminal carboxyl groups of 28 equivalents/metric ton. The polyester (0.5 g) thus obtained was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 3 ppm and a Sulfur Atom Content of 34 ppm>

Example 14

Under similar conditions to those employed in Example 1 except for the use of 100 parts by weight of biomass-resource-derived succinic acid having a nitrogen atom content of 3 ppm and a sulfur atom content of 34 ppm instead of the succinic acid of example 1 polyester pellets similar to those obtained in Example 1 were prepared. The polymerization reaction time under reduced pressure of $0.07 \times 10^3$ Pa was 7 hours.

The polyester thus obtained (yellowness degree YI: 38) had a reduced viscosity (ηsp/c) of 2.4 and an amount of terminal carboxyl groups of 30 equivalents/metric ton. The polyester (0.5 g) thus obtained was dissolved in 1 dL of phenol/tetrachloroethane (1/1 (mass ratio) mixture) at room temperature, but a small amount of insoluble matters was observed.

<Polyester Prepared Using Petroleum-Derived and Nitrogen-Atom-Free Dimethyl Terephthalate and Biomass-Resource-Derived 1,4-Butanediol Having a Nitrogen Atom Content of 0.7 ppm>

Example 15

A reactor equipped with a stirrer, nitrogen gas inlet, heater, thermometer, and pressure reduction exhaust port was charged with 132 parts by weight of the dimethyl terephthalate, 74 parts by weight of biomass-resource-derived 1,4-butanedial having a nitrogen atom content of 0.7 ppm, and 1.7 parts by weight of a 1,4-butanediol solution having 6 wt. % of tetrabutyl titanate dissolved in advance therein as a catalyst. By purging with nitrogen under reduced pressure, the atmosphere in the system was changed to a nitrogen one.

After the temperature in the reaction system was raised to 150° C. under stirring, reaction was conducted for 3 hours while heating to 215° C. The temperature was then raised to 245° C. and at the same time, the pressure was reduced to $0.07 \times 10^3$ Pa in 1.5 hours. Without changing the degree of pressure reduction, the reaction was conducted for 1.5 hours and polymerization reaction was completed. The polyester thus obtained was withdrawn in the form of strands from the bottom of the reactor. After the strands were caused to go into water of 10° C., they were cut by a cutter, whereby pellets similar to those obtained in Example 1 (yellowness degree YI: 0.4) were obtained.

The polyester thus obtained had a nitrogen atom content of 0.4 ppm, a reduced viscosity (ηsp/c) of 1.2 and an amount of terminal carboxyl groups of 21 equivalents/metric ton. The resulting polyester (0.5 g) was dissolved uniformly in 1 dL of phenol/tetrachloroethane (1/1 (mass ratio) mixture) at room temperature.

<Polyester Prepared Using Biomass-Resource-Derived Succinic Acid Having a Nitrogen Atom Content of 660 ppm and a Sulfur Atom Content of 330 ppm>

Comparative Example 1

Under similar polycondensation conditions to those employed in Example 1 except for the use of 100 parts by weight of biomass-resource-derived succinic acid (yellowness degree YI: 8) having a nitrogen atom content of 660 ppm and a sulfur atom content of 330 ppm instead of the succinic acid used in Example 1, polyester was prepared. Polymerization reaction was performed for 2.5 hours under reduced pressure of $0.07 \times 10^3$ Pa, but the polyester thus obtained was colored dark brown (yellowness degree YI: 60 or greater).

The dark brown polyester thus obtained had a nitrogen atom content of 54 ppm, a sulfur atom content of 16 ppm and reduced viscosity (ηsp/c) of 0.7 and an amount of terminal carboxyl groups of 139 equivalents/metric ton.

<Polyester Prepared Using Biomass-Resource-Derived Succinic Acid Having a Nitrogen Atom Content of 850 ppm and a Sulfur Atom Content of 290 ppm)

Comparative Example 2

Under similar conditions to those employed in Example 1 except for the use of 100 parts by weight of biomass-resource-derived succinic acid (yellowness degree YI: 8) having a nitrogen atom content of 850 ppm and a sulfur atom content of 290 ppm instead of the succinic acid used in Example 1, polyester pellets were prepared. Polymerization reaction was performed for 2.5 hours under reduced pressure of $0.07 \times 10^3$ Pa, but the polyester thus obtained was colored dark brown (yellowness degree YI: 60 or greater).

The dark brown polyester thus obtained had a nitrogen atom content of 51 ppm, a sulfur atom content of 16 ppm and reduced viscosity (ηsp/c) of 1.1 and an amount of terminal carboxyl groups of 69 equivalents/metric ton.

Comparative Example 3

Under similar polycondensation conditions to those employed in Example 12 except that the reaction temperature after the addition of a catalyst obtained by diluting tetra-n-butyl titanate in butanol was changed from 230° C. to 240° C., polyester and pellets thereof was prepared. Polymerization time under reduced pressure of $0.07 \times 10^3$ Pa was 3 hours. The polyester (yellowness degree YI: 19) after drying had a reduced viscosity (ηsp/c) of 2.4 and an amount of terminal carboxyl groups of 54 equivalents/metric ton. The resulting polyester (0.5 g) was dissolved almost uniformly in 1 dL of phenol/tetrachloroethane (1/1 (mass ratio) mixture) at room temperature, but trace insoluble matters were observed.

Comparative Example 4

Under similar conditions to those employed in Example 1 except that 0.74 part by weight of malic acid was charged instead of 0.37 part by weight of malic acid, white polyester pellets similar to Example 1 were prepared. The polymerization time under reduced pressure of $0.07 \times 10^3$ Pa was 1.1 hours. The polyester thus obtained had a reduced viscosity (ηsp/c) of 3.2 and an amount of terminal carboxyl groups of 63 equivalents/metric ton. The resulting polyester (0.5 g) was dissolved almost uniformly in 1 dL of phenol/tetrachloroethane (1/1 (mass ratio) mixture) at room temperature, but a small amount of insoluble matters was observed.

Comparative Example 5

By using a commercially available petroleum-derived raw material containing neither nitrogen atom nor sulfur atom instead of the succinic acid prepared by the fermentation process in Example 1, a polyester was prepared. More specifically, the polyester similar to that prepared in Example 1 was prepared in a similar manner to that employed in Example 1 except that industrial-grade succinic acid manufactured by Kawasaki Kasei Chemicals and industrial grade 1,4-butanediol manufactured by Mitsubishi Chemical. Neither nitrogen atom nor sulfur atom was detected from the polyester thus prepared.

It has been found from Examples and Comparative Examples, that coloration of a polyester or inhibition against polymerization tends to be severe with an increase in the content of a nitrogen atom or sulfur atom in the polyester. In particular, with an increase in the content of a nitrogen atom, the coloration of the polymer tends to be severer. When a sulfur atom content exceeds a certain amount or preparation is performed at high temperatures, an increase in the amount of terminal carboxyl groups occurs and an amount of insoluble matters in an organic solvent, which are presumed to be generated by the partial gelation, tends to be greater. It is known that mixing of such insoluble matters in the product damages the appearance of the product or causes deterioration of its physical properties.

Physical Property Evaluation Example 1

<Evaluation of Storage Stability Based on Water Content in Pellets>

Storage stability of the polyester pellets prepared in Example 1 was evaluated by hermetically sealed pellets in a bag (bag A1) made of a polyester/aluminum/polyethylene composite film. Storage stability was evaluated by a method of hermetically sealed pellets having respective water contents in a bag (bag A1) made of a polyester/aluminum/polyethylene composite film, retaining it in an oven of 40° C., and measuring a solution viscosity (reduced viscosity ($\eta sp/c$)) of each sample for a certain period. Arrival time of the sample to a predetermined reduced viscosity ($\eta sp/c$) as a result of hydrolysis during storage under heating is shown in Table 1.

Example 16

A water content in the polyester pellets prepared in Example 1 was adjusted to 358 ppm by maintaining the pellets under the conditions of 23° C. and 50% RH for a predetermined time. The resulting pellets were hermetically sealed in a bag (bag A1) made of a polyester/aluminum/polyethylene composite film and retained the bag in an oven of 40° C. The solution viscosity (reduced viscosity ($\eta sp/c$)) of each of the samples was measured for a certain period. Arrival time of the sample to a predetermined reduced viscosity ($\eta sp/c$) as a result of hydrolysis during storage under heating is shown in Table 1.

Example 17

In a similar manner to Example 16, a water content in the polyester pellets prepared in Example 1 was adjusted to 472 ppm and storage stability thereof was evaluated. The results are shown in Table 1.

Example 18

In a similar manner to Example 16, a water content in the polyester pellets prepared in Example 1 was adjusted to 796 ppm and storage stability thereof was evaluated. The results are shown in Table 1.

Example 19

In a similar manner to Example 16, a water content in the polyester pellets prepared in Example 1 was adjusted to 1086 ppm and storage stability thereof was evaluated. The results are shown in Table 1.

Comparative Example 6

In a similar manner to Example 16, a water content in the polyester pellets prepared in Example 1 was adjusted to 3151 ppm and storage stability thereof was evaluated. The results are shown in Table 1.

It has been found from Table 1 that a drastic reduction in the reduced viscosity ($\eta sp/c$) during storage occurs when the water content in the pellets during storage exceeds 3000 ppm. Deterioration in the physical properties of the film due to reduction in the reduced viscosity ($\eta sp/c$) is shown in Table 2.

TABLE 1

Arrival time to predetermined reduced viscosity (nsp/c) by hermetically-sealed storage at 40° C.

| | | Reduced viscosity ($\eta sp/c$) | | | | |
|---|---|---|---|---|---|---|
| | | 2.4 | 2.2 | 2.0 | 1.7 | 1.6 |
| Example 16 | Polyester pellets having a water content of 358 ppm | 0 h | 2347 h | 3355 h | — | — |
| Example 17 | Polyester pellets having a water content of 472 ppm | 0 h | 2011 h | 3019 h | — | — |
| Example 18 | Polyester pellets having a water content of 796 ppm | 0 h | 1482 h | 2851 h | — | — |
| Example 19 | Polyester pellets having a water content of 1086 ppm | 0 h | 1314 h | 2682 h | — | — |
| Comparative Example 6 | Polyester pellets having a water content of 3151 ppm | 0 h | 474 h | 810 h | 2011 h | 2682 h |

<Influence of Viscosity Reduction on Physical Properties of Film>

Blown film extrusion of the polyester prepared in Example 1 was carried out. A film having a thickness of 20 pa was formed under the extrusion conditions of an extrusion temperature of 160° C. and blow ratio of 2.5. Deterioration behavior of a physical property (tensile elongation at break) due to viscosity reduction of the film thus formed is shown in Table 2. It is presumed that a reduction in reduced viscosity leads to reduction in tensile elongation at break so that a polyester having a reduced viscosity has poor film formability.

TABLE 2

| | Reduced viscosity($\eta sp/c$) | | | | | | |
|---|---|---|---|---|---|---|---|
| | 2.4 | 2.1 | 2.0 | 1.9 | 1.6 | 1.3 | 0.8 |
| Tensile elongation at break (MD direction (%)) | 410 | 390 | 394 | 320 | 221 | 105 | 0 |

(Note)
Tensile test: in accordance with JIS Z1702
MD: flow direction at the time of film formation Physical Property Evaluation Example 2

<Influence of Amount of Terminal Carboxylic Acid on Hydrolysis Resistance>

The polyester pellets obtained in Example 1, Example 12 and Comparative Example 3 were charged in a thermohygrostat set at 50° C. and 90% RH. For a certain period, the samples were taken out and solution viscosity and amount of terminal carboxylic acid of each of them were measured. The results are shown in Table 3. It has been found from these results that an amount of the terminal carboxylic acid exceeding 50 equivalents/metric ton leads to marked deterioration in the hydrolysis resistance of the polyester and the resulting polyester is not suited for practical use because of low storage properties.

TABLE 3

| Hydrolysis resistance test at 50° C. and 90% RH | | | | | |
| --- | --- | --- | --- | --- | --- |
| Sample | Stored for | 0 day | 7 days | 21 days | 28 days |
| Example 1 | Reduced viscosity ($\eta sp/c$) | 2.5 | 2.0 | 1.7 | 1.2 |
| | Amount of terminal carboxylic acid (equivalent/metric ton) | 26 | 34 | 40 | 57 |
| Example 12 | Reduced viscosity ($\eta sp/c$) | 2.5 | 2.4 | 2.3 | 2.0 |
| | Amount of terminal carboxylic acid (equivalent/metric ton) | 12 | 11 | 13 | 19 |
| Comparative Example 3 | Reduced viscosity ($\eta sp/c$) | 2.4 | 1.9 | 1.5 | 1.0 |
| | Amount of terminal carboxylic acid (equivalent/metric ton) | 54 | 66 | 76 | 100 |

Physical Property Evaluation Example 3

<Evaluation of Biodegradability>

Each of the polyesters prepared in Example 1 and Comparative Example 5 was formed into a film having a thickness of 20 μm by using a blown film extruder at an extrusion temperature of 160° C. and blow ratio of 2.5. The film thus formed was cut into a size of 5 cm×18 cm and was buried in the soil. Biodegradability test was carried out by measuring a weight reduction percentage of the film after 1 month, 2 months, 3 months and 6 months, respectively. The results are shown in Table 4. It has been confirmed from Table 4 that the polyester using succinic acid prepared by the fermentation process had a high biodegradation rate in the soil.

<Biodegradability Test in the Soil>

The film formed by the above-described method was cut into a size of 5 cm×18 cm and buried in the soil. A weight reduction percentage of the film after 1 month, 2 months, 3 months and 6 months was measured respectively. The results are shown in Table 4.

TABLE 4

| Results of weight reduction percentage of film | | | | |
| --- | --- | --- | --- | --- |
| | Average weight reduction percentage (%) | | | |
| Sample | 1 month | 2 months | 3 months | 6 months |
| Polyester prepared in Comparative Example 5 | 5 | 9 | 10 | 31 |
| Polyester prepared in Example 1 | 27 | 64 | 77 | 80 |

Referential Example 6

Molding or forming examples and various physical properties of polyesters prepared in Example 1 and various compositions thereof are shown below as a referential example.

<Preparation of Composition>

Compositions 1 and 2 were prepared in accordance with the respective mixing ratios (wt. %) shown in Table 5. These compositions were prepared at a kneading temperature of 190° C. by using a twin-screw extruder (KZW15), product of TECHNOVEL.

TABLE 5

| | Composition 1 | Composition 2 |
| --- | --- | --- |
| Polyester of Example 1 | 70 | 70 |
| Talc | 30 | |
| Ecoflex | | 30 |

(Note)
Talc: "PKP-53S", product of Fuji Tala
Ecoflex: product of BASF Japan

Compositions 3 to 5 were prepared in accordance with the mixing ratios (wt. %) shown Table 6. The compositions were prepared at a kneading temperature of 190° C. by using a Labo Plastomill, product of Toyo Seiki Seisaku-sho.

TABLE 6

| | Composition 3 | Composition 4 | Composition 5 |
| --- | --- | --- | --- |
| Polyester of Example 1 | 75 | 50 | 25 |
| Polylactic acid | 25 | 50 | 75 |

(Note)
Polylactic acid: "LACEA H-400", product of Mitsui Chemical

<Injection Molding>

The samples shown in Table 7 were injection molded using a benchtop injection molder, MINIMAX, product of CSI. The molding temperature was set at 200° C. Evaluation results of physical properties are also shown in Table 7. Evaluation of each sample was carried out at 23° C. and 50% RH.

TABLE 7

| | Unit | Polyester of Example 1 | Composition 1 | Composition 2 | Composition 3 | Composition 4 |
| --- | --- | --- | --- | --- | --- | --- |
| Izod Impact strength | kJ/m$^2$ | 8.9 | 5.0 | 9.5 | 5.2 | 3.0 |

Note)
Izod impact test: in accordance with JIS K7110 (unnotched)

<Sheet Formation>

The samples shown in Table 8 were formed into a sheet by using a T-die film forming machine. The sheet having a thickness of 500 μm was formed at a forming temperature of 200° C. and roll temperature of 30° C. Evaluation results of physical properties are also shown in Table B. Evaluation of each physical property was made at 23° C. and 50% RH.

TABLE 8

|  | Unit | Direction | Polyester of Example 1 | Composition 1 |
| --- | --- | --- | --- | --- |
| Tensile yield strength | MPa | MD | 35 | 40 |
|  |  | TD | 36 | 33 |
| Tensile strength at break | MPa | MD | 38 | 45 |
|  |  | TD | 30 | 25 |
| Tensile elongation at break | % | MD | 310 | 320 |
|  |  | TD | 260 | 30 |
| Flexural strength | Mpa | MD | — | 36 |
|  |  | TD | — | 42 |
| Flexural modulus | MPa | MD | — | 2850 |
|  |  | TD | — | 3450 |

(Note)
Tensile test: in accordance with JIS K7113
Dumbbell No. 2 was used (extension rate: 50 mm/min)
Flexural test: in accordance with JIS K7203
MD: Flow direction at the time of sheet formation
TD: direction perpendicular to the flow <Film Formation>

Blown film extrusion was performed using the samples shown in Table 9. The film having a thickness of 20 μm was formed at a forming temperature of 160° C. and blow ratio of 2.5. Evaluation results of the physical properties are also shown in Table 9. Evaluation of each of the physical properties was made at 23° C. and 50% RH.

TABLE 9

|  | Unit | Direction | Polyester of Example 1 | Composition 5 |
| --- | --- | --- | --- | --- |
| Tensile yield strength | MPa | MD | 35 | 20 |
|  |  | TD | 32 | 20 |
| Tensile strength at break | MPa | MD | 60 | 60 |
|  |  | TD | 25 | 60 |
| Tensile elongation at break | % | MD | 410 | 650 |
|  |  | TD | 100 | 730 |

(Note)
Tensile test: in accordance with JIS Z1702
MD: Flow direction at the time of sheet formation
TD: Direction perpendicular to the flow <Foam Molding>

The polyester prepared in Example 1 was pressed at 190° C. and 10 MPa into a sheet having a thickness of 1 m. The sheet thus obtained, in the solid form, was charged in a pressure vessel equipped with valves. The temperature in the pressure vessel was raised to 100° C. by an outside heating source and at the same time, carbon dioxide was charged in the pressure vessel. At the time of charging, the pressure was raised to 15 MPa by pumping. The temperature and pressure were kept at 100° C. and 15 MPa, respectively, for 2 hours. Then, the valves of the pressure vessel were all opened to release the pressure in the pressure battle at a burst, whereby a foamed product was obtained. The foamed product thus obtained did not emit bubbles even pressed in water and thus had a high closed-cell foam ratio.

The present invention was so far described specifically based on some embodiments. It is apparent to those skilled in the art that various changes or modifications can be made without departing from the intention and scope of the present invention. The present application is based on Japanese Patent Application (Japanese Patent Application No. 2005-125318) filed on Apr. 22, 2005, Japanese Patent Application (Japanese Patent Application No. 2005-125319) filed on Apr. 22, 2005, Japanese Patent Application (Japanese Patent Application No. 2005-125320) filed on Apr. 22, 2005, Japanese Patent Application (Japanese Patent Application No. 2005-125321) filed on Apr. 22, 2005, Japanese Patent Application (Japanese Patent Application No. 2005-127757) filed on Apr. 26, 2005, Japanese Patent Application (Japanese Patent Application No. 2005-127761) filed on Apr. 26, 2005, Japanese Patent Application (Japanese Patent Application No. 2005-128886) filed on Apr. 27, 2005, Japanese Patent Application (Japanese Patent Application No. 2005-375353) filed on Dec. 27, 2005, Japanese Patent Application (Japanese Patent Application No. 2005-375354) filed on Dec. 27, 2005, and Japanese Patent Application (Japanese Patent Application No. 2005-375355) filed on Dec. 27, 2005, which are incorporated herein by reference.

INDUSTRIAL APPLICABILITY

The birth of the polyester of the present invention and background thereof will next be described in detail. In a large cycle on the earth in the atmosphere, the appearance of the polyester of the present invention can be evaluated from many standpoints such as conservation of earth's environment, resource saving, pollution prevention, aesthetic environmental protection and new-technology-oriented development.

The polyester of the present invention is characterized by its distinct difference in the significance of existence in the earth's environment from the conventional polyesters derived from underground fossil fuels, for example, petroleum-resource-derived polyesters.

In particular, a diol unit or dicarboxylic acid unit obtained from natural materials, which have vegetated under the earth's environment in the present atmosphere, by the fermentation process or the like is used as a monomer of the polyester so that raw materials are available at a very low cost. In addition, they can be supplied stably with less risk because the production of plants can be enhanced artificially, systematically and arbitrarily so that plant raw materials can be produced in various regions or various countries without limiting the production site. Moreover, since a cycle from raw materials of the polyester to the final discarding stage of it after use, more specifically, a cycle from procurement of monomers and synthesis of polyester to biodegradation of it is carried out based only on the natural process under the earth's environment in the atmosphere, the polyester of the present invention can give consumers a feeling of reliability and security. These are of course non-negligible and important backgrounds in the technological development, growth of the industry, and expansion of consumer society related to the polyester.

Response to the demands of the present age built on technological progress however mainly contributes to the birth of the polyester of the present invention. Countermeasures against worsening of the earth's environment due to, for example, a so-called greenhouse effect by a $CO_2$ gas, countermeasures against a sense of crisis over wasteful use and depletion of petroleum resources, and recent advance in peripheral technology, which is a more important reason, more specifically, marked advance of biotechnology such as fermentation technology enable the birth of the polyester of the present invention. In the first place, the polyester of the present invention is produced by a method depending on the vegetation in the atmosphere. In the production of raw material plants by this method, a large amount of carbon dioxide is absorbed. This absorption amount is designated as Abs. The plants emit a small amount of carbon dioxide and thermal energy during processing, fermentation and treatment, but a diol unit or a dicarboxylic acid can be prepared therefrom easily. When the polyester of the present invention obtained by polymerization is buried in the ground, left in water or left in seawater, it is decomposed by microorganisms and the like and substantially releases water and carbon dioxide. This release amount is designated as Rel. There is a small difference between Abs and Rel. In this sense, the difference between the absorbed amount and released amount of carbon dioxide in the atmosphere will be relatively small. This invention is advantageous not only in the balance between the absorption and release of carbon dioxide as described above but also energy balance. In the present invention intended to depend on vegetation, an increase in the amount of a $CO_2$ gas emitted newly to the atmosphere, which is the problem of the conventional fossil-resource-dependent type polyester, can be prevented as much as possible.

As secondary effects, the polyester material of the present invention not only has commendable physical properties, structure and function, but also is very eco-friendly and safe polyester. The process of it from vegetation of raw materials to disappearance of them as described above has a potential possibility of actualizing a recycling society which cannot be expected from the fossil-fuel-derived polyester. This provides, in future production process of polyesters, a new recycling-oriented polyester production process which is different from what the conventional fossil-fuel-dependent polyester aims at. It is the plastic that meets the needs of the age and adopts the leading-age technology quickly and as a result, essentially changes the perception of the so-called plastic industries. It can be evaluated even as an innovative plastic which can start the second plastic age based on the recent remarkable technological growth. The polyester of the present invention has thus a high potential evaluation and value so that it contributes greatly to the expansion of application fields, growth and consumption of a polyester as one typical example of plastic materials.

The invention claimed is:

1. A biomass-resource-derived polyester, comprising as a main repeating unit thereof a dicarboxylic acid unit and a diol unit, wherein at least one of the dicarboxylic acid and diol used as raw materials of the polyester is obtained from biomass resources, a nitrogen atom content in the polyester except nitrogen atoms contained in covalently bonded functional groups in the molecule of the polyester is 0.01 ppm to 50 ppm, and wherein a metal amount of a polymerization catalyst selected from the group consisting of titanium, zirconium, tin, antimony, cerium, germanium, zinc, cobalt, manganese, iron, aluminum, magnesium, calcium, strontium, sodium and potassium in the polyester, is 5 ppm to 130 ppm.

2. The biomass-resource-derived polyester according to claim 1, wherein an amount of terminal acid in the polyester is 50 equivalents/metric ton or less.

3. The biomass-resource-derived polyester according to claim 1, wherein a sulfur atom content in the polyester is, in terms of a mass ratio, 0.0001 ppm to 50 ppm relative to the polyester.

4. The biomass-resource-derived polyester according to claim 1, wherein the polyester has a water content, in terms of a mass ratio, of 1 ppm to 3000 ppm relative to the polyester.

5. The biomass-resource-derived polyester according to claim 1, wherein the reduced viscosity ($\eta sp/c$) of the polyester is 1.0 or greater.

6. The biomass-resource-derived polyester according to claim 1, wherein the polyester has a YI value of −10 to 30.

7. The biomass-resource-derived polyester according to claim 1, which comprises at least one tri- or higher functional compound unit selected from the group consisting of tri- or higher functional polyhydric alcohols, tri- or higher functional polycarboxylic acids, and tri- or higher functional oxycarboxylic acids.

8. The biomass-resource-derived polyester according to claim 7, wherein the content of the tri- or higher functional compound unit is 0.0001 mole % to 0.5 mole % based on 100 mole % of all the monomer units constituting the polyester.

9. The biomass-resource-derived polyester according to claim 1, wherein the dicarboxylic acid unit constituting the main repeating unit of the polyester is a biomass-resource-derived succinic acid unit.

10. A biomass-resource-derived polyester resin composition, which comprises 99.9 to 0.1 wt. % of a polyester according to claim 1 and 0.1 to 99.9 wt. % of a thermoplastic resin, biodegradable resin, natural resin or polysaccharide.

11. A molded product obtained by molding a biomass-resource-derived polyester according to claim 1.

12. The molded product according to claim 11, which is a film, a sheet, an injection molded product, or a foam molded product.

13. A pellet obtained from a biomass-resource-derived polyester according to claim 1.

* * * * *